United States Patent
Kiefer et al.

(10) Patent No.: US 11,458,669 B2
(45) Date of Patent: Oct. 4, 2022

(54) PROCESS OF CHANGING CROSS SECTIONAL SHAPE WITHIN A TEXTILE

(71) Applicant: ATEX Technologies, Inc., Pinebuff, NC (US)

(72) Inventors: Robert A. Kiefer, Quakertown, PA (US); Nathan Spangenberg, Quakertown, PA (US); Stephanie Burke, Quakertown, PA (US); Matthew Oltman, Perkasie, PA (US); Thomas R. Molz, Warrington, PA (US)

(73) Assignee: ATEX Technologies, Inc., Pinebluff, NC (US)

( * ) Notice: Subject to any disclaimer, the term of this patent is extended or adjusted under 35 U.S.C. 154(b) by 836 days.

(21) Appl. No.: 16/254,414

(22) Filed: Jan. 22, 2019

(65) Prior Publication Data
US 2019/0168441 A1 Jun. 6, 2019

Related U.S. Application Data

(63) Continuation-in-part of application No. PCT/US2017/043268, filed on Jul. 21, 2017.
(Continued)

(51) Int. Cl.
*B29C 55/30* (2006.01)
*D06M 10/00* (2006.01)
(Continued)

(52) U.S. Cl.
CPC ........ *B29C 55/30* (2013.01); *A61B 17/06166* (2013.01); *A61L 17/14* (2013.01);
(Continued)

(58) Field of Classification Search
CPC .............. B29C 55/30; A61B 17/06166; A61B 2017/00526; A61B 2017/0619;
(Continued)

(56) References Cited

U.S. PATENT DOCUMENTS

| 4,272,950 A | 6/1981 | Bompard |
| 6,716,234 B2 | 4/2004 | Grafton et al. |

(Continued)

FOREIGN PATENT DOCUMENTS

| EP | 1623726 A2 | 2/2006 |
| WO | WO 2007/084762 | 7/2007 |

(Continued)

OTHER PUBLICATIONS

DYNACORD Suture: The FUTURE of Soft Tissue Repair; retrieved Jun. 8, 2022.
(Continued)

*Primary Examiner* — Tabassom Tadayyon Eslami
(74) *Attorney, Agent, or Firm* — Nelson Mullins Riley & Scarborough LLP

(57) ABSTRACT

Methods, systems, and devices for changing cross-sectional sizes and/or shapes of flat braided sutures and the resulting constructs are disclosed. The flat braided sutures can have a textile first cross-sectional shape that can be changed to a textile second cross-sectional shape. The systems can have a heater and a die. The flat braided sutures can be movable through the heater and the die. When the flat braided sutures are in the heater, the flat braided sutures can be heatable from a textile first temperature to a textile second temperature greater than the textile first temperature. When the flat braided sutures are at the textile second temperature, the textile first cross-sectional shape can be changeable to the textile second cross-sectional shape.

7 Claims, 12 Drawing Sheets

Related U.S. Application Data

(60) Provisional application No. 62/365,467, filed on Jul. 22, 2016.

(51) Int. Cl.
  *A61L 17/14* (2006.01)
  *A61B 17/06* (2006.01)
  *D04C 1/06* (2006.01)
  *D01D 5/20* (2006.01)
  *A61B 17/00* (2006.01)

(52) U.S. Cl.
  CPC .............. *D04C 1/06* (2013.01); *D06M 10/001* (2013.01); *A61B 2017/00526* (2013.01); *A61B 2017/0619* (2013.01); *D01D 5/20* (2013.01); *D10B 2509/04* (2013.01)

(58) Field of Classification Search
  CPC ........ D10B 2509/04; D01D 5/20; D01D 5/00; H01B 13/14
  See application file for complete search history.

(56) References Cited

U.S. PATENT DOCUMENTS

| | | |
|---|---|---|
| 6,991,636 B2 | 1/2006 | Rose |
| 7,029,490 B2 | 4/2006 | Grafton et al. |
| 7,892,256 B2 | 2/2011 | Grafton et al. |
| 8,088,146 B2 | 1/2012 | Wert et al. |
| 8,298,284 B2 | 10/2012 | Cassani |
| 9,801,707 B2 | 10/2017 | Cassani |
| 10,188,504 B2 | 1/2019 | Cassani |
| 10,323,342 B1 | 6/2019 | Callison et al. |
| 10,385,488 B1 | 8/2019 | Monllor et al. |
| 10,820,901 B2 | 11/2020 | Callison et al. |
| 11,202,625 B2 | 12/2021 | Monllor et al. |
| 2005/0192631 A1* | 9/2005 | Grafton ............ A61B 17/06166 606/228 |
| 2008/0248079 A1 | 10/2008 | Dempsey et al. |
| 2011/0264057 A1 | 10/2011 | Eversull et al. |
| 2013/0261662 A1 | 10/2013 | Mayer et al. |
| 2014/0343580 A1 | 11/2014 | Priewe |
| 2016/0144066 A1 | 5/2016 | Long et al. |

FOREIGN PATENT DOCUMENTS

| | | |
|---|---|---|
| WO | 2015/171962 | * 11/2015 |
| WO | WO 2015/171962 | 11/2015 |
| WO | WO 2018/017945 | 1/2018 |

OTHER PUBLICATIONS

PermaTape Suture; retrieved Jun. 8, 2022.
Healix Advance Anchors with Permatape Suture; MITEK Sports Medicine; retrieved Jun. 8, 2022.
Kirsh; "Teleflex Medical launches new suture technology to reduce tissue strangulation;" Medical Design & Outsourcing; Jan. 10, 2018; retrieved Jun. 8, 2022.
*BoneZone*, Teleflex Medical OEM Announces New Suture Technology; Nov. 13, 2017; retrieved Jun. 8, 2022.
Force Fiber; Sutures and Braids; Teleflex Medical OEM; retrieved Jun. 8, 2022.
Specialized Sutures, Braids, Fibers, Yarns, and Resins; Teleflex Medical OEM; retrieved Jun. 8, 2022.

* cited by examiner

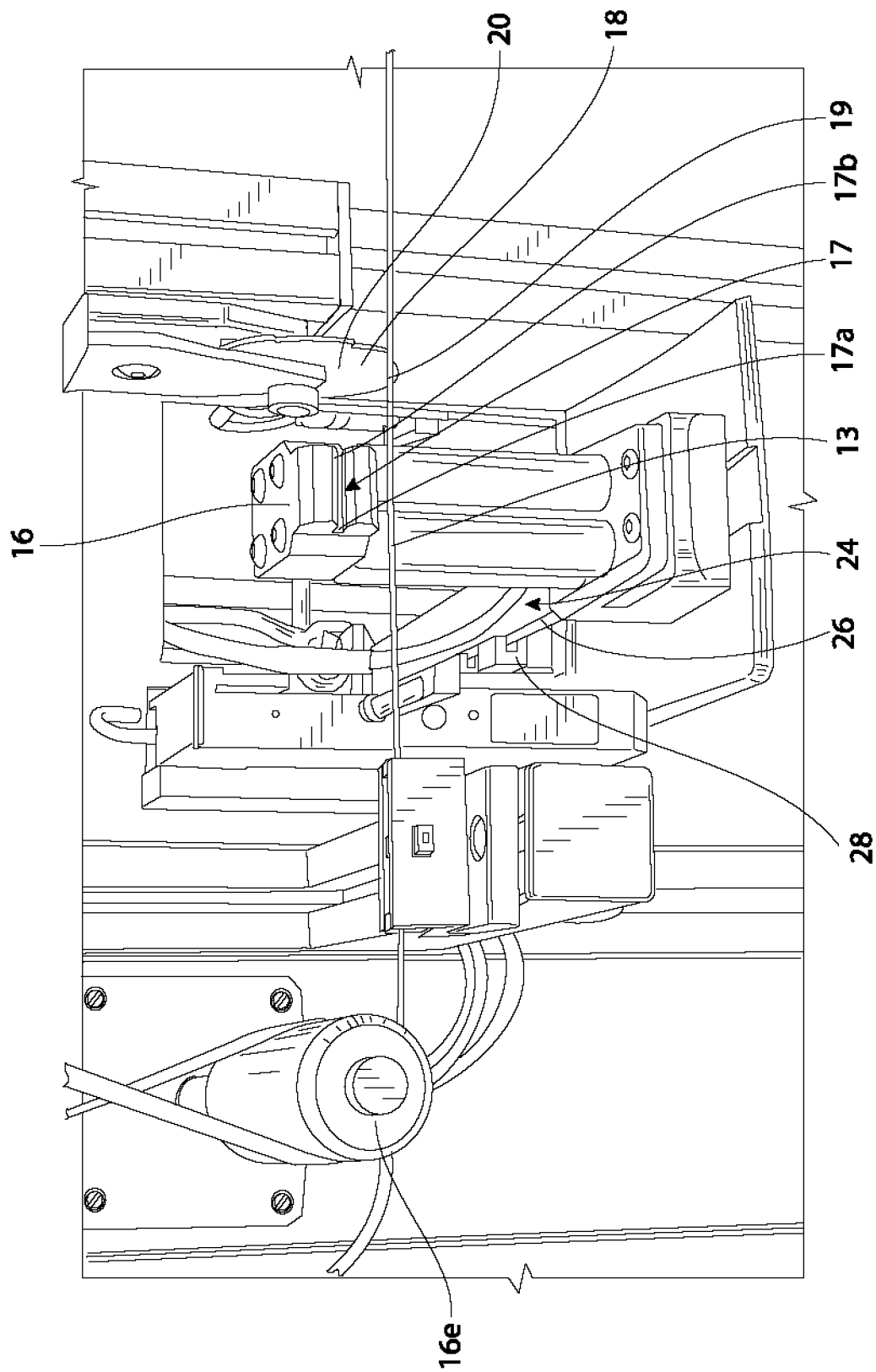

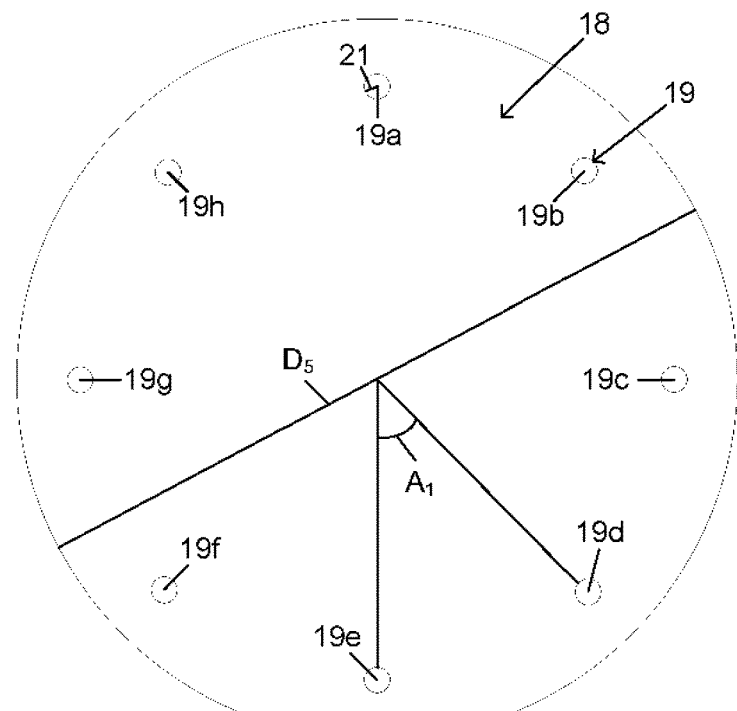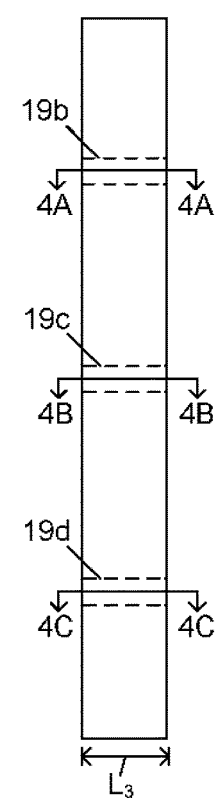
Figure 3A Figure 3B
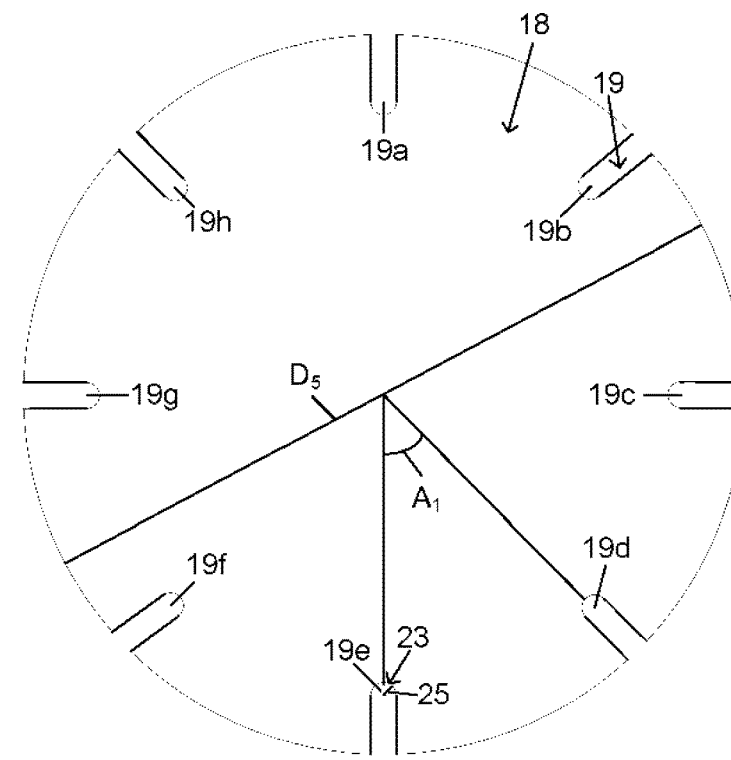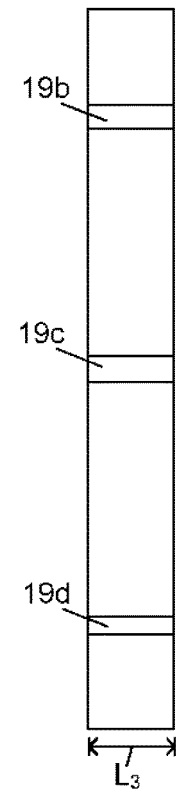
Figure 3C Figure 3D

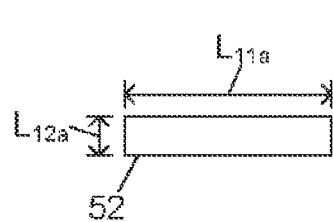
Figure 10A$_1$
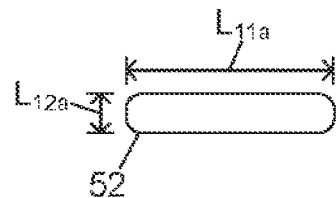
Figure 10A$_2$
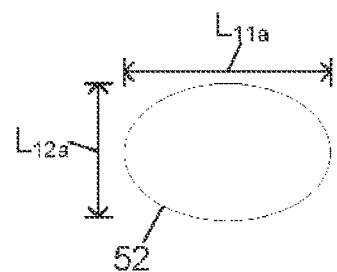
Figure 10A$_3$
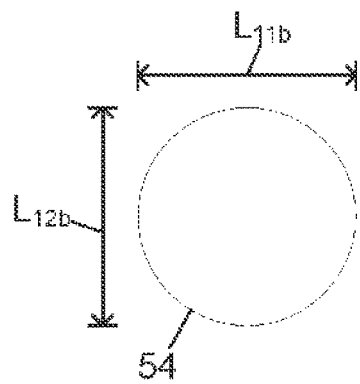
Figure 10B$_1$
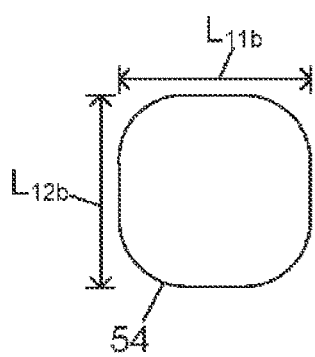
Figure 10B$_2$
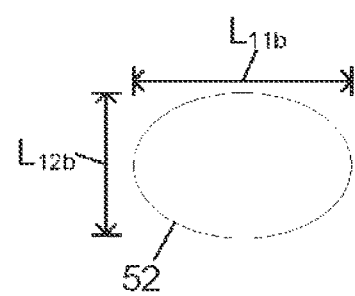
Figure 10B$_3$
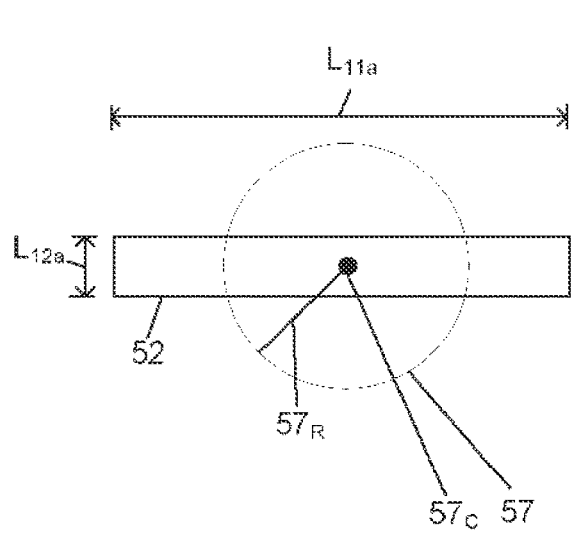
Figure 11A
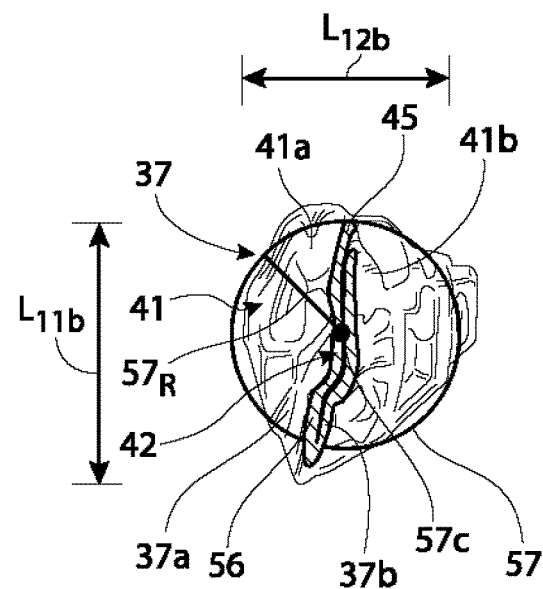
Figure 11B

PROCESS OF CHANGING CROSS SECTIONAL SHAPE WITHIN A TEXTILE

CROSS-REFERENCE TO RELATED APPLICATIONS

This application is a continuation-in-part application of International Application No. PCT/US2017/043268, filed Jul. 21, 2017, which claims priority to U.S. Provisional Application No. 62/365,467, filed Jul. 22, 2016, both of which are incorporated by reference herein in their entireties for all purposes.

BACKGROUND

Currently certain textiles are formed using complicated machines that make textiles into their final shape. These machines tend to be very expensive and tend to have slow production rates. The orthopedic high strength suture market is evolving and flat sutures are becoming more preferable to conventional round sutures. The flat cross-sectional shape of newer suture designs is better at distributing stress over the anatomy without causing pull through. Pull through is when a suture has such a high load applied through it that it cuts through the tissue that it is holding. However, it is preferred that flat sutures have round or elliptical cross sections at the ends of the structure for ease of use of current suture passer technology and entry into the anatomy, among other purposes. The rounded ends of the suture allow the suture to be integrated into the suture passer instrumentation that is used to deliver the suture into the anatomy. The following disclosure proposes a method for forming a second cross-sectional shape into a portion of a suture or textile having a first cross-sectional shape, for example, forming round segments at the end of or in portions of the length of a flat polymer based textile.

SUMMARY

Textiles having multiple cross-sectional sizes and/or shapes are disclosed.

Textile shapers that can change one or more portions of a textile from a textile first cross-sectional shape to one or multiple other cross-sectional shapes are disclosed.

Methods of making textiles having multiple cross-sectional sizes and/or shapes are disclosed. Changing the size and/or shape of textiles with heat, without heat, or both are disclosed.

Textile shapers are disclosed. For example, a textile shaper is disclosed having a textile having a textile first cross-sectional shape and a textile second cross-sectional shape. The textile shaper can have a heater. The textile shaper can have a die. The textile can be moveable through the heater and the die. When the textile is in the heater, the textile can have the textile first cross-sectional shape. When the textile is in the die, the textile can have the textile second cross-sectional shape.

The textile can be a braided textile suture.

The textile first cross-sectional shape can be a flat shape.

The textile second cross-sectional shape can be a non-flat shape.

When the textile is between the heater and the die, the textile can have a textile third cross-sectional shape.

The textile third cross-sectional shape can be defined by a fold in the textile.

The textile third cross-sectional shape can be a taco-shape.

A segment of textile can be moveable through the heater and the die. The segment can have a segment first portion, a segment second portion, and a segment third portion. When the segment is proximal to the heater and the die, the segment first, second, and third portions can have the textile first cross-sectional shape. When the segment is distal to the heater and the die, the segment first portion can have the textile first cross-sectional shape, the segment second portion can have the textile third cross-sectional shape, and the segment third portion can have the textile second cross-sectional shape.

The segment second portion can be between the segment first and third segment portions.

When the segment first portion is in the die, the segment first portion can be at a first temperature. When the segment third portion is in the die, the segment third portion can be at a second temperature. The second temperature can be greater than the first temperature.

When the segment third portion is in the heater, the segment third portion can be heatable from the first temperature to the second temperature.

When the segment second portion is in the die, the segment second portion can be at the first temperature.

The textile first cross-sectional shape can have a first shape center, a first shape first side, and a first shape second side. The first shape center and the first shape first side can be separated by a first shape first dimension along a first axis. The first shape center and the first shape second side can be separated by a first shape second dimension along a second axis. The first shape first dimension can be greater than the first shape second dimension. The textile second cross-sectional shape can have a second shape center, a second shape first side, and a second shape second side. The second shape center and the second shape first side can be separated by a second shape first dimension along the first axis. The second shape center and the second shape second side can be separated by a second shape second dimension along the second axis. The first shape first dimension can be greater than the second shape first dimension.

The first axis can be perpendicular to the second axis.

The first shape second dimension can be less than the second shape second dimension.

The textile can have a cross-sectional center, a cross-sectional first side, and a cross-sectional second side when the textile is in the textile first cross-sectional shape and when the textile is in textile second cross-sectional shape. The cross-sectional first side can be farther from the cross-sectional center when the textile is in the textile first cross-sectional shape than when the textile is in the textile second cross-sectional shape.

The cross-sectional second side can be closer to the cross-sectional center when the textile is in the textile first cross-sectional shape than when the textile is in the textile second cross-sectional shape.

The textile first cross-sectional shape can have a first shape area. The textile second cross-sectional shape can have a second shape area. When the textile first and second cross-sectional shapes are overlaid onto a reference shape, less of the first shape area can fit inside the reference shape than the second shape area.

The reference shape can have a reference shape area. The reference shape area can be equal to the first shape area.

The reference shape can be a circle.

Textile shapers are disclosed. For example, a textile shaper is disclosed having a textile first portion and a textile second portion. The textile shaper can have a heater. The textile shaper can have a die. The textile can be moveable through the heater and the die. When the textile first portion is in the die, the textile first portion can be at a first temperature. When the textile second portion is in the die, the textile second portion can be at a second temperature. The second temperature can be greater than the first temperature. When the textile first and second portions are proximal to the heater and the die, the textile first and second portions can have a textile first cross-sectional shape. When the textile first and second portions are distal to the heater and the die, the textile first portion can have the textile first cross-sectional shape and the textile second portion can have a textile second cross-sectional shape.

The textile can be a braided textile suture.

The textile first cross-sectional shape can be a flat shape.

The textile second cross-sectional shape is a non-flat shape.

The textile can have a cross-sectional perimeter having a perimeter segment. When the textile has the textile first cross-sectional shape, the perimeter segment can be straight. When the textile has the textile second cross-sectional shape, the perimeter segment can be curved.

The textile can have a cross-sectional perimeter having a perimeter segment. When the textile has the textile first cross-sectional shape, the perimeter segment can have a first radius of curvature. When the textile has the textile second cross-sectional shape, the perimeter segment can have a second radius of curvature. The second radius of curvature can be less than the first radius of curvature.

The textile can have a textile third portion. When the textile first, second, and third portions are distal to the heater and the die, the textile third portion can have a textile third cross-sectional shape.

The textile third cross-sectional shape can be a folded shape.

The textile third portion can be between the textile first and second portions.

Methods for making a braided textile sutures are disclosed. For example, a method is disclosed that can include pulling a braided textile through a heater. The method can include heating alternating portions of the braided textile via the heater from a textile first temperature to a textile second temperature greater than the textile first temperature. The method can include pulling heated portions and non-heated portions of the braided textile through a die. The method can include changing a cross-sectional shape of the heated portions from a textile first cross-sectional shape to a textile second cross-sectional shape when the heated portions are pulled through the die.

The textile first cross-sectional shape can be a flat shape.

The textile second cross-sectional shape can be a non-flat shape.

The method can include sizing the textile to create a braided suture having a suture first portion and a suture second portion. The suture first portion can have the textile first cross-sectional shape. The suture second portion can have the textile second cross-sectional shape.

The braided suture can have a suture third portion. The suture third portion can have a textile third cross-sectional shape.

The textile third cross-sectional shape can be a folded shape.

The suture third portion can be between the suture first and second portions.

BRIEF DESCRIPTION OF THE DRAWINGS

FIG. 1B illustrates a magnified perspective view of the textile shaper of FIG. 1A.

FIG. 3A illustrates a front view of a variation of a die.

FIG. 3B illustrates a side view of the die of FIG. 3A.

FIG. 3C illustrates a front view of a variation of a die.

FIG. 3D illustrates a side view of the die of FIG. 3C.

Figure 5A:
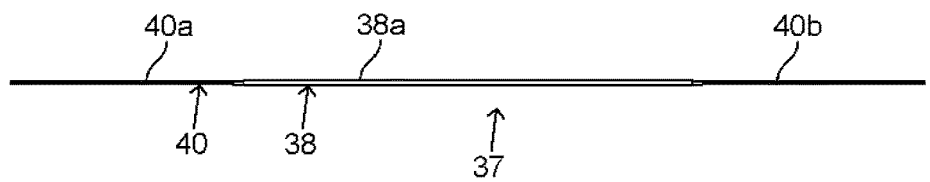
FIG. 5A illustrates a side view of a variation of a suture.
Figure 5B:
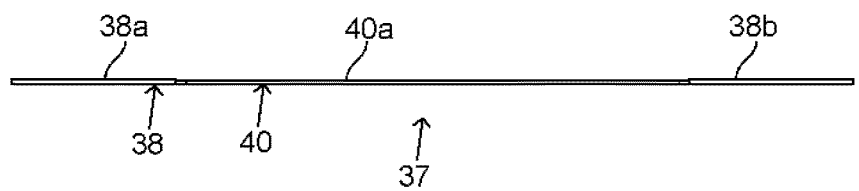
FIG. 5B illustrates a side view of a variation of a suture.
Figure 5C:
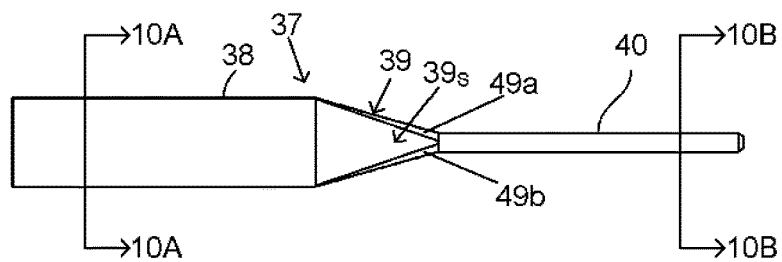
FIG. 5C illustrates a side view of a variation of a suture.

FIG. $10A_1$ illustrates a variation of a cross-section of the suture of FIG. 5C taken along line 10A-10A.

FIG. $10A_2$ illustrates a variation of a cross-section of the suture of FIG. 5C taken along line 10A-10A.

FIG. $10A_3$ illustrates a variation of a cross-section of the suture of FIG. 5C taken along line 10A-10A.

FIG. $10B_1$ illustrates a variation of a cross-section of the suture of FIG. 5C taken along line 10B-10B.

FIG. $10B_2$ illustrates a variation of a cross-section of the suture of FIG. 5C taken along line 10B-10B.

FIG. $10B_3$ illustrates a variation of a cross-section of the suture of FIG. 5C taken along line 10B-10B.

FIG. 11A illustrates a variation of a textile shape and a reference shape.

FIG. 11B illustrates a variation of a textile shape and a reference shape.

Figure 12A:
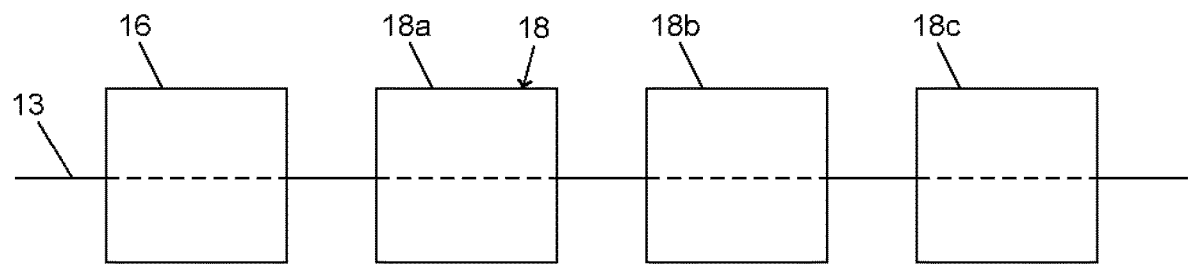

FIG. 12A illustrates a variation of a suture shaper.

Figure 12B:
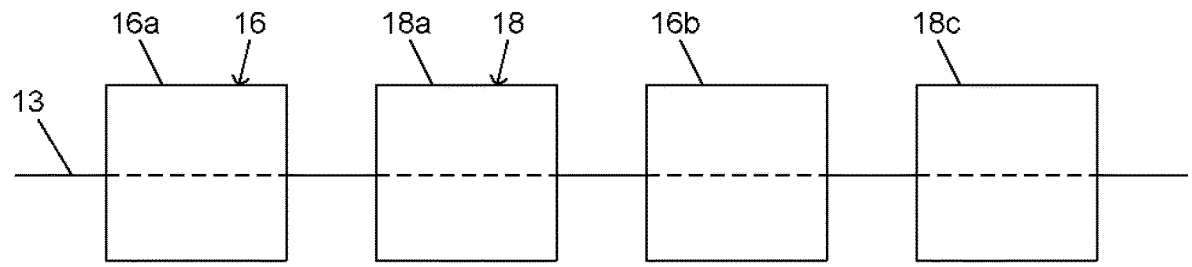

FIG. 12B illustrates a variation of a suture shaper.

Figure 1A:
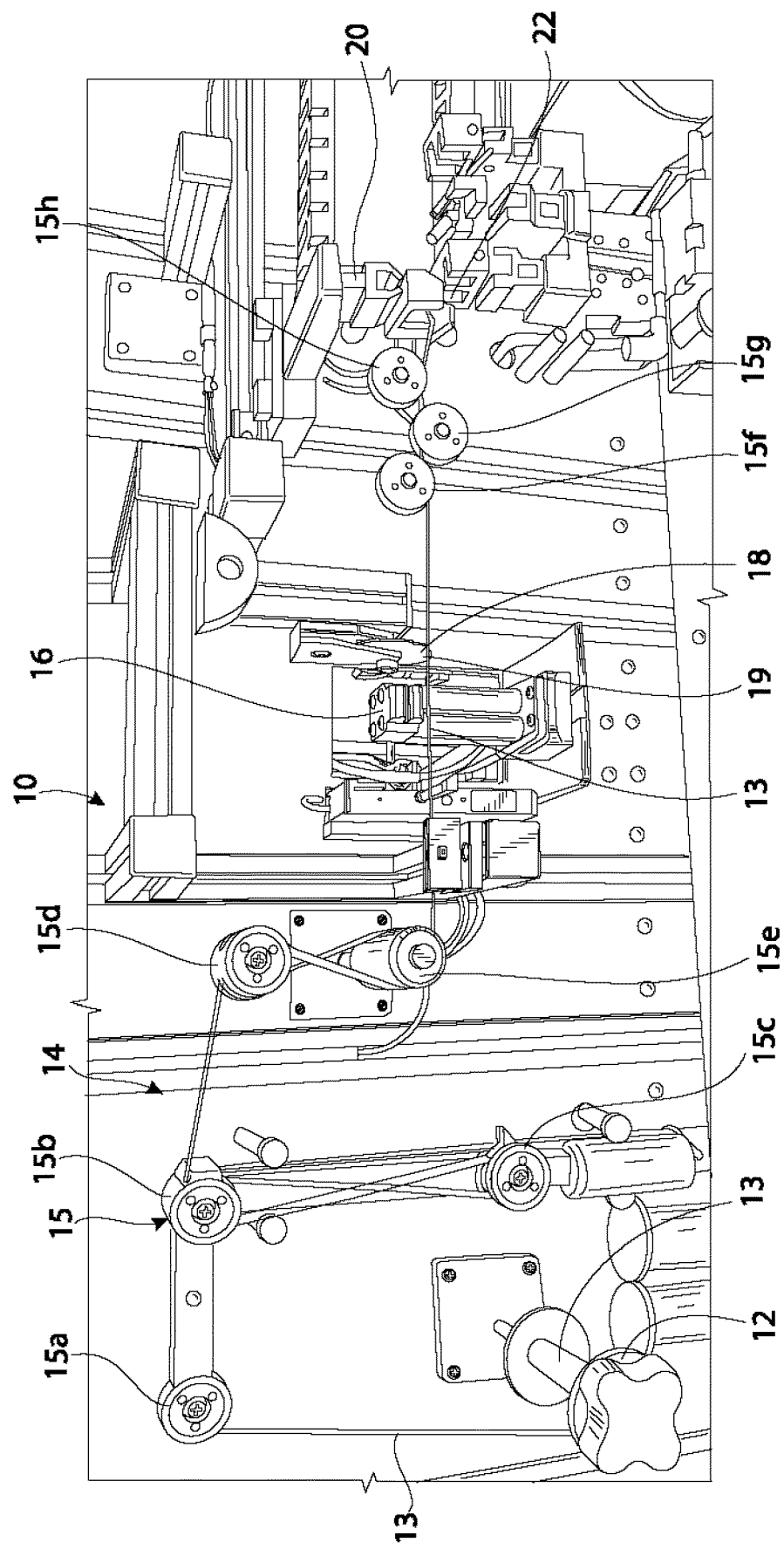
FIG. 1A illustrates a perspective view of a variation of a textile shaper.
Figure 13:
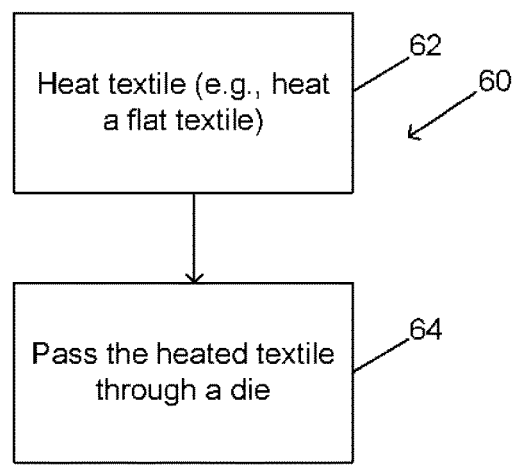

FIG. 13 illustrates a variation of a method undertaken by the textile shaper of FIG. 1A.

FIG. 14: Round/flat/round suture structure. Both of the ends on the suture have been rounded using the processing techniques described herein.

FIG. 15: Flat/round/flat suture structure. This figure shows a suture having a round cross section within the length of a discrete suture length.

FIG. 16: Top view of an exemplary machine used to make discrete lengths of flat suture with round ends.

FIG. 17: Side view of an exemplary machine used to make discrete lengths of flat suture with round ends.

FIG. 18: Isometric view of an exemplary machine used to make discrete lengths of flat suture with round ends. This view shows the rotating gripper found within the ring structure.

FIG. 19: View of hot compression die. This die will be heated and compression applied between the two die component halves to shape the textile.

FIG. 20: View of textile with helical formed shape on end of a discrete length. The center shaft is a sacrificial mandrel that will be removed after shaping has completed.

FIG. 21: Compression roller forming dies. These dies can be heated and used to compress the textile into the shape of the dies.

FIG. 22: A suture having a textile shape that is created by only using isolated axial tension. The cross-sectional shape of the structure is C shaped and becomes more round under higher tension loads.

FIG. 23: Isometric view of the suture of FIG. 22.

FIG. 24: A clam shell design of a hot-compression rigid die. The entrance side of the die is the current shape of the textile.

FIG. 25: A view of a hot compression die showing shape of the output side feature is the intended shape of textile after processing. The die shown would create a width rolled circular cross-sectional shape.

FIG. 26: Highly drawn flat to round textile.

FIG. 27: Isometric view of a helical flat textile shaped structure formed by using a sacrificial shaping mandrel during processing.

FIG. 28: Isometric view of a curved die. It is envisioned that a heated textile could be ran over this type of surface to create a curved product.

FIG. 29: Side view of the curved die of FIG. 28.

FIG. 30: Textile having a shape that would be created by using the type of curved former found in FIG. 28 and FIG. 29.

FIG. 31: Textile having a shape that is other than round. This shape would be very stiff in the vertical axis. This type of forming is capable of creating a fabric that has anisotropic properties.

FIG. 32: Isometric view of a flat braided textile having button holes formed into it. The shaping needle is inserted into the braided structure while at ambient temperature. After insertion, the shaping needle is heated to a temperature that changes the crystallinity of the polymer and the hole remains within the braided structure after removal of the needle.

FIG. 33: Isometric view of a flat braided textile with a button hole created using the technique also used to create FIG. 32.

DETAILED DESCRIPTION

A textile having multiple cross-sectional sizes and/or shapes is disclosed. For example, a textile having a textile first cross-sectional size and/or shape and a textile second-cross sectional size and/or shape is disclosed. The perimeter of the first cross-sectional shape can have one or more straight portions, one or more curved portions, or both. The textile first cross-sectional shape can be a regular or an irregular shape. The textile second cross-sectional shape can be a regular or an irregular shape. The textile first cross-sectional size and/or shape can be the same as or different from the textile second cross-sectional and/or shape. The textile first cross-sectional size and/or shape can be changed to the textile second cross-sectional size and/or shape. About 2% to about 95% of the area of the first cross-sectional shape can fit inside a reference shape (e.g., reference circle) having the same cross-sectional area as the first cross-sectional shape. The cross-sectional area of the reference circle is also referred to as the reference circle cross-sectional area. About 50% to about 100% of the area of the second cross-sectional shape can fit inside the reference circle cross-sectional area. More of the second cross-sectional shape can fit inside the reference circle than the first cross-sectional shape, for example, about 2% to about 98% more.

A textile shaper that can change one or more portions of a textile from the textile first cross-sectional shape to one or multiple other cross-sectional shapes (e.g., to the textile second cross-sectional shape) is disclosed. The textile shaper can have a heater and a die. The heater and the die can be separate from one another, removably attachable to one another, or integrated with one another.

A method of making a textile having multiple cross-sectional sizes and/or shapes is disclosed. For example, a method of making a textile having a textile first cross-sectional shape and a textile second-cross sectional shape is disclosed. The method can include temporarily and/or permanently changing the textile first cross-sectional size and/or shape to the textile second cross-sectional size and/or shape along one or more portions of the textile, including, for example, along the entire length of the textile or any lesser length. The textile first cross-sectional shape can be non-round and the textile second cross-sectional shape can be round. The textile first cross-sectional shape can be non-rounded and the textile second cross-sectional shape can be rounded.

System and Apparatus

FIG. 1A illustrates a textile shaper 10 (also referred to as a tipping machine) having a textile source 12, a textile control system 14, a heater 16, a die 18, and a textile mover 20.

The textile source 12 can include one or multiple textiles 13, for example, 1 to 10 or more textiles 13 (e.g., 1 textile, 2 textiles, 3 textiles). The textile source 12 can be a textile holder such as a bin, a spool, or both. The textiles 13 can be in or on the textile source 12. Each textile source 12 can include a single segment of textile 13 or multiple segments of textile 13. Each textile segment can have a textile input length, where the textile input length can be the length of the textile 13 when the textile 13 is initially loaded or moved into the textile shaper 10 (e.g., after braiding, after being braided). The textile input length can be non-sized (also referred to as uncut) as shown in FIG. 1A, or can be pre-sized (also referred to as precut). The non-sized textile input length can be from about 5 meters to about 500 meters or more, including every 1 meter increment within this range (e.g., 5 m, 50 m, 100 m, 200 m, 500 m). The pre-sized textile input length can be from about 10 cm to about 500 cm, including every 1 cm increment within this range (e.g., 10 cm, 25 cm, 50 cm, 75 cm, 100 cm, 200 cm, 500 cm). The pre-sized textile input length can be the textile target length or can be about 1% to about 25% greater than the textile target length, including every 1% increment within this range (e.g., 1%, 5%, 10%, 25%). Pre-sized textile segments can be in a bin for processing, can be linked together end-to-end (e.g., with or without connectors), or both.

The textile 13 can be a non-braided textile (e.g., a weaved textile), a braided textile, or both. For example, the textile 13 can have a braided portion and a non-braided portion. The textile 13 can be a suture having a first end and a second end. The textile can be a flat suture tape. The textile 13 (e.g., braided suture) can be made of yarn, such as natural materials such as silk and cotton, synthetic materials such as polymers, for example polyethylene, polyethylene terephthalate (PET), ultra high molecular weight polyethylene (UHMWPE), polytetrafluoroethylene (PTFE), or other biocompatible polymer, biologically incompatible yarn such as cotton, metal (e.g., gold, platinum, nickel, tin, nitinol, cobalt, chromium, stainless steel), polyester, nitinol, polypropylene, or combinations thereof.

The textile control system 14 can position the textile 13, tension the textile 13, or both. The textile control system 14 can position and/or tension the textile 13 for interaction with the heater 16 and/or the die 18. The textile control system 14 can include one or multiple textile controllers 15, for example, 1 to 20 or more textile controllers 15, including every 1 textile controller 15 in this range (e.g., first through eighth textile controllers 15a-15h).

For example, one or multiple of the textile controllers 15 (e.g., 1 to all of the textile controllers 15) can position the textile 13 to a desired position prior to heating the textile 13 (e.g., via the heater 16), while heating the textile 13 (e.g., via the heater 16), after heating the textile 13 (e.g., via the heater 16), or any combination thereof. The textile controllers 15 can position the textile 13 into a pre-heat position, a to-be-heated position, a post-heat position, or any combination thereof.

As another example, one or multiple of the textile controllers 15 (e.g., 1 to all of the textile controllers 15) can tension the textile 13 to a desired tension prior to heating the textile 13 (e.g., via the heater 16), while heating the textile 13 (e.g., via the heater 16), after heating the textile 13 (e.g., via the heater 16), or any combination thereof. The textile controllers 15 can tension the textile 13 into a pre-heat tension, a to-be-heated tension, a post-heat tension, or any combination thereof. The pre-heat tension, to-be-heated tension, and post-heat tension can be the same or different from one another.

As yet another example, each of the textile controllers 15 can position and/or tension the textile 13 to a desired position and/or tension prior to heating the textile 13 (e.g., via the heater 16), while heating the textile 13 (e.g., via the heater 16), after heating the textile 13 (e.g., via the heater 16), or any combination thereof.

The textile controllers 15 can be fixed or moveable, for example, relative to the textile source 12, relative to the heater 16, relative to the die 18, or relative to any combination thereof. The textile controllers 15 can have 1 to 6 degrees of freedom, including every 1 degree of freedom increment within this range. For example, the textile controllers 15 can be translatable along 1, 2, or 3 translation axes. The translation axes can be mutually perpendicular to one another. As another example, the textile controllers can be rotated about 1, 2, or 3 rotation axes. The rotation axes can be mutually perpendicular with one another. As yet another example, the textile controllers 15 can be translated and/or rotated about each of 1, 2, or 3 movement axes. The movement axes can be mutually perpendicular with one another. The textile controllers 15 can be fixed or moveable spindles.

The textile controllers 15 can change the tension of the textile 13 from a first textile tension to a second textile tension. The first tension can be the tension of the textile 13 while on or in the textile source 12. The second tension can be the tension of the textile 13 while in any of the components of the textile shaper 10 (e.g., while in the heater 16, while in the die 18, or both), and/or while between any two components of the textile shaper 10 (e.g., between two of the textile controllers 15, between a controller 15 and the heater 16, between a controller 15 and the die 18, between the heater 16 and the die 18, or any combination thereof). The first textile tension can be about 0 Newtons to about 10 Newtons and the second tension can be about 1 Newton to about 20 Newtons, including every 1 Newton increment within these ranges.

The positions (e.g., heights) of the textile controllers 15 can be sensed by a processor to control movement of the textile 13.

The textile control system 14 can be upstream of the heater 16, downstream of the heater 16, upstream of the die 18, downstream of the die 18, or any combination thereof. For example, one or more of the textile controllers 15 can be can be upstream of the heater 16, downstream of the heater 16, upstream of the die 18, downstream of the die 18, or any combination thereof. FIG. 1A illustrates that the first through fifth textile controllers 15a-15e can be upstream of the heater 16 and upstream of the die 18. FIG. 1A further illustrates that the sixth through eighth textile controllers 15f-15h can be downstream of the heater 16 and downstream of the die 18.

The heater 16 can heat the textile 13, for example, from a first temperature to a second temperature (also referred to as the heated temperature). The first temperature can be about 10 degrees Celsius to about 200 degrees Celsius, including every 1 degree Celsius increment within this range (e.g., 40 degrees Celsius, 100 degrees Celsius). The first temperature can be about 15 degrees Celsius to about 50 degrees Celsius, including every 1 degree Celsius increment within this range (e.g., 40 degrees Celsius). The second temperature can be about 20 degrees Celsius to about 300 degrees Celsius, including every 1 degree Celsius increment within these ranges (e.g., 100 degrees Celsius, 120 degrees Celsius). The second temperature can be about 80 degrees Celsius to about 200 degrees Celsius, or more narrowly about 80 degrees Celsius to about 150 degrees Celsius, including every 1 degree Celsius increment within these ranges (e.g., 100 degrees Celsius, 120 degrees Celsius). The first temperature can be less than the second temperature. The heater 16 can be a non-contact heater (e.g., infrared heater). For example, to heat the textile 13, the heater 16 can emit energy (e.g., radiation, infrared radiation). The heater 16 can emit energy toward the textile 13, toward a reflective surface, or both. The reflective surface can redirect energy emitted from the heater 16 toward a heating chamber, toward the textile 13, toward another reflective surface, or any combination thereof. As another example, the heater 16 can be a contact heater. As yet another example, the heater 16 can have a non-contact heater portion and a contact heater portion. The non-contact heater portion can be integrated with or attached to the contact heater portion, or can be separate from the contact heater portion (e.g., separated by a dimension such as 1 cm to 50 cm or more). The heater 16 can be turned on and off. When the heater 16 is on, the heater 16 can emit energy toward the textile 13. When the heater 16 is off, the heater 16 can be configured to not emit energy toward the textile 13. When the heater 16 is off, some or no energy can be emitted from the heater 16.

The textile 13 can be movable through the heater 16, the heater 16 can be movable over the textile 13, or both. For example, the textile 13 can be moved through the heater 16 (e.g., pulled through the heater 16) when the heater 16 is in a fixed position. As another example, the heater 16 can be moved over the textile 13 (e.g., pushed or pulled over the textile 13) when the textile 13 is in a fixed position, for example, when the heater 16 is on or off. As yet another example, the textile 13 can be moved through the heater 16 (e.g., pulled through the heater 16) and the heater 16 can be moved over the textile 13 (e.g., pushed or pulled over the textile 13).

The textile 13 and the heater 16 can move in the same direction or in opposite directions. The textile 13 and the heater 16 can move in a first direction, in a second direction opposite the first direction, or both. The first direction can be along a textile longitudinal axis, for example, toward the die 18. The second direction can be along the textile longitudinal axis, for example, away from the die 18. The textile longitudinal axis can be straight and/or curved. For example, a textile first portion can have a straight textile longitudinal axis and a textile second portion can have a curved textile longitudinal axis.

When the textile and the heater 13, 16 both move, they can move sequentially or simultaneously, in the same or different directions. When the textile and the heater 13, 16 move simultaneously, for example, in the same direction (e.g., the first direction), the textile 13 can move at slower rate, at the same rate, or at a faster rate than the heater 16, or vice versa. When the textile and the heater 13, 16 move simultaneously, for example, in opposite directions (e.g., the textile 13 in the first direction and the heater 16 in the second direction), the textile 13 can move at slower rate, at the same rate, or at a faster rate than the heater 16, or vice versa. The textile 13 can be moved through the heater 16 when the heater 16 is on (i.e., emitting energy), when the heater 16 is off (i.e., not emitting energy), or when the heater 16 is on and when the heater 16 is off. The heater 16 can be moved over the textile 13 when the heater 16 is on, when the heater 16 is off, or both.

The heater 16 can heat one or more portions of the textile 13 (e.g., 1-25,000 or more portions for a non-sized textile 13, or 1-25,000 or more portions for a pre-sized textile 13, including every 1 portion increment within these ranges). The heater 16 can heat one or more portions of the textile 13 (e.g., 1-5,000 or more portions for a non-sized textile 13, or 1-5,000 or more portions for a pre-sized textile 13, including every 1 portion increment within these ranges). One or multiple heated portions (e.g., 1 to 10 or more heated portions, for example, 1 heated portion, 2 heated portions, 3 heated portions) can be downstream of the heater 16, for example, before the textile 13 is sized (e.g., cut) to a target length. The textile 13 can be alternately heated and not heated (e.g., via the heater 16) along the textile longitudinal axis as the textile 13 is moved through the shaper 10. The heated portions can alternate with the non-heated portions. Before a distal end of the textile 13 (also referred to as the textile distal end) is sized to a target length, a non-heated portion can be between two adjacent heated portions. Before the textile distal end is sized to a target length, the textile distal end can be a heated portion. Before the textile is sized to a target length, the textile distal end can be a non-heated portion. A non-heated portion can be between each heated portion, for example, as the textile 13 is processed through the shaper 10 after the heater 16. The heater 16 can alternately heat and not heat the textile 13 along the textile longitudinal axis such that the non-heated and heated portions can alternate with one another along a length of the textile 13 (e.g., along a textile longitudinal axis). The heated portions can have a heated portion length. The non-heated portions can have a non-heated portion length. The heated portion lengths can be the same as or different from the non-heated portion lengths.

The die 18 can temporarily and/or permanently change the cross-sectional size and/or shape of one or multiple portions of the textile 13, for example, from a textile first cross-sectional size and/or shape to a textile second cross-sectional size and/or shape. The die 18 can have one or multiple holes 19 (also referred to as die holes and channels) through which the textile 13 can pass through. For example, the die 18 can have 1 to 10 or more holes 19, including every 1 hole 19 increment within this range (e.g., 1 hole, 2 holes, 10 holes). The die holes 19 can change the cross-sectional size and/or shape of the textile 13 as the textile is moved through a die hole 19. The textile 13 can be translated (e.g., pulled) through one or multiple die holes 19 (e.g., sequentially), and/or the die 18 can be translated (e.g., pulled or pushed) over the textile 13 while the textile 13 is in a die hole 19.

The die hole 19 can have a constant size. The die hole 19 can be tapered, non-tapered, or both. For example, the die hole 19 can have a tapered portion and a non-tapered portion. The die hole 19 can have an entrance and an exit. The die hole entrance size and/or shape can be the same as or different from the die exit size and/or shape. The die hole 19 can taper from a first size and/or shape to second size and/or shape, where the second can size and/or shape can be larger than the first size and/or shape. The die hole 19 can taper from a first size and/or shape to second size and/or shape, where the second can size and/or shape can be smaller than the first size and/or shape. The die hole 19 can have one or multiple tapers. The die hole 19 can have one or multiple tapered portions. A single hole 19 can be tapered. As another example, multiple dies 18 (e.g., 1-10 dies such as 2 dies 18, 3 dies 18) can be stacked against each other with the holes 19 aligned to create tapered die hole 19, where each die hole has a constant or tapered die hole 19. The entrance edge of the die hole 19 can be beveled or rounded to inhibit or prevent the die 18 from shaving off pieces of the textile 13, from cutting pieces of the textile 13, from fraying the textile 13, or any combination thereof, for example, as the textile 13 is moved through the die hole 19. The entrance edge of the die hole 19 can be non-beveled or non-rounded so that the die 18 can shave off pieces of the textile 13, can cut pieces of the textile 13, or both, for example, as the textile 13 is moved through the die hole 19.

The textile 13 can be movable through the die 18, the die 18 can be movable over the textile 13, or both. For example, the textile 13 can be moved through the die 18 (e.g., pulled through the die 18) when the die 18 is in a fixed position. As another example, the die 18 can be moved over the textile 13 (e.g., pushed or pulled over the textile 13) when the textile 13 is in a fixed position. As yet another example, the textile 13 can be moved through the die 18 (e.g., pulled through the die 18) and the die 18 can be moved over the textile 13 (e.g., pushed or pulled over the textile 13).

The textile 13 and the die 18 can move in the same direction or in opposite directions. The textile 13 and the die 18 can move in a first direction, in a second direction opposite the first direction, or both. The first direction can be along a textile longitudinal axis, for example, toward the die

18. The second direction can along the textile longitudinal axis, for example, away from the die 18.

When the textile and the die 13, 18 both move, they can move sequentially or simultaneously, in the same or different directions. When the textile and the die 13, 18 move simultaneously, for example, in the same direction (e.g., the first direction), the textile 13 can move at slower rate, at the same rate, or at a faster rate than the die 18, or vice versa. When the textile and the die 13, 18 move simultaneously, for example, in opposite directions (e.g., the textile 13 in the first direction and the die 18 in the second direction), the textile 13 can move at slower rate, at the same rate, or at a faster rate than the die 18, or vice versa. The textile 13 can be moved through the die 18 when the heater 16 is on (i.e., emitting energy), when the heater 16 is off (i.e., not emitting energy), or when the heater 16 is on and when the heater 16 is off.

When the textile 13 goes through a die hole 19 (e.g., by movement of the textile 13, by movement of the die 18, or by movement of both), the die 18 can temporarily or permanently change the cross-sectional size and/or shape of the textile 13. The entire length of the textile 13 (also referred to as the textile length, textile input length, textile first length) can be moved through one or multiple die holes 19 (e.g., sequentially or simultaneously), or one or multiple segments of the textile 13 (also referred to as textile segments) can be moved through one or multiple die holes 19 (e.g., sequentially and/or simultaneously). Each textile segment can have a segment length, where each segment length can be less than the textile length. The textile length can be the length of a non-sized textile 13 or a pre-sized textile 13. The die 18 can thereby temporarily or permanently change the cross-sectional size and/or shape of the textile 13, for example, along the entire textile 13 (i.e., along the textile length) or along one or multiple textile segments (i.e., along one or multiple segment lengths).

The die 18 can change the cross-sectional size and/or shape of the textile 13 from a textile first cross-sectional size and/or shape to a textile second cross-sectional size and/or shape. For example, the die 18 can change the cross-section of the textile 13 from a textile first cross-sectional size to a textile second cross-sectional size. As another example, the die 18 can change the cross-section of the textile 13 from a textile first cross-sectional shape to a textile second cross-sectional shape. As yet another example, the die 18 can change the cross-section of the textile 13 from a textile first cross-sectional size and shape to a textile second cross-sectional size and shape. The textile first cross-sectional size and be less than, equal to, or greater than the textile second cross-sectional size, or vice versa. The textile first cross-sectional shape can be the same as or different from the textile second cross-sectional shape, or vice versa. For example, where the textile second-cross sectional shape is different from the textile first cross-sectional shape, the size (e.g., perimeter, cross-sectional area, width, length, diameter, radius of curvature) of the textile second cross-sectional shape can be less than, equal to, or greater than the size (perimeter, cross-sectional area, width, length, diameter, radius of curvature) of the textile first cross-sectional shape.

The textile second cross-sectional shape can be the same as or similar to the cross-sectional shape of the die hole 19 (also referred to as the die hole cross-sectional shape). The textile second cross-sectional size can be the same as or similar to the die hole cross-sectional size. The size (e.g., perimeter, cross-sectional area, width, length, diameter, radius of curvature) of the textile second cross-sectional shape can be the same as or similar to the size (e.g., perimeter, cross-sectional area, width, length, diameter, radius of curvature) of the die hole cross-sectional shape.

Multiple die holes 19 can be used and/or one or multiple die holes 19 having a taper can be used. The textile 13 can pass through multiple die holes 19. The textile 13 can pass through one or multiple die holes having a taper. Using multiple die holes or using a die hole with a taper can allow the textile cross-sectional size and/or shape to be more gradually changed, for example, as compared to the use of a single die hole 19 or a non-tapered die hole 19. When multiple die holes are used, the multiple die holes can be on the same or a different die 18. Zero, one, or multiple die holes having a cross-sectional size and/or shape in between that of the die hole associated with the textile second cross-sectional shape can be used, for example, to gradually change (e.g., along a continuum) or step-wise change the textile cross-sectional size and/or shape. Zero, one, or multiple die holes having a tapered cross-sectional size and/or shape can be used, for example, to gradually or step-wise change the cross-sectional size and/or shape.

A gradual or step-wise change can advantageously control the deformation rate of the textile 13 (e.g., step-wise where two or more die holes 19 having a constant size are used, or continuously where a die hole 19 having a taper is used), which can, for example, enable the textile 13 to move or go through a die hole 19 more quickly without compromising the integrity of the textile 13 (e.g., at high speeds some of the heated textile may be shaved off by an edge of the die 18), without disrupting the deformation process (e.g., at high speeds the deformation may become less uniform as the textile 13 is forced into the die 18), or both.

When multiple die holes are used (e.g., on the same or a different die 18), there can be zero, one, or multiple textile intermediate cross-sectional shapes between the textile first and second cross-sectional shapes, for example, 0-10 or more textile intermediate cross-sectional shapes, including every 1 textile intermediate cross-sectional shape within this range (e.g., 0, 1, 2, 10 textile intermediate cross-sectional shapes), where each intermediate cross-sectional shape can be the same or similar shape as the die hole 19 associated with it. As another example, when multiple die holes are used (e.g., on the same or a different die 18), the multiple die holes 19 can have the same size and/or shape as each other.

As the textile 13 is moved or goes into a die hole 19, the textile cross-sectional size and/or shape (e.g., the textile first cross-sectional size and/or shape) can change so that the textile 13 can fit or squeeze into the die hole 19. To fit into a die hole 19, the textile 13 can deform, for example, fold, expand, contract, or any combination thereof. The textile 13 can fit into one or multiple die holes with or without folding. When the textile 13 becomes folded to fit into a die hole 19, the fold can be, for example, a C-shaped fold, a U-shaped fold, a V-shaped fold, an M-shaped fold, a W-shaped fold, an S-shaped fold, a Z-shaped fold, or an irregular shaped fold. As another example, with or without the textile 13 becoming folded to fit into a die hole 19, the textile 13 can contract and/or expand to fit into the die hole. For example, the textile 13 can contract along a cross-section first axis and/or along a cross-section second axis when the textile 13 is moved or goes into the die hole. As another example, the textile 13 can expand along the cross-section first axis and/or along the cross-section second axis when the textile 13 is moved or goes into the die hole. As yet another example, the textile 13 can expand along the cross-section first axis and contract along the cross-section second axis when the textile 13 is moved or goes into the die hole (e.g., for flat textiles 13 having a shape longer along the cross-section first axis than along the cross-section second axis such as oblong, elliptical, rectangular, stadium, and irregular shapes). The cross-section first and second axes can be perpendicular to one another. The cross-section first and second axes can be straight and/or curved. The cross-section first and second axes can be perpendicular or parallel to the textile longitudinal axis. For example, for a textile having a cross-sectional shape with a long axis and a short axis (e.g., oblong-, elliptical-, rectangular-, stadium-, and irregular-shaped cross-sections), the cross-sectional shape can contract along the long axis and expand along the short axis to fit into the die hole 19, with or without the textile 13 folding. For flat textiles, the long dimension along the long axis across the textile cross-sectional shape can be about 0.50 mm to about 15.00 mm larger than the short dimension along the short axis across the textile cross-sectional shape, including every 0.01 mm increment within this range. As another example, for flat textiles, the long dimension along the long axis can be about 25% to about 1000% larger than the short dimension along the short axis, including every 5% increment within this range. For flat textiles, the long dimension along the long axis across the textile cross-sectional shape can be about 1.0 mm to about 7.50 mm larger than the short dimension along the short axis across the textile cross-sectional shape, including every 0.01 mm increment within this range. As another example, for flat textiles, the long dimension along the long axis can be about 50% to about 500% larger than the short dimension along the short axis, including every 5% increment within this range.

The textile first cross-sectional shape can have a regular shape or an irregular shape. The textile first cross-sectional shape can have one or more straight edges, one or more curved edges, or both. The curved edges can define circular or non-circular arcs. The textile first cross-sectional shape can have one or more straight sides, one or more curved sides, or both. The curved sides can define circular or non-circular arcs. For example, the textile first cross-sectional shape can be a non-circular, non-elliptical, circular, elliptical, oblong, rectangular, stadium, or irregular shape. The textile first cross-sectional shape can be flat.

The textile first cross-sectional shape (e.g., a flat shape) can have a first shape first dimension along a first shape first axis and a first shape second dimension along a first shape second axis. The first shape first and second dimensions can be measured across the center of the textile first cross-sectional shape (also referred to as the textile first cross-sectional shape center). The textile first cross-sectional shape center can be the axial center of the textile first cross-sectional shape (e.g., a center point), can be the center of mass of the textile first cross-sectional shape (e.g., actual center of mass of the textile cross-section, or can assume a nominal mass unit of 1 is distribute evenly across the textile first cross-sectional shape), or can be a center region of the textile first cross-sectional shape (e.g., where the center region can have an area of about 0.1 mm² to about 2 mm², or more broadly, from about 0.05 mm² to about 10.0 mm², including every 0.1 mm² increment within these ranges).

The first shape first and second axes can be angled relative to one another, for example, from about 15 degrees to about 165 degrees, or more broadly, from about 5 degrees to about 175 degrees, including every 1 degree increment within these ranges (e.g., 5 degrees, 75 degrees, 90 degrees, 105 degrees, 175 degrees). The first shape first and second axes can be straight and/or curved.

The first shape first dimension can be greater than the first shape second dimension. For example, the first shape first dimension can be greater than the first shape second dimension by about 0.10 mm to about 15.00 mm, or more narrowly, by about 0.25 mm to about 7.50 mm, including every 0.01 mm increment within these ranges. As another example, the first shape first dimension can be greater than the first shape second dimension by about 0.5% to about 1000%, or more narrowly, by about 1% to about 500%, including every 5% increment within these ranges. The first shape first dimension can be measured across the widest portion of the textile first cross-sectional shape, the first shape second dimension can be measured across the narrowest portion of the textile cross-sectional shape, or both. For example, the first shape first dimension can be measured across the widest portion and the first shape second dimension can be perpendicular to the first shape first dimension such that the first shape first and second axes are perpendicular to one another (e.g., such that the first shape second dimension may or may not be measured across the narrowest portion). As another example, the first shape first dimension can be measured across the widest portion and the first shape second dimension can be measured across the narrowest portion such that the first shape first and second axes may or may not be perpendicular to one another. The first shape first and second axes can intersect at or in the textile first cross-sectional shape center. The textile first cross-sectional shape can have a perimeter (also referred to as a textile first cross-sectional shape perimeter). The perimeter of the first cross-sectional shape can have one or more straight portions, one or more curved portions, or both.

The textile second cross-sectional shape can have a regular shape or an irregular shape. The textile second cross-sectional shape can have one or more straight edges, one or more curved edges, or both. The curved edges can define circular or non-circular arcs. The textile second cross-sectional shape can have one or more straight sides, one or more curved sides, or both. The curved sides can define circular or non-circular arcs. For example, the textile second cross-sectional shape can be a non-circular, non-elliptical, circular, elliptical, oblong, rectangular, stadium, or irregular shape. The textile second cross-sectional shape can be non-flat or less flat.

The textile second cross-sectional shape (e.g., a non-flat or less flat shape) can have a second shape first dimension along a second shape first axis and a second shape second dimension along a second shape second axis. The second shape first and second dimensions can be measured across the center of the textile second cross-sectional shape (also referred to as the textile second cross-sectional shape center). The textile second cross-sectional shape center can be the axial center of the textile second cross-sectional shape (e.g., a center point), can be the center of mass of the textile second cross-sectional shape (e.g., actual center of mass of the textile cross-section, or can assume a nominal mass unit of 1 is distribute evenly across the textile second cross-sectional shape), or can be a center region of the textile second cross-sectional shape (e.g., where the center region can have an area of about 0.25 mm² to about 7.5 mm², or more narrowly, from about 0.1 mm² to about 2 mm², including every 0.1 mm² increment within these range).

The second shape first and second axes can be angled relative to one another, for example, from about 5 degrees to about 175 degrees, or more narrowly, from about 15 degrees to about 165 degrees, including every 1 degree increment within these ranges (e.g., 5 degrees, 75 degrees, 90 degrees, 105 degrees, 175 degrees). The second shape first and second axes can be straight and/or curved.

The second shape first dimension can be greater than or equal to the second shape second dimension. For example, the second shape first dimension can be greater than the second shape second dimension by about 0.1 mm to about 15.00 mm, or more narrowly, by about 0.25 mm to about 5.00 mm, including every 0.01 mm increment within these ranges. As another example, the second shape first dimension can be greater than the second shape second dimension by about 0.5% to about 1000%, or more narrlowly, by about 1% to about 100%, including every 5% increment within these ranges. The second shape first dimension can be measured across the widest portion of the textile second cross-sectional shape, the second shape second dimension can be measured across the narrowest portion of the textile cross-sectional shape, or both. For example, the second shape first dimension can be measured across the widest portion and the second shape second dimension can be perpendicular to the second shape first dimension such that the second shape first and second axes are perpendicular to one another (e.g., such that the second shape second dimension may or may not be measured across the narrowest portion). As another example, the second shape first dimension can be measured across the widest portion and the second shape second dimension can be measured across the narrowest portion such that the second shape first and second axes may or may not be perpendicular to one another. As yet another example, where the second cross-sectional shape is a circle, the second shape first and second dimensions can each be the diameter of the circle such that the first and second dimensions are equal to one another. The second shape first and second axes can intersect at or in the textile second cross-sectional shape center. The textile second cross-sectional shape can have a perimeter (also referred to as a textile second cross-sectional shape perimeter). The perimeter of the second cross-sectional shape can have one or more straight portions, one or more curved portions, or both.

The second shape first dimension can be less than the first shape first dimension. For example, the second shape first dimension can be less than the first shape first dimension by about 0.10 mm to about 10.00 mm, or more narrowly, by about 0.25 mm to about 5.00 mm, including every 0.01 mm increment within these ranges. As another example, the second shape first dimension can be less than the first shape first dimension by about 0.5% to about 1000%, or more narrowly, by about 1% to about 500%, including every 5% increment within these ranges.

The second shape second dimension can be greater than the first shape second dimension. For example, the second shape second dimension can be greater than the first shape second dimension by about 0.10 mm to about 10.00 mm, or more narrowly, by about 0.25 mm to about 5.00 mm, including every 0.01 mm increment within these ranges. As another example, the second shape second dimension can be greater than the first shape second dimension by about 0.5% to about 1000%, or more narrowly, by about 1% to about 500%, including every 5% increment within these ranges.

The textile second cross-sectional shape can be a shape in which the difference between the second shape first dimension and the second shape second dimension is not as great as the difference between the first shape first dimension and the second shape second dimension.

Additional material can be added to the textile 13, for example, via an injection or spray process. The additional material can be any of the materials disclosed herein. The additional material can be in a melted form and can be injected or sprayed into the die hole 19 (e.g., via an injection channel) and/or onto the textile 13 before the textile 13 moves into the die 18. The additional material can form part of the textile 13, for example, such that the additional material can form part of the textile second cross-sectional shape. Where additional material is added to the textile 13 during the cross-sectional shape transformation process, the second shape first dimension can be equal to the first shape first dimension, or the second shape first dimension can be less than the first shape first dimension by about 0.01 mm to about 5.00 mm, or more narrowly, by about 0.25 mm to about 1.00 mm, including every 0.01 mm increment within these ranges.

When the textile first cross-sectional shape is overlaid the textile second cross-sectional shape, or vice versa, and the first shape first axis is aligned with (e.g., made to be coincident with) the second shape first axis, the first shape second axis can be coincident with or angled relative to the second shape second axis. When the textile first cross-sectional shape is overlaid the textile second cross-sectional shape, or vice versa, and the first shape second axis is aligned with (e.g., made to be coincident with) the second shape second axis, the first shape first axis can be coincident with or angled relative to the second shape first axis.

The textile first cross-sectional size and/or shape can be the same as or different from the textile second cross-sectional and/or shape. The textile first cross-sectional size and/or shape can be changed to the textile second cross-sectional size and/or shape. The textile first cross-sectional shape can have a first shape area. The textile second cross-sectional shape can have a second shape area. About 2% to about 95% of the area of the textile first cross-sectional shape can fit inside a reference shape (e.g., reference circle) having the same cross-sectional area as the textile first cross-sectional shape (i.e., as the first shape area), including every 1% increment within this range. About 5% to about 95% of the area of the textile first cross-sectional shape can fit inside a reference shape (e.g., reference circle) having the same cross-sectional area as the textile first cross-sectional shape (i.e., as the first shape area). The cross-sectional area of the reference circle is also referred to as the reference circle cross-sectional area. About 10% to about 100% of the area of the textile second cross-sectional shape can fit inside the reference circle cross-sectional area, including every 1% increment within this range. About 25% to about 100% of the area of the textile second cross-sectional shape can fit inside the reference circle cross-sectional area, including every 1% increment within this range. About 50% to about 100% of the area of the textile second cross-sectional shape can fit inside the reference circle cross-sectional area, including every 1% increment within this range. About 75% to about 100% of the area of the textile second cross-sectional shape can fit inside the reference circle cross-sectional area, including every 1% increment within this range. More of the textile second cross-sectional shape can fit inside the reference circle than the textile first cross-sectional shape. For example, about 2% to about 98% more of the textile second cross-sectional shape can fit inside the reference circle than the textile first cross-sectional shape, including every 1% increment within this range. The reference circle can have an area of about 0.25 mm$^2$ to about 4.00 mm$^2$, including every 0.01 mm$^2$ increment within this range. As another example, the reference shape can be the cross-sectional shape of the die hole 19. To determine the percentage overlap between the textile first cross-sectional shape and the reference circle, the textile first cross-sectional shape can be overlaid with the reference circle such that the textile first cross-sectional shape center is coincident with the center of the reference circle. To determine the percentage overlap between the textile second cross-sectional shape and the reference circle, the textile second cross-sectional shape can be overlaid with the reference circle such that the textile second cross-sectional shape center is coincident with the center of the reference circle.

The textile cross-sectional shape can be viewed in a plane transverse (e.g., perpendicular) to a textile longitudinal axis. The textile longitudinal axis can be the long axis of the textile 13. The perimeter (e.g., outer perimeter) of the textile cross-section can be the boundary of the textile cross-sectional shape. The perimeter of the textile first cross-sectional shape can be open or closed. The perimeter of the textile second cross-sectional shape can be open or closed. A closed perimeter can define a closed shape. For example, a textile cross-sectional shape having a closed perimeter can be a closed shape without any recesses or cavities. An open perimeter can define an open shape. For example, a textile cross-sectional shape having an open perimeter can be an open shape having one or multiple recesses or cavities. For example, the perimeter of the textile first cross-sectional shape can be closed (e.g., a non-circular, non-elliptical, circular, "O", elliptical, oblong, rectangular, stadium, or irregular closed shape) and the perimeter of the textile second cross-sectional shape can be closed (e.g., a non-circular, non-elliptical, circular, "O", elliptical, oblong, rectangular, stadium, or irregular closed shape) or open (e.g., a C-, U-, V-, M-, W-, S-, Z-, irregular, non-circular, non-elliptical, circular, "O", elliptical, oblong, rectangular, or stadium open shape). The perimeter can be open, for example, when the textile 13 folds to fit into and the die hole. The open perimeter can, but may not, melt closed such that the textile second cross-sectional shape can have one or multiple open seams or one or multiple closed seams. When a textile folds to fit into a die hole 19, one or multiple seams can form. The seams can be open or closed, for example, not melted together or melted together, respectively. The seams of C-, U-, V-, M-, W-, S-, Z-, irregular-shaped folds can be the openings in the perimeter of the cross-sectional shape of the textile 13. The seams can be, for example, where the ends of the C-, U-, V-, M-, W-, S-, Z-, irregular-shaped folds are not connected (e.g., melted together). The seams can be, for example, where the peaks of the M-, W-, S-, Z-, irregular-shaped folds are not connected (e.g., melted together). With or without seams that can result from folding, the textile second cross-sectional shape can define a round cross-sectional, a cross-sectional area less non-round than the textile first cross-sectional shape, and/or a cross-sectional shape more round than the textile first cross-sectional shape.

While the textile 13 is in the die hole 19, the cross-sectional shape of the textile 13 can take on the cross-sectional shape of the die hole. While the textile 13 is in the die hole 19, the textile 13 can occupy about 40% to about 100%, or more narrowly, about 70% to about 100%, of the cross-section of the die hole 19, including every 1% increment within these ranges. The cross-section of the die hole 19 can be perpendicular to the textile longitudinal axis.

The die 18 can temporarily or permanently change the textile first cross-sectional size and/or shape to the textile second cross-sectional size and/or shape along one or more portions of the textile 13, including, for example, along the entire length of the textile 13 or any lesser length. For example, where the textile first cross-sectional shape has a long axis and a short axis, the die 18 can decrease the dimension along the long axis and increase the dimension along the short axis such that the textile second cross-sectional shape has a shorter long axis and a longer short axis than the textile first cross-sectional shape.

The portions of the textile 13 that have been heated can pass through or be forced through the die 18 when these portions are in a heated state. The portions of the textile 13 that have not been heated can pass through or be forced through the die 18 when these portions are in a non-heated state. The heated portions of the textile 13 can remain in the second cross-sectional shape after passing through the die hole 19. The non-heated portions of the textile 13 can relax (e.g., unfold or expand) and partially or fully return to the first cross-sectional shape after passing through the die hole 19. For example, when the textile 13 folds to fit into the die hole, the heated portions of the textile 13 can remain partially or fully folded after exiting the die 18 and the non-heated portions of the textile 13 can partially or fully unfold after exiting the die 18. As another example, when the textile 13 expands and/or contracts to fit into the die hole (e.g., with or without also folding), the heated portions of the textile 13 can remain partially or fully expanded and/or contracted after exiting the die 18 and the non-heated portions of the textile 13 can partially or fully contract and/or expand, respectively, after exiting the die 18.

The heated portions of the textile can remain in the textile second cross-sectional shape after passing through the die hole 19 because, for example, the heated portion can melt together and/or cool and harden in the die hole 19 shape. As another example, after passing through the die hole 19, the cross-sectional shape of the heated portion can slightly increase in size but retain the shape of the die hole 19 because, for example, the textile 13 can slightly unfold or un-bunch during cooling. As yet another example, after passing through the die hole 19, the cross-sectional shape of the heated portion can slightly increase in size but retain the shape of the die hole 19 because, for example, the textile 13 can slightly expand during cooling (e.g., when the textile 13 contracted along one or multiple axes to fit into the die hole 19 this material can rebound after passing through the die hole 19). As yet still another example, after passing through the die hole 19, the cross-sectional shape of the heated portion can slightly decrease in size but retain the shape of the die hole 19 because, for example, the textile 13 can slightly contract during cooling as the energy of the material of the textile 13 decreases. As yet still more examples, the heated portion(s) can retain the die shape and not unfold, expand, or contract—or only partially unfold, expand, or contract—by virtue of braids of a braided textile 13 melting together, by virtue of the lateral sides of the textile 13 melting together (e.g., while folded and pressed against each other), by virtue of the textile 13 hardening in the die shape or folded shape, or any combination thereof.

The textile 13 can have a non-heated cross-sectional shape, a post-heated pre-die cross-sectional shape, a post-heated die cross-sectional shape, and a post-heated post-die cross-sectional shape. The non-heated cross-sectional shape can have the textile first cross-sectional shape. The post-heated pre-die cross-sectional shape can have the textile first cross-sectional shape. The post-heated pre-die cross-sectional shape can have a folded shape (e.g., C-, U-, V-, M-, W-, S-, Z-, irregular-shaped fold), a contracted shape, an expanded shape, or any combination thereof. The post-heated pre-die cross-sectional shape can approach the die hole cross-sectional shape (which can be the textile second cross-sectional shape) in a textile transition region as the textile 13 is moved out of the heater 16 and into the die 18 and assumes a folded, expanded, and/or contracted configuration. The transition region can be in the heater 16, after the heater 16, before the die 18, in the die 18, or any combination thereof. For example, the transition region can be between the heater and the die 16, 18. The transition region can extend over a transition distance of about 1 mm to about 100 mm, or more narrowly, about 1 mm to about 50 mm, including every 1 mm increment within these ranges. The post-heated die cross-sectional shape can be the textile second cross-sectional shape. The post-heated post-die cross-sectional shape can be the textile second cross-sectional shape.

The textile 13 can be moved (e.g., pulled) through the die 18 after having been heated by the heater 16 and/or after bypassing the heater 16 (i.e., after skipping the heater 16 on the way to the die 18). For example, the heated portion can be moved through the die 18 after being heated by the heater 16 and the non-heated portion can be moved through the die 18 after bypassing the heater 16. When the non-heated portion bypasses the heater 16, the heater 16 can be on (i.e., emitting energy) or off (i.e., not emitting energy). As another example, the textile 13 can be moved (e.g., pulled) through the die 18 after having been heated by the heater 16 and/or after going through the heater 16 when the heater 16 is off. In this case, both the heated and non-heated portions can be moved through the die 18 after having gone through the heater 16—the heated portion when the heater 16 is on and the non-heated portion when the heater 16 is off.

The heater 16 and/or the die 18 can be removably attachable and/or removably detachable from each other, from a support (e.g., support surface), and/or from the shaper 10 (e.g., from a surface or platform of the shaper 10) with or without partial or complete disassembly of the heater 16, the die 18, and/or the shaper 10.

The heater 16 and/or the die 18 can be modular such that they can be interchanged with other heaters and/or dies (e.g., other heaters 16, other dies 18), for example, in real-time during production or processing of a textile (e.g., textile 13) so that production downtime is limited, reduced, or optimized if there is a breakdown or if a different heater or die having different heating or die specifications is desired or required.

The textile shaper 10 can convert one or more portions of a textile 13 from a textile first cross-sectional size and/or shape to a textile second cross-sectional size and/or shape. In this way the textile shaper 10 can create sutures having one or multiple suture first portions (e.g., having the textile first cross-sectional shape) and one or more suture second portions (e.g., having the textile second cross-sectional shape). Each suture created by the textile shaper 10 can have 1 to 10 or more suture first portions, including every 1 unit increment within this range (e.g., 1 non-round portion, 2 non-round portions). Each suture created by the textile shaper 10 can have 1 to 10 or more suture second portions, including every 1 unit increment within this range (e.g., 1 round portion, 2 round portions). As another example, the heater and die 16, 18 can thereby change one or multiple portions of the textile 13 from a non-round configuration textile (e.g., flat braided textile) to a round configuration textile (e.g., round braided textile).

The textile mover 20 can move (e.g., pull) the textile 13 (e.g., the non-heated and heated portions of the textile 13) through the heater 16 and/or through the die 18. The textile mover 20 can be a linear actuator. The textile mover 20 (e.g., linear actuator) can have one or more textile grips and can translate and/or rotate the textile 13 through the heater 16 and/or the die 18. A sizer 22 (e.g., cutter) can size (e.g., cut) the textile 13 to a target length (also referred to as a final length), for example, to create a suture having a suture length. The target length can be about 5 cm to about 200 cm or more, or more narrowly, about 10 cm to about 100 cm or more, including every 1 cm increment within these ranges (e.g., 5 cm, 10 cm, 25 cm, 50 cm, 75 cm, 100 cm, 125 cm, 150 cm, 175 cm, 200 cm). The suture length can be the same as or less than the target length. The suture length can be about 5 cm to about 200 cm or more, or more narrowly, about 10 cm to about 100 cm or more, including every 1 cm increment within this range (e.g., 5 cm, 10 cm, 25 cm, 50 cm, 75 cm, 100 cm, 125 cm, 150 cm, 175 cm, 200 cm). The heated portion length can be greater than, less than, or equal to the non-heated portion length, for example, before and/or after an end of the textile 13 is sized (e.g., cut) to create a textile (e.g., suture) having a textile target length.

FIG. 1B illustrates that the heater 16 can have a heater chamber 17. The textile 13 can be heatable in the chamber 17. The textile 13 can be heated in the chamber 17. The heater 16 can emit energy toward the textile 13, for example, when the textile 13 is inside and/or outside of the chamber 17. The heater 16 can emit energy toward a reflector, for example, when the textile 13 is inside and/or outside of the chamber 17. The reflector be a surface of the heater chamber 17. The heater 16 can heat the textile 13 such that the material of the heated portion melts. When the heated portion of the textile 13 is in a melted phase, the heated material can flow such that the die 18 can deform the heated portion into a new size (e.g., same size or smaller size) and/or into a new shape (e.g., a folded shape, a round shape, a folded and round shape).

The textile 13 can be longitudinally fixed and/or longitudinally movable when inside the chamber 17. When inside the chamber 17, the textile 13 can be moved longitudinally in a longitudinal first direction (e.g., forward direction, toward the die 18). When inside the chamber 17, the textile 13 can be moved longitudinally in a longitudinal second direction (e.g., backward direction, away from the die 18) opposite the longitudinal first direction. When inside the chamber 17, the textile 13 can be longitudinally moved, for example, from a chamber first end 17a to a chamber second end 17b or vice versa. The chamber first end 17a can be closer to or farther from the die 18 than the chamber second end 17b. When inside the chamber 17, the textile 13 can be longitudinally moved when the heater 16 is on, when the heater 16 is off, or when the heater 16 is on and when the heater 16 is off.

The textile 13 can be longitudinally fixed and/or longitudinally movable when outside the chamber 17. When outside of the chamber 17, the textile 13 can be moved longitudinally in the longitudinal first direction (e.g., forward direction, toward the die 18). When outside of the chamber 17, the textile can be moved longitudinally in the longitudinal second direction (e.g., backward direction, away from the die 18). When outside of the chamber 17, the textile 13 can be longitudinally moved, for example, from a textile first position to a textile second position. The textile first position can be closer to or farther from the die 18 than the textile second position. When outside of the chamber 17, the textile 13 can be longitudinally moved when the heater 16 is on, when the heater 16 is off, or when the heater 16 is on and when the heater 16 is off.

The textile 13 can be moved in a longitudinal direction into and out of the chamber 17. The longitudinal direction can be parallel to the textile longitudinal axis. The textile 13 can be moved in a lateral direction into and out of the chamber 17. The lateral direction can be perpendicular to the textile longitudinal axis. The textile 13 can be move longitudinally and/or laterally, for example, relative to the heater 16, the die 18, or both. The textile 13 can be moved laterally along a lateral first axis, laterally along a lateral second axis, or both, where the lateral first axis can be perpendicular to the lateral second axis, and where the lateral first and second axes can be perpendicular to the textile longitudinal axis. The textile 13 can be moved in first direction along the lateral first axis and in a second direction opposite the first direction along the lateral first axis. The textile can be moved in a first direction along the lateral second axis and in a second direction opposite the first direction along the lateral second axis. The lateral first axis can be a horizontal or vertical axis. The lateral second axis can be a horizontal or vertical axis. The textile longitudinal axis can be straight or curved. The lateral first axis can be straight or curved. The lateral second axis can be straight or curved.

The textile 13 can be moved while being heated in the chamber 17. For example, the textile 13 can be longitudinally moved, laterally moved, and/or rotated while being heated in the chamber 17.

The textile 13 can be fixed in place while being heated in the chamber 17. For example, the textile 13 can be longitudinally, laterally, and/or rotationally stationary while being heated in the chamber 17.

FIG. 1B further illustrates that the heater 16 can be on a moveable base 24 having one or multiple engagers 26 (e.g., first and second engagers as shown, for example, one on each side of the moveable base 24). The engagers 26 can be slideable in tracks 28. The engagers and tracks 26, 28 can engage with one another in a tongue and groove arrangement, where the engagers 26 can be the tongues and the tracks can be the grooves 28, or vice versa.

FIG. 1B further illustrates that the textile 13 can be outside of the chamber 17.

Figure 1C:
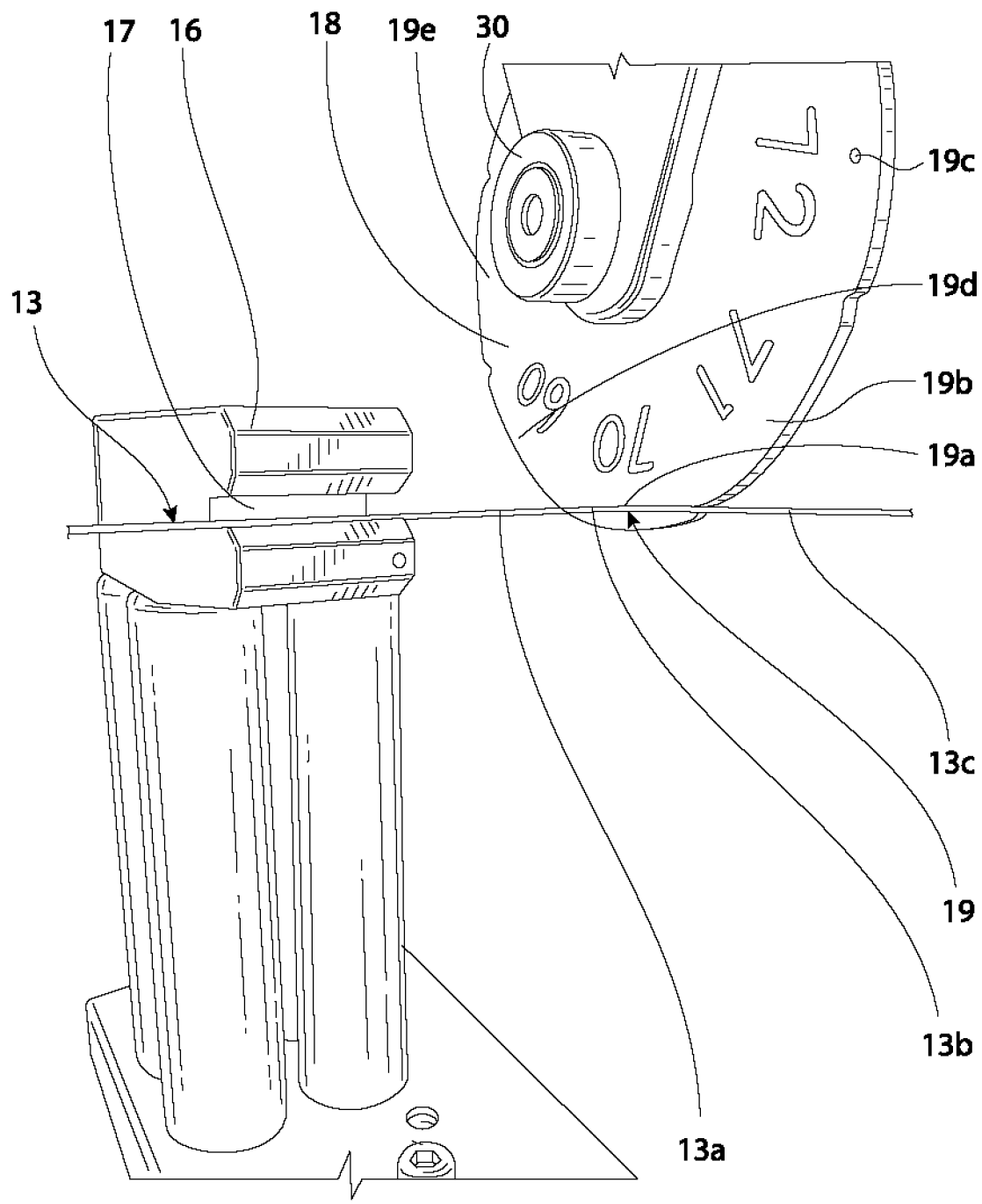
FIG. 1C illustrates a magnified perspective view of the textile shaper of FIG. 1B.

FIG. 1C illustrates that a portion of the textile 13 can be partially or completely inside the chamber 17.

FIG. 1C further illustrates that the textile 13 can have a textile first portion 13a, a textile second portion 13b, and a textile third portion 13c. The textile first, second, and/or third portions 13a-13c can be moved through the shaper 10. For example, the textile first, second, and/or third portions 13a-13c can be positioned before the heater 16, in the heater 16, after the heater 16, before the die 18, in the die 18, after the die 18, or any combination thereof. For example, in the positions shown, the textile first, second, and/or third portions 13a-13c can be positioned after the heater 16. In this position, the textile first, second, and/or third portions 13a-13c can have not been heated by the heater 16. As another example, in this position, the textile first, second, and/or third portions 13a-13c can have been previously heated by the heater 16. For example, the first, second, and/or third portions 13a-13c can be in a heated condition (also referred to as a melted condition), for example, heated from a first temperature to a second temperature. The first, second, and/or third portions 13a-13c can be cooling down, for example, from the second temperature to a third temperature. As another example, the textile first, second, and/or third portions 13a-13c can be at the third temperature. The third temperature can be less than the second temperature and can be less than, equal to, or greater than the first temperature.

The first temperature can be about 10 degrees Celsius to about 300 degrees Celsius, or more narrowly, about 15 degrees Celsius to about 50 degrees Celsius, including every 1 degree Celsius increment within these ranges (e.g., 40 degrees Celsius). The second temperature can be about 15 degrees Celsius to about 300 degrees Celsius, or more narrowly, about 80 degrees Celsius to about 200 degrees Celsius, or more narrowly still, about 80 degrees Celsius to about 150 degrees Celsius, including every 1 degree Celsius increment within these ranges (e.g., 100 degrees Celsius, 120 degrees Celsius). The third temperature can be about 20 degrees Celsius to about 300 degrees, or more narrowly, about 50 degrees Celsius to about 200 degrees Celsius, including every 1 degree Celsius increment within these ranges. The second temperature can be the same as or less than the first temperature. The third temperature can be the same as or less than the first temperature. The third temperature can be the same as or less than the second temperature.

The textile first portion 13a can have a textile first portion length of about 5 mm to about 1000 mm, including every 1 mm increment within this range. The textile second portion 13b can have a textile second portion length of about 2 mm to about 5000 mm, or more narrowly, about 5 mm to about 1000 mm, including every 1 mm increment within these ranges. The textile third portion 13c can have a textile third portion length of about 2 mm to about 5000 mm, or more narrowly, about 5 mm to about 1000 mm, including every 1 mm increment within these ranges.

The textile 13 can be actively cooled and/or can be allowed to passively cool. A textile temperature reducer (e.g., a cooler) and/or the die 18 can cool the textile 13 after it passes through the heater 16. For example, the die 18 can cool the textile 13 from a heated temperature (e.g., the second temperature) to the third temperature or to a temperature between the heated temperature and the third temperature. The die 18 can have, for example, a conductive lining (e.g., a metal lining, for example, a copper lining) in the holes 19 which can conduct heat away from the textile 13 and into the copper, and into the die 18. The die 18 can be insulated. A fluid can be forced (e.g., poured, sprayed) over the die 18 to cool and/or lubricate the die hole 19. A fluid can be forced (e.g., poured, sprayed) over the textile 13 to cool and/or lubricate the textile 13. The fluid forced over the textile 13 can cool and/or lubricate the die hole 19 when the portion of the textile 13 having the fluid passes through the die hole 19. The fluid can be, for example, water, oil, and/or lubricant. The die 18 can have a die temperature. The die temperature can be about −100 degrees Celsius to about 300 degrees Celsius, or more narrowly, about 0 degrees Celsius to about 300 degrees Celsius, or more narrowly still, about 15 degrees Celsius to about 150 degrees Celsius, including every 1 degree Celsius increment within these ranges. A cooling source can keep the die 18 at the die temperature. The cooling source can be the fluid. As the textile 13 cools to a lower temperature from the heated temperature, the individual fibers of the textile 13 can remain (e.g., stick) together and become harder to distinguish.

The textile first portion 13a can have the textile first cross-sectional size and/or shape. The textile second portion 13b can have a textile transition cross-sectional size and/or shape. The textile transition cross-sectional size and/or shape can be a size and/or shape between the textile first and second cross-sectional sizes and/or shapes. For example, the textile second portion 13b can be in the transition region where the first cross-sectional size and/or shape transitions to the second cross-sectional size and/or shape and vice versa. The textile third portion 13c can have the textile second cross-sectional size and/or shape. The textile first cross-sectional shape can have a first shape area of about 0.10 mm$^2$ to about 15.00 mm$^2$, or more narrowly, about 0.25 mm$^2$ to about 5.00 mm$^2$, including every 0.01 mm$^2$ increment within these ranges. The textile first cross-sectional shape can have a cross-sectional perimeter of about 0.10 mm to about 20.0 mm, or more narrowly, about 1.0 mm to about 10.0 mm, including every 0.01 mm increment within these ranges. The textile second cross-sectional shape can have a second shape area of about 0.10 mm$^2$ to about 15.00 mm$^2$, or more narrowly, about 0.25 mm$^2$ to about 5.00 mm$^2$, including every 0.01 mm$^2$ increment within these ranges. The textile second cross-sectional shape can have a cross-sectional perimeter of about 0.10 mm to about 20.0 mm, or more narrowly, about 1.0 mm to about 10.0 mm, including every 0.01 mm increment within these ranges.

The non-heated portions (e.g., textile first and second portions 13a, 13b) can be retain their strength (e.g., tensile strength) after passing through the die 18. The tensile strength of the non-heated (also referred to as not previously heated by the heater 16 portions) can be from about 1 Newtons to about 200 Newtons, or more narrowly, from about 10 Newtons to about 35 Newtons, including every 1 Newton increment within this range. The heated portions (e.g., textile third portion) can have a lower strength (e.g., tensile strength) than the non-heated portions because some of the individual fibers of the textile can be stuck or melted together. The tensile strength of the heated (also referred to as previously heated by the heater 16 portions) can be from about 0.5 Newtons to about 199 Newtons, or more narrowly, from about 5 Newtons to about 30 Newtons, including every 1 Newton increment within these ranges.

FIG. 1C further illustrates that the die 18 can have one or multiple holes 19, for example, 1-20 or more holes 19, including every 1 hole 19 increment within this range (e.g., 1 hole, 2 holes, 10 holes, 20 holes), such as first through fifth portions 13a, 13b) The size of each hole 19 can be the same or different as another hole 19. The die 18 can be a die with indexed holes 19 having various sizes. The cross-sectional area of each of the holes 19 can be from about 0.10 mm$^2$ to about 15.00 mm$^2$, or more narrowly, from about 0.25 mm$^2$ to about 5.00 mm$^2$, including every 0.01 mm$^2$ increment within these ranges, where the cross-sectional area can be measured across a cross-sectional plane perpendicular to the textile longitudinal axis and/or perpendicular to a die hole longitudinal axis.

FIG. 1C further illustrates that the die 18 can be a die wheel. For example, the die 18 can be a rotatable wheel having holes 19 (e.g., holes 19a-19e). The die 18 can have a circular or non-circular perimeter. The die 18 can be metal, for example, steel (e.g., stainless steel). As a heated textile 13 passes through a die hole 19, the textile 13 cross-sectional shape can be changed from the textile first cross-sectional shape (e.g., flat) to the textile second cross-sectional shape (e.g., less flat). The holes 19 can be indexed so that the user can select the textile shape (e.g., circle) that is desired. The holes 19 can be indexed so that the user can select the textile size (e.g., diameter) that is desired. The die hole 19 selected can be the desired size of a textile tip after the textile 13 is sized (e.g., cut) after passing through the die 18. Having multiple die holes 19 on a single die (e.g., die 18) can advantageously make processing the textile 13 more efficient since the die 18 can simply be rotated to change the textile cross-section size and/or shape instead of having to, for example, replace or change out the die 18 altogether with a different die. This can advantageously lead to less down time when multiple cross-sectional shapes and/or sizes are created along a single textile (e.g., along a non-sized or pre-sized textile 13). For example, FIG. 1C further illustrates that the die 18 can be adjusted (e.g., rotated) with a die control 30. The die control 30 can be turned clockwise, counterclockwise, or in both directions.

The textile 13 can pass through the heater 16 and/or die holes 19 at a textile speed of about 0.01 cm/s to about 1000 cm/s, or more narrowly, about 1 cm/s to about 25 cm/s, including every 1 and 0.01 centimeter/second increment within these ranges. The textile 13 can be moved through the heater 16 at the same rate, a lesser rate, or a greater rate than through the die 18.

Figure 1D:
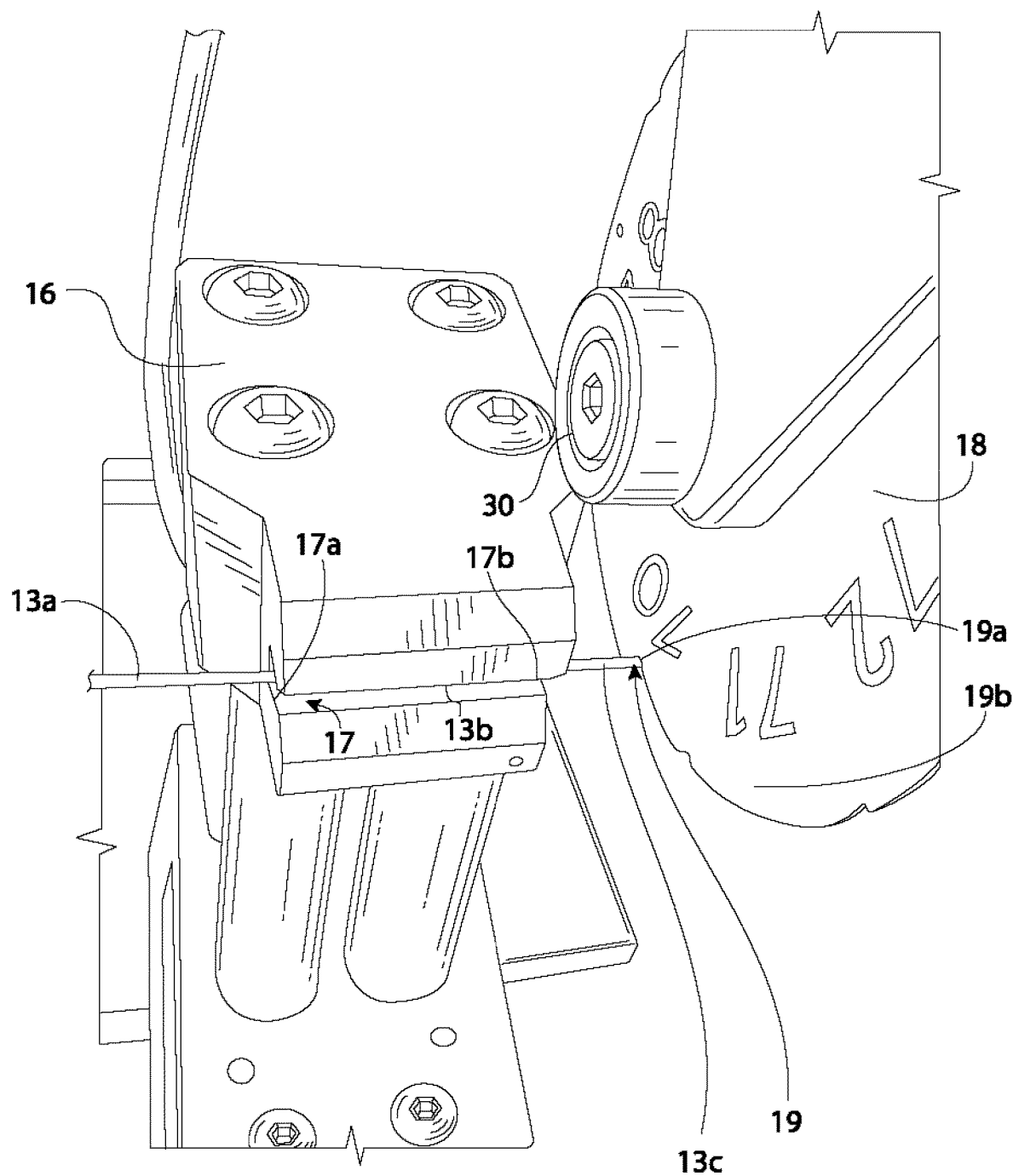
FIG. 1D illustrates a magnified perspective view of the textile shaper of FIG. 1C.

FIG. 1D illustrates that a portion of the textile 13 can be completely inside the chamber 17.

FIG. 1D further illustrates that the textile first portion 13a can be before the heater 16, that the textile second portion 13b can be in heater 16, and that the textile third portion 13c can be after the die 18. The textile first portion 13a can have the textile first cross-sectional shape, the textile transition cross-sectional shape (e.g., a taco shape, a folded shape, a bent shape, a shape having a bend), or both. The textile second portion 13b can have the textile first cross-sectional shape, the transition cross-sectional shape, or both. The textile third portion 13c can have the transition cross-sectional shape, the textile second cross-sectional shape, or both. For example, FIG. 1D illustrates that the textile first and second portions 13a, 13b can be flat and that the textile third portion 13c can have a transition cross-sectional shape (e.g., a taco shape, a folded shape, a bent shape, a shape having a bend).

Figure 2A:
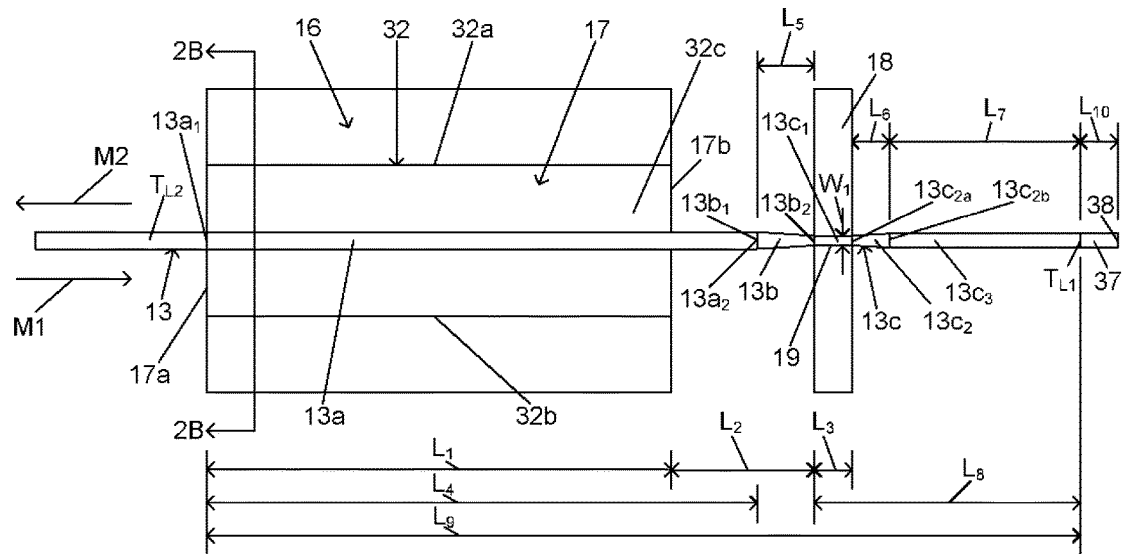
FIG. 2A illustrates a schematic of a variation of a textile shaper.

FIG. 2A illustrates that the textile 13, the heater 16, and/or the die 18 can be longitudinally movable. The textile 13 can be moved longitudinally in a longitudinal first direction M1 (e.g., forward direction, toward the die 18), in a longitudinal second direction M2 (e.g., backward direction, away from the die 18) opposite the longitudinal first direction M1, or in both directions. The heater 16 can be moved longitudinally in a longitudinal first direction M1 (e.g., forward direction, toward the die 18), in a longitudinal second direction M2 (e.g., backward direction, away from the die 18) opposite the longitudinal first direction M1, or in both directions. The die 18 can be moved longitudinally in a longitudinal first direction M1 (e.g., forward direction, away from the heater 16), in a longitudinal second direction M2 (e.g., backward direction, toward the heater 16) opposite the longitudinal first direction M1, or in both directions. The textile 13 can move (e.g., longitudinally) while the heater 16 is moving, while the heater 16 is fixed in place, while the die 18 is moving, while the die 18 is fixed in place, or any combination thereof. The heater 16 can move (e.g., longitudinally) while the textile 13 is moving, while the textile 13 is fixed in place, while the die 18 is moving, while the die 18 is fixed in place, or any combination thereof. The die 18 can move (e.g., longitudinally) while the textile 13 is moving, while the textile 13 is fixed in place, while the heater 16 is moving, while the heater 16 is fixed in place, or any combination thereof. For example, the textile, heater, and/or die 13, 16, 18 can move when one or two of the other of the textile, heater, and/or die 13, 16, 18 is stationary (e.g., longitudinally stationary).

FIG. 2A further illustrates that one or multiple surfaces 32 can define the chamber 17, for example, first through third surfaces 32a-32c. The surfaces 32 can be flat and/or curved. The surfaces 32 can be reflective. The surfaces 32 can be non-reflective.

FIG. 2A further illustrates that the textile 13 can be inside the chamber 17, outside the chamber 17, or both.

FIG. 2A further illustrates that the textile 13 can move through the chamber 17 before the textile 13 passes through the die 18. As another example, FIG. 2A further illustrates that the textile 13 can bypass (i.e., go around) the chamber 17 before the textile 13 passes through the die 18.

FIG. 2A further illustrates that the textile first, second, and/or third portions 13a-13c can have the arrangement shown, for example, in relation to the heater 16, the die 18, or both.

FIG. 2A further illustrates that the textile first, second, and/or third portions 13a-13c can be heated or non-heated portions of the textile 13.

FIG. 2A further illustrates that the textile first portion 13a can have the textile first cross-sectional shape (e.g., non-round such as flat), that the textile second portion 13b can transition from the textile first cross-sectional shape to the textile second cross-sectional shape (e.g., round), for example, by deforming (e.g., by folding, expanding, and/or contracting, for example, to fit into the die hole 19), and that the textile third portion 13c can have the textile second cross-sectional shape (e.g., round). As another example, FIG. 2A further illustrates that the textile first portion 13a can have the textile first cross-sectional shape (e.g., non-round such as flat), that the textile second portion 13b can transition from the textile first cross-sectional shape to the textile second cross-sectional shape (e.g., round), for example, by deforming (e.g., by folding, expanding, and/or contracting, for example, to fit into the die hole 19), and that the textile third portion 13c can have the textile first cross-sectional shape (e.g., non-round such as flat).

The textile first portion 13a can extend from a textile first portion first end $13a_1$ to a textile first portion second end $13a_2$. The textile first portion 13a can have the textile first sectional shape. The textile first portion 13a can have a constant cross-sectional size and/or shape. The textile first portion 13a can be heated by the heater 16.

The textile second portion 13b can extend from a textile second portion first end $13b_1$ to a textile second portion second end $13b_2$. The textile first portion second end $13a_2$ can coincide with or abut the textile second portion first end $13b_1$. The textile second portion 13b can transition from the textile first cross-sectional shape to the textile second cross-sectional shape, for example, from the textile second portion first end $13b_1$ to the textile second portion second end $13b_2$. The textile 13 can be tapered between the textile second portion first end $13b_1$ to the textile second portion second end $13b_2$ such that one or multiple cross-sectional dimensions (e.g., width, length, height, diameter, perimeter, radius of curvature, and/or area) of the textile 13 (e.g., of the textile second portion 13b) becomes larger or smaller from the textile second portion first end $13b_1$ to the textile second portion second end $13b_2$. The tapered cross-sectional dimension can be measured along an axis perpendicular to the textile longitudinal axis. The cross-sectional dimension (e.g., width, length, height, diameter, perimeter, area, radius of curvature) at the textile second portion second end $13b_2$ can be, for example, about 0.01 mm to about 10.00 mm larger or smaller than the same dimension (e.g., width, length, height, diameter, perimeter, area, radius of curvature, respectively) at the textile second portion first end $13b_1$, including every 0.01 mm increment within this range. The cross-sectional dimension (e.g., width, length, height, diameter, perimeter, area, radius of curvature) at the textile second portion second end $13b_2$ can be, for example, about 0.1 mm to about 2.5 mm larger or smaller than the same dimension (e.g., width, length, height, diameter, perimeter, area, radius of curvature, respectively) at the textile second portion first end $13b_1$, including every 0.1 mm increment within this range. As another example, the cross-sectional dimension (e.g., width, length, height, diameter, perimeter, area, radius of curvature) at the textile second portion second end $13b_2$ can be, for example, about 0.5% to about 1000% larger or smaller than the same dimension (e.g., width, length, height, diameter, perimeter, area, radius of curvature, respectively) at the textile second portion first end $13b_1$, including every 0.5% increment within this range. The cross-sectional dimension (e.g., width, length, height, diameter, perimeter, area, radius of curvature) at the textile second portion second end $13b_2$ can be, for example, about 1% to about 100% larger or smaller than the same dimension (e.g., width, length, height, diameter, perimeter, area, radius of curvature, respectively) at the textile second portion first end $13b_1$, including every 1% increment within this range. The second portion 13b can have a second portion first cross-sectional dimension and a second portion second cross-sectional dimension. These dimensions can be measured along axes perpendicular to the textile longitudinal axis. The second portion first cross-sectional dimension can become smaller, become larger, or remain constant from the textile second portion first end $13b_1$ to the textile second portion second end $13b_2$. The second portion second cross-sectional dimension can become smaller, become larger, or remain constant from the textile second portion first end $13b_1$ to the textile second portion second end $13b_2$. For example, the second portion first cross-sectional dimension can become smaller and the second portion second cross-sectional dimension can become larger from the textile second portion first end $13b_1$ to the textile second portion second end $13b_2$. The textile second portion first end $13b_1$ can be before the die 18, inside or outside (as shown) of the heater 16. The textile second portion second end $13b_2$ can be before the die 18, at the entrance of a die hole 19 (as shown), or in a die hole 19.

The textile third portion 13c can have one or multiple third portion sections, for example, third portion first, second, and third sections $13c_1$-$13c_3$. The third portion first section $13c_1$ can be inside the die hole 19. Where the third portion 13c was previously heated by the heater 16, the die hole 19 can force melted and/or heated portions (e.g., fibers or filaments) of the textile third portion first section $13c_1$ together so that as the textile 13 cools from a heated condition, the textile 13 hardens in the shape of the die hole 19, such as in the textile second cross-sectional shape. Where the third portion 13c was not previously heated by the heater 16 (e.g., where the heater 16 is off or the textile 13 bypasses the heater 16), the die hole 19 can deform the textile third portion first section $13c_1$ so that it can pass through the die 18. The textile third portion second and third sections $13c_2$, $13c_3$ can be outside of the die hole 19, for example, distal to the die hole 19.

The third portion first, second, and third sections $13a_1$-$13c_3$ can have the same or different cross-sectional sizes and/or shapes as one another. For example, the third portion first, second, and third sections $13c_1$-$13c_3$ can have the second cross-sectional shape such as a round cross-sectional shape. The size and/or shape of the cross-sections of the third portion first, second, and third sections $13c_1$-$13c_3$ be constant or tapered. For example, the textile 13 can be tapered between a textile third portion second section first end $13c_{2a}$ to a textile third portion second section second end $13c_{2b}$ such that one or multiple cross-sectional dimensions (e.g., width, length, height, diameter, perimeter, radius of curvature, and/or area) of the textile 13 (e.g., of the textile third portion 13c) becomes larger or smaller from the textile third portion second section first end $13c_{2a}$ to the textile third portion second section second end $13c_{2b}$. The tapered cross-sectional dimension can be measured along an axis perpendicular to the textile longitudinal axis. The cross-sectional dimension (e.g., width, length, height, diameter, perimeter, area, radius of curvature) at the textile third portion second section first end $13c_{2a}$ can be, for example, about 0.01 mm to about 5.00 mm larger or smaller than the same dimension (e.g., width, length, height, diameter, perimeter, area, radius of curvature, respectively) at the textile third portion section second end $13c_{2b}$, including every 0.01 mm increment within this range. The tapered cross-sectional dimension can be measured along an axis perpendicular to the textile longitudinal axis. The cross-sectional dimension (e.g., width, length, height, diameter, perimeter, area, radius of curvature) at the textile third portion second section first end $13c_{2a}$ can be, for example, about 0.1 mm to about 2.5 mm larger or smaller than the same dimension (e.g., width, length, height, diameter, perimeter, area, radius of curvature, respectively) at the textile third portion section second end $13c_{2b}$, including every 0.1 mm increment within this range. As another example, the cross-sectional dimension (e.g., width, length, height, diameter, perimeter, area, radius of curvature) at the textile third portion second section first end $13c_{2a}$ can be, for example, about 0.5% to about 1000% larger or smaller than the same dimension (e.g., width, length, height, diameter, perimeter, area, radius of curvature, respectively) at the textile third portion second section second end $13c_{2b}$, including every 0.5% increment within this range. The cross-sectional dimension (e.g., width, length, height, diameter, perimeter, area, radius of curvature) at the textile third portion second section first end $13c_{2a}$ can be, for example, about 1% to about 100% larger or smaller than the same dimension (e.g., width, length, height, diameter, perimeter, area, radius of curvature, respectively) at the textile third portion second section second end $13c_{2b}$, including every 1% increment within this range. The third portion second section $13c_2$ can have a third portion second section first cross-sectional dimension and a third portion second section second cross-sectional dimension. These dimensions can be measured along axes perpendicular to the textile longitudinal axis. The third portion second section first cross-sectional dimension can become smaller, become larger, or remain constant from the textile third portion second section first end $13c_{2a}$ to the textile third portion second section second end $13c_{2b}$. The third portion second section second cross-sectional dimension can become smaller, become larger, or remain constant from the textile third portion second section first end $13c_{2a}$ to the textile third portion second section second end $13c_{2b}$. For example, the third portion second section first cross-sectional dimension can become smaller and the third portion second section second cross-sectional dimension can become larger from the textile third portion second section first end $13c_{2a}$ to the textile third portion second section second end $13c_{2b}$. The taper can be created by the textile un-deforming (e.g., unfold, un-expand, un-contract) from the textile third portion second section first end $13c_{2a}$ to the textile third portion second section second end $13c_{2b}$, for example, by progressively relaxing back into an un-deformed shape along the length of the textile third portion second section $13c_2$.

The size and shape of the textile 13 at the textile third portion second section second end $13c_{2b}$ can be the textile second cross-sectional size and/or shape desired.

Where the third portion 13c was previously heated by the heater 16, the melted and/or heated portions (e.g., fibers) of the textile third portion second section $13c_2$ can stick together so that as the textile 13 cools from a heated condition, the textile 13 hardens in the shape of the die hole 19 or in the second cross-sectional shape. A portion of the perimeter or the entire perimeter of the second cross-sectional shape of the heated portions can outline the shape of the die hole 19 when the heated portions are in the die hole 19 such that the heated portions can conform to the shape of the die hole 19. The previously heated portions can retain this conformed shape after exiting the die hole 19 such that a portion of the perimeter or the entire perimeter of the second cross-sectional shape of the heated portions can outline the shape of the die hole 19 after having exited the die hole 19.

Where the third portion 13c was not previously heated by the heater 16 (e.g., where the heater 16 is off or the textile 13 bypasses the heater 16), the textile can undeform (e.g., unfold, un-expand, un-contract) from the textile third portion second section first end $13c_{2a}$ to the textile third portion second section second end $13c_{2b}$, for example, progressively relaxing back into an un-deformed shape along the length of the textile third portion second section $13c_2$.

Where the textile third portion third section $13c_3$ was previously heated by the heater 16, the textile third portion third section $13c_3$ can be finished cooling or can still be cooling. The cross-sectional shape and/or size in the textile third portion third section $13c_3$ can be hardened state. The cross-sectional shape and/or size in the textile third portion third section $13c_3$ can have a uniform temperature. The cross-sectional shape and/or size in the textile third portion third section $13c_3$ can be tapered or non-tapered.

Where the textile third portion third section $13c_3$ was not previously heated by the heater 16, the textile third portion third section $13c_3$ can have the textile first cross-sectional shape.

The textile first, second, and/or third portions 13a-13c can be subsequently passed through the heater 16 again and/or the die 18 again at the same or a different heating temperature as the heating temperature during the first pass through the heater 16, and/or through the same sized or a smaller sized hole 19 as the first hole 19. As another example, the textile first, second, and/or third portions 13a-13c can be subsequently passed through a second heater 16 and/or a second die 18 at the same or a different heating temperature as the heating temperature during the first pass through the first heater 16, and/or through the same sized or a smaller sized hole 19 as the hole 19 in the first die 18.

FIG. 2A further illustrates that the die hole 19 can be the target cross-sectional size and/or shape for the second cross-sectional size and/or shape of the textile 13. As another example, one or multiple dimensions of the die hole 19 (e.g., width, length, height, diameter, perimeter, radius of curvature, and/or area) can be about 0.01 mm to about 5.00 mm smaller in size and/or shape than the target cross-sectional size and/or shape, for example, to accommodate expansion and/or unfolding that can occur during cooling of the textile 13 after having been heated and passed through a die hole, including every 0.01 mm increment within this range. As another example, one or multiple dimensions of the die hole 19 (e.g., width, length, height, diameter, perimeter, radius of curvature, and/or area) can be about 0.1 mm to about 2.5 mm smaller in size and/or shape than the target cross-sectional size and/or shape, for example, to accommodate expansion and/or unfolding that can occur during cooling of the textile 13 after having been heated and passed through a die hole, including every 0.1 mm increment within this range. As yet another example, one or multiple dimensions of the die hole 19 (e.g., width, length, height, diameter, perimeter, radius of curvature, and/or area) can be about 0.5% to about 500% smaller in size and/or shape than the target cross-sectional size and/or shape, for example, to accommodate expansion and/or unfolding that can occur during cooling of the textile 13 after having been heated and passed through a die hole, including every 0.5% increment within this range. As yet another example, one or multiple dimensions of the die hole 19 (e.g., width, length, height, diameter, perimeter, radius of curvature, and/or area) can be about 1% to about 25% smaller in size and/or shape than the target cross-sectional size and/or shape, for example, to accommodate expansion and/or unfolding that can occur during cooling of the textile 13 after having been heated and passed through a die hole, including every 1% increment within this range. As still yet another example, one or multiple dimensions of the die hole 19 (e.g., width, length, height, diameter, perimeter, radius of curvature, and/or area) can be about 0.01 mm to about 5.00 mm larger in size and/or shape than the target cross-sectional size and/or shape, for example, to accommodate contraction that can occur during cooling of the textile 13 after having been heated and passed through a die hole, including every 0.01 mm increment within this range. As still yet another example, one or multiple dimensions of the die hole 19 (e.g., width, length, height, diameter, perimeter, radius of curvature, and/or area) can be about 0.1 mm to about 2.5 mm larger in size and/or shape than the target cross-sectional size and/or shape, for example, to accommodate contraction that can occur during cooling of the textile 13 after having been heated and passed through a die hole, including every 0.1 mm increment within this range. As yet another example, one or multiple dimensions of the die hole 19 (e.g., width, length, height, diameter, perimeter, radius of curvature, and/or area) can be about 0.5% to about 500% larger in size and/or shape than the target cross-sectional size and/or shape, for example, to accommodate contraction that can occur during cooling of the textile 13 after having been heated and passed through a die hole, including every 0.5% increment within this range.

As yet another example, one or multiple dimensions of the die hole 19 (e.g., width, length, height, diameter, perimeter, radius of curvature, and/or area) can be about 0.5% to about 200% larger in size and/or shape than the target cross-sectional size and/or shape, for example, to accommodate contraction that can occur during cooling of the textile 13 after having been heated and passed through a die hole, including every 1% increment within this range.

As yet another example, one or multiple dimensions of the die hole 19 (e.g., width, length, height, diameter, perimeter, radius of curvature, and/or area) can be about 1% to about 25% larger in size and/or shape than the target cross-sectional size and/or shape, for example, to accommodate contraction that can occur during cooling of the textile 13 after having been heated and passed through a die hole, including every 1% increment within this range.

FIG. 2A further illustrates that the die hole 19 can have a width $W_1$. The width $W_1$ can be the diameter of the die hole 19. The width $W_1$ can be about 0.01 mm to about 50 mm, including every 0.01 mm increment within this range (e.g., 0.1 mm, 1 mm, 2 mm, 3 mm, 10 mm, 20 mm). The width $W_1$ can be about 0.1 mm to about 20 mm, including every 0.1 mm increment within this range (e.g., 0.1 mm, 1 mm, 2 mm, 3 mm, 10 mm, 20 mm).

FIG. 2A further illustrates that the heater 16 can have a heater length $L_1$. The heater length $L_1$ can be from about 1 mm to about 1000 mm or more, or more narrowly, from about 10 mm to about 500 mm or more, including every 1 mm increment within these ranges (e.g., 10 mm, 50 mm, 100 mm, 500 mm).

FIG. 2A further illustrates that the heater 16 and the die 18 can be separated by a gap $L_2$. The gap $L_2$ can be from about 0 mm to about 1000 mm or more, or more narrowly, from about 0 mm to about 500 mm or more, including every 1 mm increment within these ranges (e.g., 0 mm, 10 mm, 50 mm, 100 mm, 500 mm). As yet another example, the die 18 can be inside the chamber 17. As still yet another example, a die first portion having a die hole 19 can be in the chamber 17 and a die second portion can be outside the chamber 17. The die hole 19 of the die first portion can be inside the chamber 17.

FIG. 2A further illustrates that the die 18 can have a die length $L_3$. The die length $L_3$ can be from about 1 mm to about 1000 mm or more, or more narrowly, from about 1 mm to about 500 mm or more, including every 1 mm increment within these ranges (e.g., 1 mm, 5 mm, 10 mm, 25 mm, 50 mm, 100 mm, 500 mm). The length $L_3$ can be less than (as shown), equal to, or greater than the length $L_1$.

FIG. 2A further illustrates that the textile first portion 13a can have a length $L_4$. The length $L_4$ can be from about 1 mm to about 1000 mm or more, or more narrowly, from about 10 mm to about 500 mm or more, including every 1 mm increment within these ranges (e.g., 1 mm, 5 mm, 10 mm, 25 mm, 50 mm, 100 mm, 500 mm). The length $L_4$ can be less than, greater than (as shown), or equal to the length $L_1$.

FIG. 2A further illustrates that the textile second portion 13b can have a length $L_5$. The length $L_5$ can be from about 1 mm to about 100 mm or more, or more narrowly, from about 5 mm to about 50 mm or more, including every 1 mm increment within these ranges (e.g., 1 mm, 5 mm, 10 mm, 25 mm, 50 mm). The length $L_5$ can be less than, greater than, or equal to the length $L_4$.

FIG. 2A further illustrates that the textile third portion first section $13c_1$ can have the length $L_3$.

FIG. 2A further illustrates that the textile third portion second section $13c_2$ can have a length $L_6$. The length $L_6$ can be from about 1 mm to about 100 mm or more, or more narrowly, from about 1 mm to about 50 mm or more, including every 1 mm increment within these ranges (e.g., 1 mm, 5 mm, 10 mm, 25 mm, 50 mm).

FIG. 2A further illustrates that the textile third portion third section $13c_3$ can have a length $L_7$. The length $L_7$ can be from about 1 mm to about 100 mm or more, or more narrowly, from about 1 mm to about 50 mm or more, including every 1 mm increment within these ranges (e.g., 1 mm, 5 mm, 10 mm, 25 mm, 50 mm).

The lengths $L_3$, $L_6$, and $L_7$ of the textile third portion first, second, and third sections $13c_1$, $13c_2$, $13c_3$, respectively, can be the same or different from one another. The length $L_3$ can be less than or greater than $L_6$ and/or $L_7$. The length $L_6$ can be less than or greater than $L_3$ and/or $L_7$. The length $L_7$ can be less than or greater than $L_3$ and/or $L_6$.

The total length of the textile third portion 13c can have a length $L_8$. The length $L_8$ can be the sum of the lengths $L_3$, $L_6$, and $L_7$. The length $L_8$ can be less than, equal to, or greater than the length $L_4$. The length $L_8$ can be less than, greater than, or equal to the length $L_5$. The lengths $L_3$, $L_6$, $L_7$, and/or $L_8$ can be less than, equal to, or greater than the length $L_1$, $L_4$, and/or $L_5$, or any combination thereof.

The total length of the textile first, second, and third portions 13a, 13b, and 13c can have a length $L_9$. The length $L_9$ can be the sum of the lengths $L_4$, $L_5$, and $L_8$. As another example, length $L_9$ can be the sum of the lengths $L_3$, $L_4$, and $L_5$. As yet another example, length $L_9$ can be the sum of the lengths $L_3$, $L_4$, $L_5$, and $L_6$. The length $L_9$ can be from about 5 mm to about 5000 mm or more, or more narrowly, from about 5 mm to about 1000 mm or more, including every 1 mm increment within these ranges (e.g., 5 mm, 5 mm, 10 mm, 25 mm, 50 mm, 100 mm, 1000 mm).

FIG. 2A further illustrates that the textile first, second, and third portions 13a, 13b, 13c, or any combination thereof, can be heated by the heater 16 or can pass through or by the heater 16 without being heated by the heater 16. For example, FIG. 2A further illustrates that the heated portion of the textile 13 can be the textile first portion 13a, the textile second portion 13b, the textile third portion first section $13c_1$, the textile third portion second section $13c_2$, the textile third portion third section $13c_3$, or any combination thereof. As another example, FIG. 2A further illustrates that the non-heated portion of the textile 13 can be the textile first portion 13a, the textile second portion 13b, the textile third portion first section $13c_1$, the textile third portion second section $13c_2$, the textile third portion third section $13c_3$, or any combination thereof. As yet another example, FIG. 2A further illustrates that the non-heated portion of the textile 13 can be the textile first portion 13a and that the heated portion of the textile 13 can be the textile second portion 13b, the textile third portion first section $13c_1$, the textile third portion second section $13c_2$, the textile third portion third section $13c_3$. As still yet another example, FIG. 2A further illustrates that the heated portion of the textile 13 can be the textile first portion 13a and that the non-heated portion of the textile 13 can be the textile second portion 13b, the textile third portion first section $13c_1$, the textile third portion second section $13c_2$, the textile third portion third section $13c_3$.

FIG. 2A further illustrates that the textile 13 can be sized (e.g., cut) at a textile first location $T_{L1}$. The textile 13 can have a textile terminal distal end 38 such that when a textile portion 37 is sized (e.g., cut) from the textile 13, the new textile terminal distal end can be at the textile first location $T_{L1}$. The textile 13 can then be sized again, for example, at a textile second location $T_{L2}$ or at any location along the textile 13 between textile locations $T_{L1}$ and $T_{L2}$. The textile second location $T_{L2}$ can be a distance of about 0 mm to about 1000 mm or more from the chamber first end 17a, including every 1 mm increment within this range. The textile second location $T_{L2}$ can be a distance of about 0 mm to about 500 mm or more from the chamber first end 17a, including every 1 mm increment within this range. The textile second location $T_{L2}$ can be the same as or different from the textile location of the textile first portion first end $13a_1$.

The textile portion 37 can have a textile first portion 13a, a textile second portion 13b, a textile third portion first section $13c_1$, a textile third portion second section $13c_2$, a textile third portion third section $13c_3$, or any combination thereof. The textile portion 37 can be a suture having one or multiple portions having the first cross-sectional shape and/or size and one or multiple portions having the second cross-sectional shape and/or size. For example, the textile portion 37 can be a suture having one or multiple portions having a non-round (e.g., flat) cross-sectional shape and one or multiple portions having a round cross-sectional shape. The textile portion 37 can have a length $L_{10}$. The length $L_{10}$ can be from about 1 mm to about 5000 mm or more, including every 1 mm increment within this range (e.g., 1 mm, 5 mm, 10 mm, 25 mm, 50 mm, 100 mm, 1000 mm). The length $L_{10}$ can be from about 1 mm to about 1000 mm or more, including every 1 mm increment within this range (e.g., 1 mm, 5 mm, 10 mm, 25 mm, 50 mm, 100 mm, 1000 mm). The length $L_{10}$ can be less than, equal to, or greater than the length $L_9$.

The various lengths and length combinations disclosed herein (e.g., $L_1$-$L_{10}$) can desirably achieve the intended heating profile of the textile 13 and/or the intended cooling profiling of the textile 13 (i.e., after being heated) such that the textile first cross-sectional shape can be reliably and consistently changed to the textile second cross-sectional shape. The various lengths and length combinations disclosed herein (e.g., $L_1$-$L_{10}$) can desirably achieve the intended target length of the final suture (e.g., portion 37) having length $L_{10}$. Every combination of dimensions is thereby a critical combination of dimensions (e.g., $L_1$-$L_{10}$), including any dimensions chosen within the provided ranges.

The textile shaper 10 can create multiple textile portions 37 (e.g., sutures), each having one or multiple portions having the textile first cross-sectional shape (e.g., flat) and one or more portions having the textile second cross-sectional shape (e.g., non-flat). For example, each suture created by the textile shaper 10 can have 1 to 10 or flat portions, including every 1 unit increment within this range (e.g., 1 flat portion, 2 flat portions). As another example, each suture created by the textile shaper 10 can have 1 to 10 or more non-flat portions, including every 1 unit increment within this range (e.g., 1 non-flat portion, 2 non-flat portions). Each suture 37 created can have the length $L_{10}$. The length $L_{10}$ of each suture 37 created from the textile source 12 can be the same or different from one or multiple other sutures 37 created from the textile source 12.

Figure 2B:
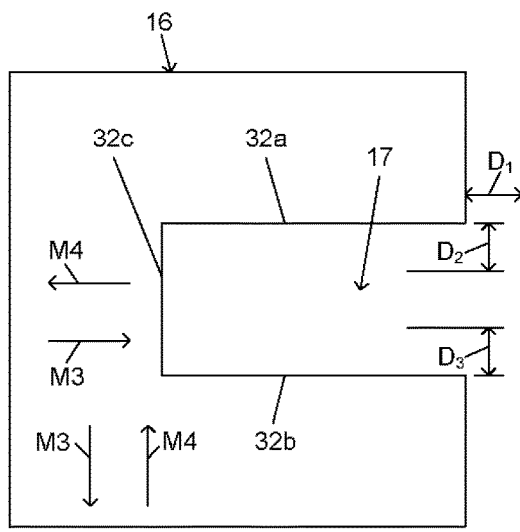
FIG. 2B illustrates the textile shaper of FIG. 2A taken along line 2B-2B with a variation of a textile outside of a variation of a heater.
Figure 2C:
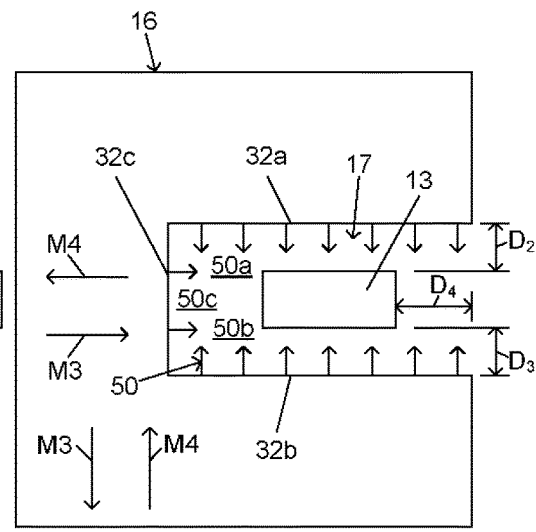
FIG. 2C illustrates the textile shaper of FIG. 2B with the textile inside the heater.

FIGS. 2B and 2C illustrate that the textile 13 and/or the heater 16 can be laterally movable, for example, perpendicular to the textile longitudinal axis, in a lateral first direction M3, in a lateral second direction M4 opposite the lateral first direction M3, or both. For example, FIG. 2B illustrates that the textile 13 can be moved laterally in the lateral first direction M3 (e.g., away from the surface 32c, out of the chamber 17) and FIG. 2C illustrates that the textile 13 can be moved laterally in the lateral second direction M4 (e.g., toward the surface 32c, into the chamber 17). As another example, FIG. 2B illustrates that the heater 16 can be moved laterally in the lateral second direction M4 (e.g., away from the textile 13) and FIG. 2C illustrates that the heater 16 can be moved laterally in the lateral first direction M3 (e.g., toward the textile 13). The textile 13 can move laterally (e.g., M3, M4) while the textile 13 is moving longitudinally (e.g., M1, M2) or when the textile is longitudinally stationary. The heater 16 can move laterally (e.g., M3, M4) while the heater 16 is moving longitudinally (e.g., M1, M2) or when the heater is longitudinally stationary. The heater 16 can be on or off when the textile 13 and/or the heater 16 are moving laterally (e.g., M3, M4).

FIGS. 2B and 2C further illustrate that the textile 13 and/or the heater 16 can be laterally movable, for example, perpendicular to the textile longitudinal axis, in a lateral third direction M5, in a lateral fourth direction M6 opposite the lateral third direction M4, or both. The lateral directions M5 and M6 can be perpendicular to the textile longitudinal axis. The lateral directions M5 and M6 can be perpendicular to the lateral directions M3 and M4. For example, FIGS. 2B and 2C illustrate that the textile 13 can be moved laterally in the lateral third direction M5, in the lateral fourth direction M6, or in both directions, for example, when the textile 13 is outside of the chamber 17 (FIG. 2B) or inside the chamber 17 (FIG. 2C). As another example, FIGS. 2B and 2C illustrate that the heater 16 can be moved laterally in the lateral third direction M5, in the lateral fourth direction M6, or in both directions, for example, when the textile 13 is outside of the chamber 17 (FIG. 2B) or inside the chamber 17 (FIG. 2C). The textile 13 can move laterally (e.g., M5, M6) while the textile 13 is moving longitudinally (e.g., M1, M2) or when the textile is longitudinally stationary. The heater 16 can move laterally (e.g., M5, M6) while the heater 16 is moving longitudinally (e.g., M1, M2) or when the heater is longitudinally stationary. The textile, heater, and/or die 13, 16, 18 can be moved in directions M1, M2, M3, M4, M5, M6, or any combination thereof.

FIGS. 2A-2C thereby illustrate that the heater 16 can be movable (e.g., advanceable, retractable, or both) toward and/or away from the textile 13.

FIG. 2B further illustrate that the heater 16 can be on or off (as shown) when the textile 13 is outside of the chamber 17 and FIG. 2C further illustrates that the heater 16 can be on (as shown) or off when the textile 13 is inside the chamber 17.

FIG. 2B further illustrates that the textile 13 and/or the heater 16 can be laterally moved such that the textile 13 can be a distance $D_1$ from the opening of the chamber 17. The distance $D_1$ can be from about 0 mm to about 100 mm, or more narrowly, from about 0 mm to about 50 mm, including every 1 mm increment within this range (e.g., 0 mm, 1 mm, 10 mm, 50 mm). As another example, the distance $D_1$ can extend into the chamber 17, for example, when some of the textile 13 (e.g., a lateral first side such as the left side in FIG. 2B) is in the chamber 17 and some of the textile 13 (e.g., a lateral second side such as the right side in FIG. 2B) is outside of the chamber 17.

FIG. 2B further illustrates that the textile 13 can be distances $D_2$ and $D_3$ from the chamber surfaces 32a and 32b, respectively. The distance $D_2$ can be from about 0 mm to about 100, or more narrowly, from about 0 mm to about 50 mm, including every 1 mm increment within these ranges (e.g., 0 mm, 1 mm, 10 mm, 50 mm). The distance $D_2$ can be 0 mm, for example, for a contact heater. The distance $D_3$ can be from about 0 mm to about 100 mm, or more narrowly, from about 0 mm to about 50 mm, including every 1 mm increment within these ranges (e.g., 0 mm, 1 mm, 10 mm, 50 mm). The distance $D_3$ can be 0 mm, for example, for a contact heater. The distance $D_2$ can be the same as or different from the distance $D_3$.

FIG. 2C further illustrates that the textile 13 and/or the heater 16 can be laterally moved such that the textile 13 can be a distance $D_4$ from the opening of the chamber 17. The distance $D_4$ can be from about 0 mm to about 500 mm, or more narrowly, from about 0 mm to about 200 mm, including every 1 mm increment within these ranges (e.g., 0 mm, 1 mm, 10 mm, 50 mm, 100 mm, 150 mm, 200 mm). As another example, the distance $D_4$ can extend out of the chamber 17, for example, when some of the textile 13 (e.g., a lateral first side such as the left side in FIG. 2B) is in the chamber 17 and some of the textile 13 (e.g., a lateral second side such as the right side in FIG. 2B) is outside of the chamber 17.

FIG. 2C further illustrates that the heater 16 (e.g., via or through first through third surfaces 32a-32c) can emit energy 50 (e.g. firth through third energies 50a-50c). The energy 50 can be emitted perpendicularly or at an angle from the surfaces 32. The first energy 50a can be emitted from the first surface 32a and can be directed toward the second surface 32b. The second energy 50b can be emitted from the second surface 32b and can be directed toward the first surface 32a. The third energy 50c can be emitted from the third surface 32c and can be directed toward the opening of the chamber 17. The energy emitted from a surface 32 (e.g., surface 32a) can be the same magnitude as or a different magnitude from the energy emitted from another surface 32 (e.g., surface 32b). For example, the energy emitted 50 can be emitted at about 10 J/s to about 3000 J/s, or more narrowly, at about 50 J/s to about 1500 J/s, including every 1 J/s increment within these ranges.

FIGS. 2B and 2C further illustrate that the first cross-sectional shape of the textile 13 can be flat (e.g., rectangular).

FIGS. 3A and 3B illustrates that the die 18 can have first through eighth holes 19a-19h. FIG. 3A further illustrates that the adjacent holes 19 can be separated by an angle $A_1$. The angle $A_1$ can be from about 2 degrees to about 359 degrees, including every 1 degree increment within this range (e.g., 45 degrees). The angle $A_1$ can be from about 10 degrees to about 180 degrees, including every 1 degree increment within this range (e.g., 45 degrees). The die can have a width $D_5$. The width $D_5$ can be a diameter. The width $D_5$ can be about 1 cm to about 200 cm, or more narrowly, about 5 cm to about 100 cm, including every 1 cm increment within these ranges (e.g., 25 cm). FIG. 3A further illustrates that the die holes 19 can have the cross-sectional shape desired for the textile second cross-sectional shape. For example, FIG. 3A illustrates that the die holes 19 can have a non-flat (e.g., circular) cross-sectional shape having a die hole radius of curvature 21. The die hole radius of curvature 21 can be about 0.10 mm to about 100.00 mm, or more narrowly, about 0.50 mm to about 15.00 mm, including every 0.01 mm increment within these ranges (e.g., 0.50 mm, 1.00 mm, 5.00 mm, 10.00 mm, 15.00 mm).

FIGS. 3C and 3D illustrate that the die holes 19 can be slots. The die 18 can have, for example, first through eighth slots 19a-19h. The slots 19 (e.g., slots 19a-19h) can have slot ends 23. The slot ends 23 can be flat or curved. For example, the slot ends 23 can be define an arc of a circle. The arc can have a radius of curvature desired for the textile second cross-sectional shape. The radius of curvature 25 of the arc defining the end 23 can be about 0.01 mm to about 30.00 mm, or more narrowly, about 0.50 mm to about 5.00 mm, including every 0.01 mm increment within these ranges). Where slots 19 are used, the heated and non-heated portions of the textile 13 can pass through the die 18. As another example, where slots 19 are used, the heated portions of the textile 13 can pass through the die 18 and the non-heated portions of the textile 13 can bypass the die 18, for example, by moving the die 18 away from the textile 13, by moving the textile 13 out of the die 18, or both.

Figure 4A:
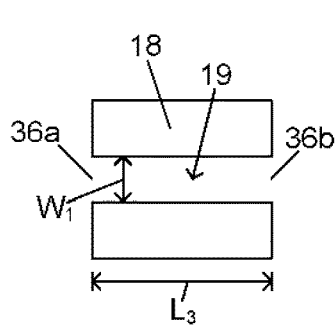
FIG. 4A illustrates a variation of a cross-section of a die hole of FIG. 3B taken along line 4A-4A.
Figure 4B:
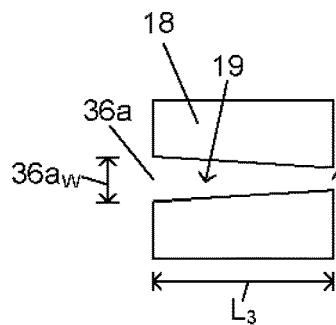
FIG. 4B illustrates a variation of a cross-section of a die hole of FIG. 3B taken along line 4B-4B.
Figure 4C:
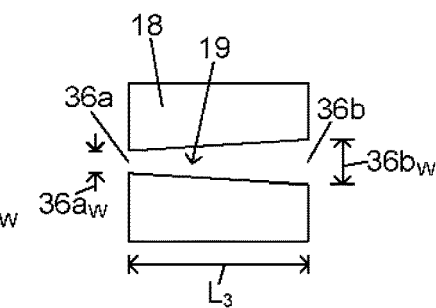
FIG. 4C illustrates a variation of a cross-section of a die hole of FIG. 3B taken along line 4C-4C.

FIGS. 4A-4C illustrate that one or multiple of the die holes 19 can be non-tapered, tapered, or both, for example, from a die hole first end 36a (also referred to as the textile inlet) to a die hole second end 36b (also referred to as the textile outlet). As another example, the die hole first end 36a can be the textile outlet and the die hole second end 36b can be the textile inlet. The die hole first end 36a can be the same or different size and/or shape as the die hole second end 36b. For example, the textile inlet and outlet 36a, 36b can be circular. As another example, the textile inlet 36a can be non-circular (e.g., flat such as rectangular-, stadium-, or elliptical-shaped). The die holes 19 can have a cylindrical shape. The die holes 19 can have a conical shape, including conical, truncated-conical, or frusto-conical. The die holes 19 can have a polyhedral shape, including polyhedral, truncated-polyhedral, or frusto-polyhedral. The die holes 19 can have a pyramidal shape, including pyramidal, truncated-pyramidal, or frusto-pyramidal. The one or multiple die holes 19 can have the same or different shapes relative to one another.

FIG. 4A further illustrates that one or multiple of the die holes 19 (e.g., die hole 19b) can have a constant cross-sectional size and/or shape from the die hole first end 36a to the die hole second end 36b. For example, FIG. 4A illustrates that one or multiple of the die holes 19 (e.g., die holes 19a-19h) can have a cylindrical shape. The textile inlet and textile outlet 36a, 36b can have the width $W_1$. The width $W_1$ can be the largest cross-sectional dimension (e.g., the diameter) of the die hole 19.

FIG. 4B further illustrates that one or multiple of the die holes 19 (e.g., die hole 19c) can have a tapered cross-sectional size and/or shape. FIG. 4B further illustrates that the textile inlet 36a can be smaller than the textile outlet 36b. The textile inlet 36a can have a textile inlet width $36a_w$ and the textile outlet 36b can have a textile outlet width $36b_w$. The textile inlet width $36a_w$ can be the largest cross-sectional dimension (e.g., the diameter) of the textile inlet 36a. The textile inlet width $36a_w$ can be about 0.01 mm to about 50.00 mm, including every 0.01 mm increment within this range (e.g., 0.1 mm, 1 mm, 2 mm, 3 mm, 10 mm, 20 mm). The textile inlet width $36a_w$ can be about 0.1 mm to about 20.0 mm, including every 0.1 mm increment within this range (e.g., 0.1 mm, 1 mm, 2 mm, 3 mm, 10 mm, 20 mm). The textile outlet width $36b_w$ can be the largest cross-sectional dimension (e.g., the diameter) of the textile outlet 36b. The textile outlet width $36b_w$ can be about 0.01 mm to about 50.00 mm, including every 0.01 mm increment within this range (e.g., 0.1 mm, 1 mm, 2 mm, 3 mm, 10 mm, 20 mm). The textile outlet width $36b_w$ can be about 0.1 mm to about 20.0 mm, including every 0.1 mm increment within this range (e.g., 0.1 mm, 1 mm, 2 mm, 3 mm, 10 mm, 20 mm). The textile outlet width $36b_w$ can be about 0.01 mm to about 49.99 mm smaller than the textile inlet width $36a_w$, including every 0.01 mm increment within this range. The textile outlet width $36b_w$ can be about 0.1 mm to about 19.9 mm smaller than the textile inlet width $36a_w$, including every 0.1 mm increment within this range. As another example, the textile outlet width $36b_w$ can be about 0.5% to about 1000% smaller than the textile inlet width $36a_w$. As another example, the textile outlet width $36b_w$ can be about 1% to about 200% smaller than the textile inlet width $36a_w$. FIG. 4B further illustrates that one or multiple of the die holes 19 (e.g., die holes 19a-19h) can have a frusto-conical shape. A large-to-small tapered die hole 19 can advantageously lessen the shock to the textile 13 when changing from the first cross-sectional shape to the second cross-sectional shape, for example, as compared to a die hole 19 having a constant cross-sectional size. This is because a tapered cross-section can allow more time for the heated and/or non-heated material of the textile to change dimensions when going through the die 18.

FIG. 4C further illustrates that one or multiple of the die holes 19 (e.g., die hole 19d) can have a tapered cross-sectional size and/or shape. FIG. 4C further illustrates that the textile inlet 36a can be larger than the textile outlet 36b. The textile outlet width $36b_w$ can be about 0.01 mm to about 49.99 mm larger than the textile inlet width $36a_w$, including every 0.01 mm increment within this range. The textile outlet width $36b_w$ can be about 0.1 mm to about 19.9 mm larger than the textile inlet width $36a_w$, including every 0.1 mm increment within this range. As another example, the textile outlet width $36b_w$ can be about 0.5% to about 1000% larger than the textile inlet width $36a_w$. As another example, the textile outlet width $36b_w$ can be about 1% to about 200% larger than the textile inlet width $36a_w$. FIG. 4C further illustrates that one or multiple of the die holes 19 (e.g., die holes 19a-19h) can have a frusto-conical shape. A small-to-large tapered die hole 19 can advantageously take advantage of material rebound properties, and/or control the rebound rate of the material after having been contracted, compressed, or folded to fit into the die hole 19.

The die holes 19 in FIGS. 4A-4C can be connected end-to-end in any combination, for example, in 4A-4B, 4B-4A, 4A-4C, 4C-4A, 4B-4C, 4C-4B combinations, and in any three way combination such as 4A-4B-4C, 4B-4A-4B, and 4B-4A-4C.

Figure 4D:
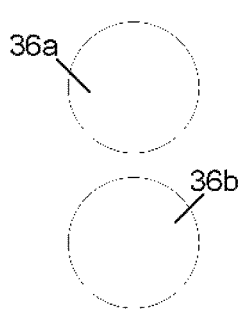
FIG. 4D illustrates a variation of a die hole entrance and a variation of a die hole exit.
Figure 4E:
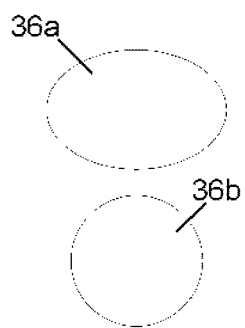
FIG. 4E illustrates a variation of a die hole entrance and a variation of a die hole exit.
Figure 4F:
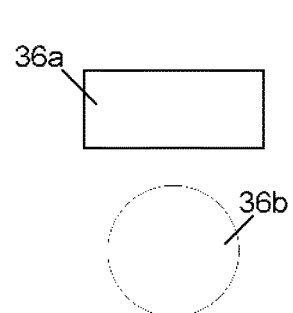
FIG. 4F illustrates a variation of a die hole entrance and a variation of a die hole exit.

FIGS. 4D-4F illustrate various cross-sectional shapes that the textile inlet and textile outlet 36a, 36b can have. FIG. 4D illustrates that the cross-sectional shape of the textile inlet and outlet 36a, 36b can be the same, for example, circular. FIGS. 4E and 4F illustrate that the cross-sectional shape of the textile inlet and outlet 36a, 36b can be different from one another. For example, FIG. 4E illustrates that the textile inlet 36a can have a flat (e.g., elliptical) cross-sectional shape and that the textile outlet 36b can have a rounded (e.g., circular) cross-sectional shape. As another example, FIG. 4F illustrates that the textile inlet 36a can have a flat (e.g., rectangular) cross-sectional shape and that the textile outlet 36b can have a rounded (e.g., circular) cross-sectional shape. Where the cross-sectional shape of the textile inlet and outlet 36a, 36b are different from one another, the channel 19 can taper from the inlet cross-sectional shape to the outlet cross-sectional shape along the longitudinal length of the die channel 19.

FIGS. 4A-4F further illustrate that the cross-sectional area of the textile inlet 36a can be less than, equal to, or greater than the cross-sectional area of the textile outlet 36b.

The cross-sectional size and/or shape of the textile outlet 36b can be the same as the target cross-sectional size and/or shape for the textile second cross-sectional shape. Having a different shaped inlet and outlet 36a, 36b can reduce the strain on the textile 13 or spread the strain over a greater time interval as the textile 13 is folded, expanded, and/or contracted into a new cross-sectional size and/or shape such as the size and/or shape of the textile outlet 36b or another portion of the die hole 19 between the inlet and outlet 36a, 36b. This can advantageously create a uniform cross-sectional size and/or shape for the portions of the textile 13 that have been heated.

FIGS. 4A-4F further illustrate that the cross-sectional area of the textile inlet 36a can be less than, equal to, or greater than the cross-sectional area of the textile first cross-sectional shape.

FIGS. 4A-4F further illustrate that the textile inlet width $36a_w$ can be larger than the largest cross-sectional dimension of the textile 13, for example, about 0.01 to about 10.00 mm, or more narrowly, about 0.01 to about 2.00 mm larger than the textile inlet width $36a_w$, including every 0.01 mm increment within these ranges.

FIGS. 4A-4F further illustrate that the textile inlet cross-sectional area can be larger than the cross-sectional area of the textile first cross-sectional shape, for example, about 0.05 mm$^2$ to about 10.00 mm$^2$ larger, or more narrowly, about 0.25 mm$^2$ to about 4.0 mm$^2$ larger than the cross-sectional area of the textile first cross-sectional shape, including every 0.1 mm$^2$ increment within these ranges.

FIGS. 4A-4F further illustrate that the textile inlet width $36a_w$ can be smaller than the largest cross-sectional dimension of the textile 13, for example, about 0.01 to about 10.00 mm smaller, or more narrowly, about 0.01 to about 2.00 mm smaller than the textile inlet width $36a_w$, including every 0.01 mm increment within these ranges.

FIGS. 4A-4F further illustrate that the textile inlet cross-sectional area can be smaller than the cross-sectional area of the textile first cross-sectional shape, for example, about 0.05 mm$^2$ to about 10.0 mm$^2$ smaller, or more narrowly, about 0.25 mm$^2$ to about 4.0 mm$^2$ smaller than the cross-sectional area of the textile first cross-sectional shape, including every 0.1 mm$^2$ increment within these ranges.

The die holes 19 can have a fixed shape or an adjustable shape. Some die holes 19 can have a fixed shape and some die holes 19 can have an adjustable shape. The die holes 19 can have a fixed size or an adjustable size. Some die holes 19 can have fixed size and some die holes 19 can have an adjustable size. For example, the die hole 19 can be an adjustable aperture that can be openable and closeable. When the die hole 19 is closed, die hole can be partially or completely closed. Having one or multiple die holes 19 that can open and close like an aperture can allow the die hole cross-sectional size and/or shape to be changed without removing the textile 13 from the die 18.

FIGS. 4A-4C further illustrate that the die hole 19 can be curved, for example, into or out of the plane of the figure.

FIGS. 5A-5C illustrate that the textile portion 37 (e.g., a suture 37) can have one or multiple sections 38 having the textile first cross-sectional shape (e.g., flat) and one or multiple sections 40 having the textile second cross-sectional shape (e.g., non-flat such as round or rounded). The suture 37 can have 1-10 or more sections 38, including every 1 section 38 increment within this range (e.g., 1, 2, 10 sections 38). The suture 37 can have 1-10 or more sections 40, including every 1 section 40 increment within this range (e.g., 1, 2, 10 sections 40). A flat section 38 can be between two adjacent non-flat sections 40. All or a portion of the cross-sectional shape can be rounded, for example, relative to the textile first cross-sectional shape. A rounded section 40 can be between two adjacent non-rounded sections 38. The sections 38 can be flat braid suture portions having a rectangular cross-sectional shape. One, two, three, or all four of the corners of the rectangular cross-section can be curved.

FIG. 5A illustrates that the suture 37 can have a non-flat suture first end 40a, a non-flat suture second end 40b, and a flat suture middle 38a.

FIG. 5B illustrates that the suture 37 can have a flat suture first end 38a, a flat suture second end 38b, and a non-flat suture middle 40.

FIG. 5C illustrates that the suture 37 can have a transition section 39 between a section 38 and a section 40. The transition section 39 can have melted textile, non-melted textile, or both. The transition section 39 can be folded. The transition section 39 can have a taco shape. For example, the transition section 39 can define a seam 39s. The seam 39s can be an open seam. The transition section 39 can progressively unfold from the section 40 to the section 38. For example, FIG. 5C illustrates that the transition section 39 can have a first lip 49a and a second lip 49b folded toward one another. The lips 49a and 49b can progressively become smaller from the section 40 to the section 38.

FIG. 5C further illustrates that the suture 37 can have a flat suture end 38 and a round suture end 40.

Figure 6A:
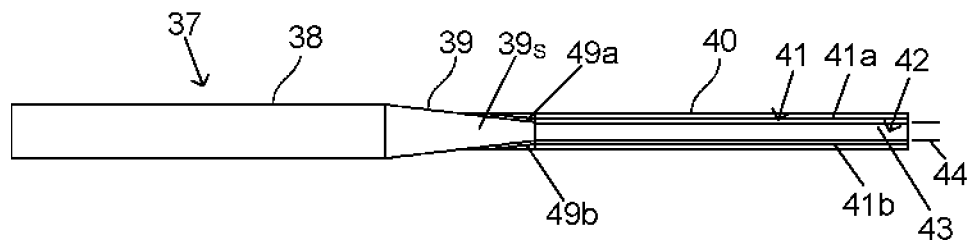
FIG. 6A illustrates a top or bottom view of a variation of a suture.
Figure 6B:
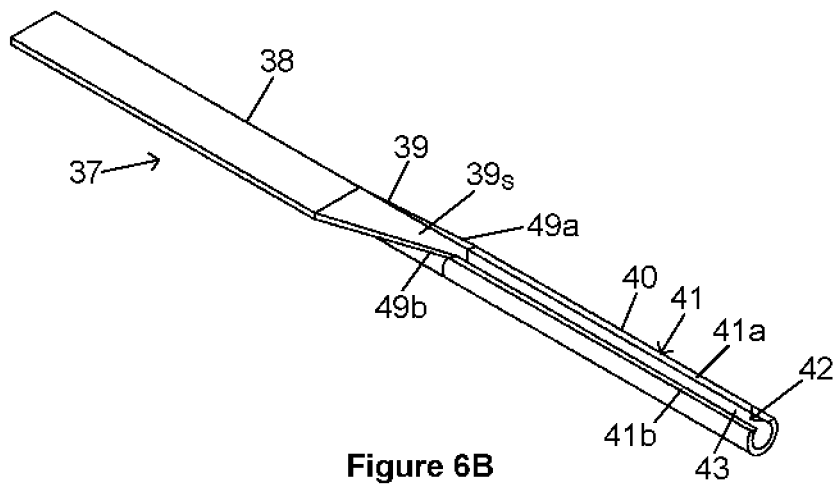
FIG. 6B illustrates a perspective view of the suture of FIG. 6A.
Figure 6C:
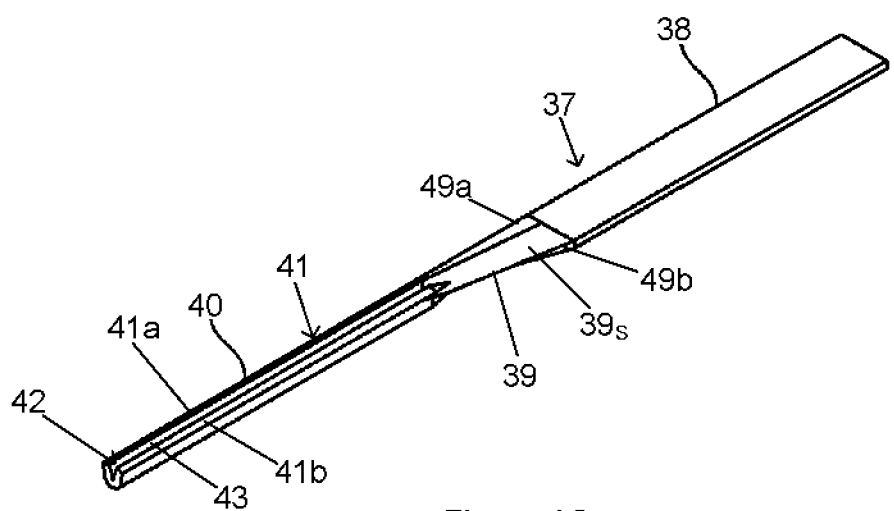
FIG. 6C illustrates a perspective view of a variation of a suture.

FIGS. 6A-6C illustrate that the section 40 can be folded or can have a bend. FIGS. 6A-6C illustrate that the section 40 can have one or multiple edges 41 (also referred to as sides). The edges 41 can be straight or curved. The edges 41 can be curled edges. For example, the section 40 can have a first curled edge 41a and a second curled edge 41b. The first and second curled edges 41a, 41b can contact one another. As another example, the first and second curled edges 41a, 41b can be separated by channel 42. The channel 42 can have a channel width 44, for example, perpendicular to the textile longitudinal axis. The channel width 44 can be about 0.0 mm to about 25.0 mm, or more narrowly, about 0.0 mm to about 10.0 mm, including every 0.1 mm increment within these ranges (e.g., 0.0 mm, 0.1 mm, 2.5 mm, 5.0 mm, 7.5 mm, 10.0 mm). The section 40 can have one or multiple channels 42. Each channel 42 can define a longitudinal opening 43. The opening 43 can have an opening width, for example, perpendicular to the textile longitudinal axis. The opening width can be the channel width 44. The fold of the textile 13 in the section 40 can be, for example, a C-shaped fold, a U-shaped fold, a V-shaped fold, an M-shaped fold, a W-shaped fold, an S-shaped fold, a Z-shaped fold, or an irregular-shaped fold. C-, U-, and V-shaped folds can define one channel 42 (e.g., between the legs of the "C", "U", and "V"). S- and Z-shaped folds can define two channels 42 (e.g., where the ends of the "S" circle back toward the center of the "S"). M- and W-shaped folds can define three channels 42 (e.g., between the legs and peaks of the "M" and "W").

FIG. 6B further illustrates that the section 40 can have a C-shaped transverse cross-sectional shape.

FIG. 6C further illustrates that the section 40 can have a V-shaped cross-sectional shape.

FIGS. 5C-6C further illustrate that a section 38 can define a first longitudinal terminal end of the suture 37 and a section 40 can define a second longitudinal terminal end of the suture 37.

FIGS. 5C-6C further illustrate that the suture 37 can have one section 38, one transition section 39, and one section 40. The section 38 can define a first longitudinal terminal end of the suture 37 and the section 40 can define a second longitudinal terminal end of the suture 37.

Figure 7A:
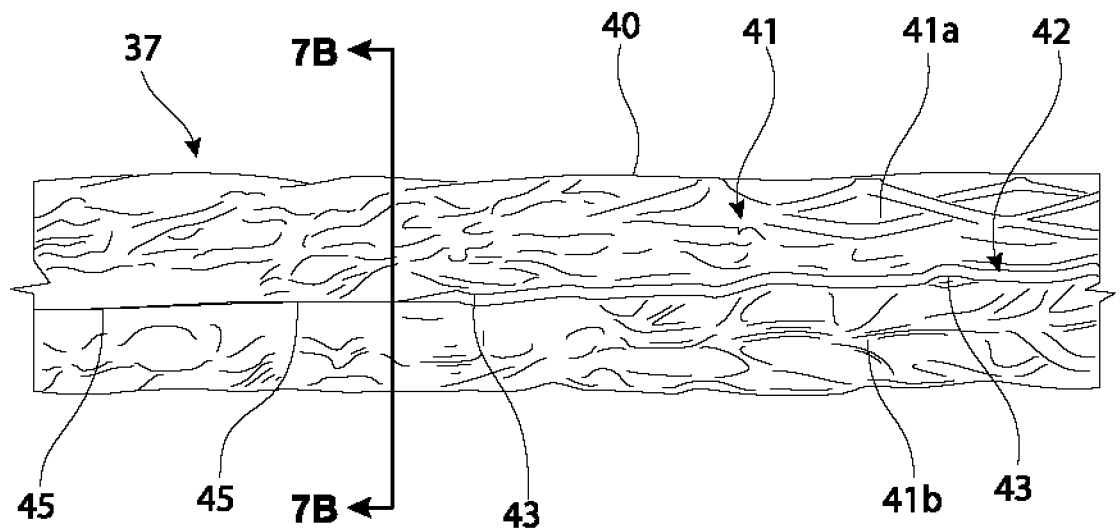
FIG. 7A illustrates a variation of a suture.

FIG. 7A illustrates that the section 40 can have a seam 45. The seam 45 can be where the first and second curled edges 41a, 41b contact each other. The perimeter of the cross-sectional shape of the section 40 can be closed where the seam 45 is located, for example, where the two sides (e.g., sides 41a, 41b) of the section 40 contact each other. The perimeter of the cross-sectional shape of the section 40 can be open where there is an opening (e.g., opening 42) between the two sides (e.g., sides 41a, 41b) of the section 40. One or multiple section 40 first portions can have a seam 45 (i.e., no opening 43) and one or multiple section 40 second portions can have an opening 43 (i.e., no seam 45). For example, FIG. 7A illustrates that the section 40 can have a section 40 first portion having a seam 45 and a closed perimeter to the left of the 7B-7B cross-section indicator and a section 40 second portion having an opening 43 and an open perimeter to the right of the 7B-7B cross-section indicator.

Figure 7B:
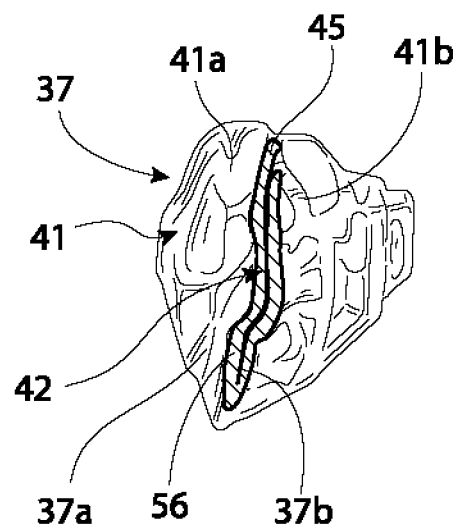
FIG. 7B illustrates a variation of a cross-section of the suture of FIG. 7A taken along line 7B-7B.

FIG. 7B illustrates that the section 40 can have a circular cross-sectional shape having a closed perimeter. The cross-sectional shape of the section 40 can be closed in the portions having the seam 45 and open in the portions having the opening 43.

FIG. 7B illustrates that the section 40 can have an elliptical cross-sectional shape having a closed perimeter. The cross-sectional shape of the section 40 can be closed in the portions having the seam 45 and open in the portions having the opening 43.

FIG. 7B further illustrates that the section 40 can be folded into an open C-shape, a closed C-shape (as shown), an open U-shape, a closed U-shape, an open V-shape, a closed V-shape, an open M-shape, a closed M-shape, an open W-shape, a closed W-shape, an open S-shape, a closed S-shape, an open Z-shape, a closed Z-shape, an open irregular-shape, or a closed irregular-shape. The cross-sectional shape of the section 40 (also referred to as the textile second cross-sectional shape) can be closed where ends of the suture 37 (e.g., sides 41a, 41b) contact each other (as shown at seam 45), where an end contacts a fold (e.g., the bent portion opposite the sides 41a and 41b), or both. The cross-sectional shape of the section 40 can be open where ends of the suture 37 (e.g., sides 41a, 41b) do not contact each other (as shown at opening 43), where an end does not contact a fold, or both. The section 40 can have one or multiple openings 43, one or multiple seams 45, or both.

FIG. 7B further illustrates that the section 40 can have a fold 56. The fold 56 can be open or closed. The fold 56 can be an open fold, for example, where there is an opening (e.g., opening 43) between the sides 41a and 41b. The fold 56 can be a closed fold, for example, where there is a seam (e.g., seam 45) between the sides 41a and 41b. For example, the fold 56 can have an open C-shape, a closed C-shape (as shown), an open U-shape, a closed U-shape, an open V-shape, a closed V-shape, an open M-shape, a closed M-shape, an open W-shape, a closed W-shape, an open S-shape, a closed S-shape, an open Z-shape, a closed Z-shape, an open irregular-shape, or a closed irregular-shape. The fold 56 can have a partially open or completely open shape. The fold 56 can have a partially closed or completely closed shape. The closed portion can be where ends of the suture 37 (e.g., sides 41a, 41b) contact each other (as shown at seam 45), where an end contacts a fold (e.g., the bent portion opposite the sides 41a and 41b), or both. The open portion can be where ends of the suture 37 (e.g., sides 41a, 41b) do not contact each other (as shown next to opening 43), where an end does not contact a fold, or both. The sides 41 (e.g., 41a, 41b) can be curved. For example, the sides 41 of C-, V-, U-, M-, W-, S-, Z-, and irregular-shaped folds 56 can be curved (e.g., the sides or legs extending from the apexes in these folds can be straight and/or curved).

FIG. 7B further illustrates that the section 40 can have the channel 42 when the section 40 has a closed fold (as shown), an open fold, or both. As another example, the sides 41a and 41b can be forced against each other such that there is no channel 42 in the textile second cross-cross-sectional shape.

FIG. 7B further illustrates that the suture 37 can be made of a first material 37a (light shading) and a second material 37b (dark shading). The first and second materials 37a, 37b can be melted together such that the boundaries of the fibers or filaments made of the first material 37a and the boundaries of the fibers or filaments made of the second material 37b can be melted together, for example, when the heater 16 heated the textile 13. The first material 37a can mix with the second material 37b when the textile 13 is in a melted phase such that some or all of the individual fibers or filaments of the heated section (e.g., rounded section 40) can melt into another fiber or filaments and coalesce and become a larger unified fibers, filaments, or melted and then hardened textile structures.

FIGS. 5A-7B further illustrate that the section 40 can be straight. The section 40 can be not pre-curved or it can be pre-curved. For example, FIGS. 5A-7B further illustrate that the section 40 can harden along a straight longitudinal axis such that the section 40 does not have a bias to curve.

FIGS. 5A-7B further illustrate that the section(s) 38 and that the section(s) 40 can be flexible such that the textile portion 37 can be used as a suture. The section(s) 38 can be softer than the section(s) 40, for example, because the section(s) 40 may not have been heated into a melt (e.g., liquid) phase and then cooled back to a solid phase.

Figure 8A:
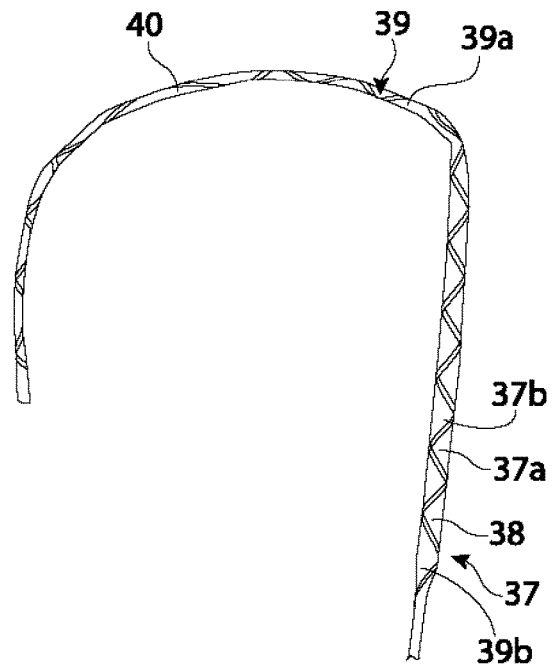
FIG. 8A illustrates a variation of a suture.

FIG. 8A illustrates that the section 40 can be pre-curved, for example, using a die 18 having a curved die channel 19. The radius of curvature of the curved section of the rounded section can be about 1 mm to about 100 mm, or more narrowly, about 5 mm to about 25 mm, including every 1 mm increment within these ranges (e.g., 5 mm, 10 mm, 25 mm). FIG. 8A further illustrates that the section 40 can harden along a curved longitudinal axis such that the section 40 has a bias to be in a curved shape. The die 18 having the curved die channel 19 can be separate from the die 18 having the die holes 18. The texture 13 (e.g., the heated portions) can be moved through the curved die channel 19 before or after going through a die hole 19.

FIG. 8A further illustrates that the suture 37 can have multiple transition sections 39, for example, a first transition section 39a and a second transition section 39b.

Figure 8B:
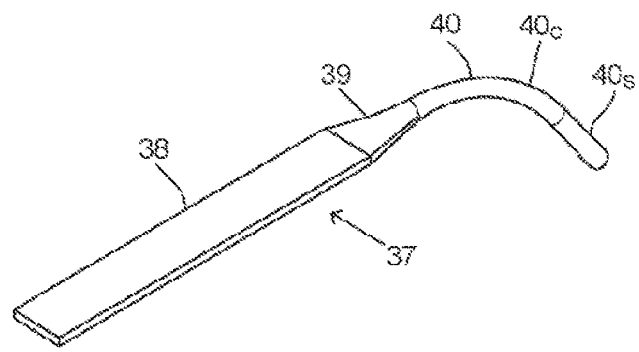
FIG. 8B illustrates a variation of a suture.

FIG. 8B illustrates that the section 40 can have a section 40 curved portion 40c, a section 40 straight portion 40s, or both. The shape of the suture 37 in FIG. 8B can be the relaxed shape of the suture 37. FIG. 8B further illustrates that the section 40 can harden in a curved longitudinal shape (e.g., section 40 curved portion) and a straight longitudinal shape (e.g., section 40 straight portion). The section curved portion 40c can be the tip of the suture 37. The section straight portion 40s can be the tip of the suture 37.

FIG. 8B further illustrates that the transition section 39 may be not folded. FIG. 8B further illustrates that the transition section 39 may have no lip 49a and/or no lip 49b.

Figure 9A:
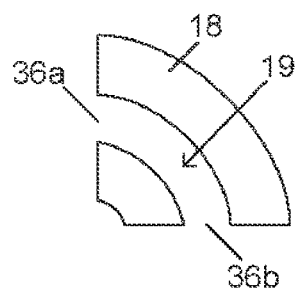
FIG. 9A illustrates a variation of a cross-section of die hole.

FIG. 9A illustrates that the die 18 can have one or multiple curved die holes 19. The radius of curvature of the die hole can be about 1 mm to about 100 mm, or more narrowly, about 5 mm to about 25 mm, including every 1 mm increment within these ranges (e.g., 5 mm, 10 mm, 25 mm).

Figure 9B:
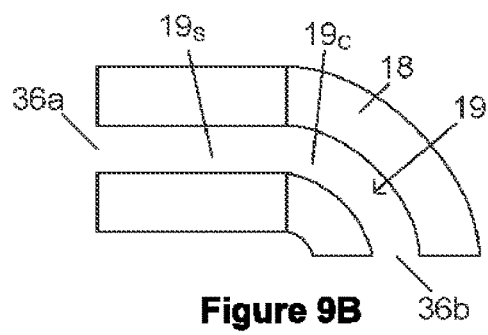
FIG. 9B illustrates a variation of a cross-section of die hole.

FIG. 9B further illustrates that the die 18 can have one or multiple die holes 19 with a curved portion 19c, a straight portion 19s, or both. The die hole straight portion 19s can be before (as shown) or after the die hole curved portion 19c.

FIGS. 9A and/or 9B can be the cross-section of the die hole 19, for example, taken along line 4A-4A, line 4B-4B, or line 4C-4C of FIG. 3B.

Figure 9C:
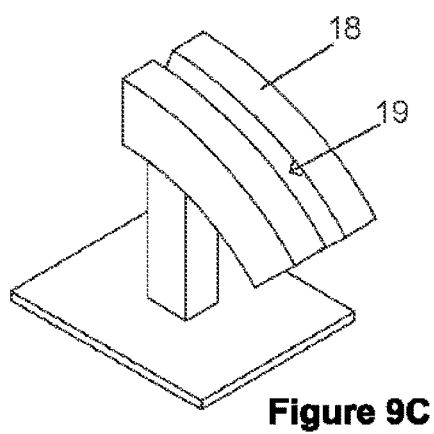
FIG. 9C illustrates a variation of a die.
Figure 9D:
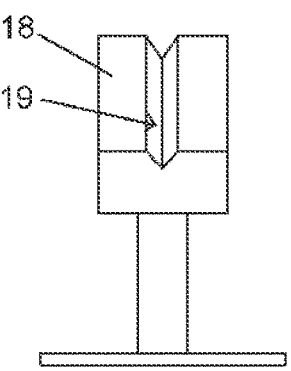
FIG. 9D illustrates a variation of a die.

FIGS. 9C and 9D illustrate that the die hole 19 can be a curved groove.

FIGS. $10A_1$-$10B_3$ illustrate that the textile shaper 10 can change a textile first cross-sectional size and/or shape 52 to a textile second cross-size size and/or shape 54. For example, the heater and the die 16, 18 can change the textile first cross-sectional shape 52 to the textile second cross-sectional shape 54. The heater 16 can heat the textile 13 and the die 18 can shape the heated textile. For example, the heater 16 can heat the textile 13 so that the heated portion of the textile 13 can partially or completely remain in the new shape (i.e., the cross-sectional shape of the die hole 19) after passing through the die 18 and cooling down. When in a heated phase, the material of the textile 13 can be melted (e.g., partially or completely) such that the textile material can flow. When in a heated phase, the material of the textile 13 can be malleable. The heater 16 can heat the textile 13 such that portions of the textile 13 (e.g., to-be-shaped portions) transition from a solid to a fluid. When in a heated state, the heated portion of the textile 13 can be deformed from the textile first cross-sectional size 52 to the textile second cross-sectional size 54. As another example, when in a fluid state, the heated portion of the textile 13 can be deformed from the textile first cross-sectional shape 52 to the textile second cross-sectional shape 54.

When the textile 13 passes through the die 18 (e.g., through a die hole 19), the die 18 can change the cross-sectional size and/or shape of the textile 13 from the textile first cross-sectional shape 52 to the textile second cross-sectional shape 54. The material of the textile 13—for example, the material of a first fiber or filament of the textile 13 and the material of a second fiber or filament of the textile 13—can flow and/or stick together while passing through the die 18. The heater 16 can increase the temperature of the to-be-shaped section(s) to a melt temperature such that the to-be-shaped section(s) can be melted and then cooled back to a solid phase. When melted, the material of the textile 13 can flow. The material of the first fiber or filament can be the same as or different from the material of the second fiber or filament.

The heated portion of the textile 13 that passes through the die 18 can harden in the textile second cross-sectional shape 54. Before passing through the die 18, the textile 13 can have the textile first cross-sectional shape 52. After passing through the die 18, the textile 13 (e.g., textile portion 37) can have the textile first and second cross-sectional shapes 52, 54. For example, after passing through the die 18, the textile (e.g., suture 37) can have one or multiple portions having the textile first cross-sectional shape 52 and one or multiple portions having the textile second cross-sectional shape 54. The portion(s) of the textile 13 (e.g., suture 37) heated prior to or while passing through the die 18 can have the textile second cross-sectional shape 54 after passing through the die 18, for example, because the heated portion(s) (e.g., the sides 41) can stick together such that the previously heated portions of the suture 37 can harden in the second cross-sectional shape 54.

FIGS. $10A_1$-$10A_3$ further illustrate, for example, that the textile 13 (e.g., textile portion 37) can have the textile first size and/or shape 52 before the textile 13 is passed through the die 18.

FIGS. $10A_1$-$10A_3$ further illustrate, for example, that the textile 13 (e.g., textile portion 37) can have the textile first cross-sectional shape 52 before and/or after the textile 13 is passed through the die 18.

FIGS. $10A_1$-$10A_3$ further illustrate the textile first cross-sectional shape 52 can be flat or non-flat. The textile first cross-sectional shape 52 can be flat and the textile second cross-sectional shape 54 can be non-flat. As another example, the textile first cross-sectional shape 52 can be non-flat and the textile second cross-sectional shape 54 can be non-flat.

FIG. $10A_1$ further illustrates that the textile first cross-sectional shape 52 can be rectangular. The textile first cross-sectional shape 52 can be a rectangle with angled (e.g., square) corners and/or round corners. For example, FIG. $10A_1$ illustrates that the textile first cross-sectional shape 52 can be a rectangle with right-angle corners. The textile first cross-sectional shape 52 can have a textile first cross-sectional shape first dimension $L_{12a}$ and a textile first cross-sectional shape second dimension $L_{11a}$. The textile first cross-sectional shape first dimension $L_{12a}$ can be about 0.1 mm to about 5.0 mm, or more narrowly, about 0.1 mm to about 2.5 mm, including every 0.1 mm increment within these ranges (e.g., 0.1 mm, 1.0 mm, 2.5 mm). The textile first cross-sectional shape second dimension $L_{11a}$ can be about 1.0 mm to about 20.0 mm, or more narrowly, about 1.0 mm to about 10.0 mm, including every 0.1 mm increment within these ranges (e.g., 1.0 mm, 2.5 mm, 10.0 mm). The dimension $L_{11a}$ can be about 1.0 mm to about 15.00 mm larger, or more narrowly, about 1.0 mm to about 7.50 mm larger than the dimension $L_{12a}$, including every 0.01 mm increment within this range. As another example, the dimension $L_{11a}$ can be about 10% to about 1000% larger, or more narrowly, about 50% to about 500% larger than the dimension $L_{12a}$, including every 5% increment within these ranges.

FIG. $10A_2$ further illustrates that the textile first cross-sectional shape 52 can have a stadium-shape.

FIG. $10A_3$ further illustrates that the textile first cross-sectional shape 52 can have an oblong, elliptical, or irregular shape. FIG. $10A_3$ further illustrates that the textile first cross-sectional shape can be flat or non-flat.

FIGS. $10B_1$-$10B_3$ further illustrate, for example, that the textile 13 (e.g., textile portion 37) can have the textile second cross-sectional shape 54 after the textile 13 is passed through the die 18.

FIG. $10B_1$ further illustrates that the textile second cross-sectional shape can be circular. The textile second cross-sectional shape first dimension $L_{12b}$ can be about 0.1 mm to about 20.0 mm, or more narrowly, about 0.5 mm to about 10.0 mm, including every 0.1 mm increment within these ranges (e.g., 0.1 mm, 1.0 mm, 2.5 mm, 7.5 mm, 10.0 mm). The textile second cross-sectional shape second dimension $L_{11b}$ can be about 0.1 mm to about 20.0 mm, or more narrowly, about 0.5 mm to about 10.0 mm, including every 0.1 mm increment within these ranges (e.g., 1.0 mm, 2.5 mm, 7.5 mm, 10.0 mm).

FIG. $10B_2$ further illustrates that the textile second cross-sectional shape 54 can have a stadium shape.

FIG. $10B_3$ further illustrates that the textile second cross-sectional shape 54 can have an oblong, elliptical, or irregular shape.

The dimension $L_{11a}$ is also referred to as first shape first dimension.

The dimension $L_{12a}$ is also referred to as the first shape second dimension.

The dimension $L_{11b}$ is also referred to as second shape first dimension.

The dimension $L_{12b}$ is also referred to as second shape second dimension.

FIG. 11A illustrates that a reference shape 57 can overlaid the textile first cross-sectional shape 52. The reference shape 57 can have a reference shape center $57_C$ and a reference dimension $57_R$. For example, FIG. 11A illustrates that the reference shape 57 can be a reference circle having a reference circle center $57_C$ and a reference circle radius $57_R$. The circle center $57_C$ can coincide with the center of the textile first cross-sectional shape 52, the center of mass of the textile first cross-sectional shape 52 (e.g., actual center of mass of the textile cross-section, or can assume a nominal mass unit of 1 is distribute evenly across the textile first cross-sectional shape), or a center region of the textile first cross-sectional shape 52. The circle radius $57_R$ can be from about 0.5 mm to about 20.0 mm, or more narrowly, about 1.0 mm to about 10.0 mm, including every 0.1 mm increment within these ranges (e.g., 1.0 mm, 2.5 mm, 10.0 mm). The reference shape 57 can have reference shape area of about 0.05 mm$^2$ to about 15.00 mm$^2$, or more narrowly, about 0.25 mm$^2$ to about 4.00 mm$^2$, including every 0.01 mm$^2$ increment within these ranges. As another example, the reference shape 57 can be the cross-sectional shape of the die hole 19, for example, the size and shape of the textile outlet 36b. The reference shape area can be the same as or different from the cross-sectional area of the textile first cross-sectional shape 52. For example, the reference shape area can be equal to the area defined by the textile first cross-sectional shape 52. The textile first cross-sectional shape is also referred to as the first shape area. The cross-sectional area of the reference shape is also referred to as the reference shape area.

FIG. 11B illustrates that the reference shape 57 can overlaid the textile second cross-sectional shape 54. The circle center $57_C$ can coincide with the center of the textile second cross-sectional shape 54, the center of mass of the textile second cross-sectional shape 54 (e.g., actual center of mass of the textile cross-section, or can assume a nominal mass unit of 1 is distribute evenly across the textile first cross-sectional shape), or a center region of the textile second cross-sectional shape 54. The area of the textile second cross-sectional shape 54 is also referred to as the second shape area.

About 2% to about 95% of the first shape area can fit inside the reference shape 57, including every 1% increment within this range. About 5% to about 95% of the first shape area can fit inside the reference shape 57, including every 1% increment within this range. About 10% to about 100% of the second shape area can fit inside the reference shape 57, including every 1% increment within this range. About 25% to about 100% of the second shape area can fit inside the reference shape 57, including every 1% increment within this range. About 50% to about 100% of the second shape area can fit inside the reference shape 57, including every 1% increment within this range. About 75% to about 100% of the second shape area can fit inside the reference shape 57, including every 1% increment within this range. More of the second shape area can fit inside the reference shape 57 than the first shape area. For example, about 2% to about 98% more of the textile second cross-sectional shape 54 can fit inside the reference shape 57 than the textile first cross-sectional shape 52. To determine the percentage overlap between the textile first cross-sectional shape and the reference shape 57, the textile first cross-sectional shape 52 can be overlaid with the reference shape 57 such that the textile first cross-sectional shape center is coincident with the reference shape center $57_C$. To determine the percentage overlap between the textile second cross-sectional shape 54 and the reference shape 57, the textile second cross-sectional shape 54 can be overlaid with the reference shape 57 such that the textile second cross-sectional shape 54 center is coincident with the center of the reference circle. Where the cross-sectional shape has a fold 56, has a channel 42, and/or has an opening 43, the channel and/or the opening can be considered part of the textile second cross-sectional shape area (and be counted as part of the overlap with the reference shape 57) or can be considered separate from the second textile cross-sectional shape area (and not be counted as part of the overlap with the reference shape 57). As another example, the cross-sectional area of the channel 42 and/or opening 43 can be determined (e.g., using simple transparent graph paper and estimating the area or using a computer-aided method), and the reference shape 57 can be increased in size by this determined area. For example, where the reference shape 57 is a circle and the area of the channel and/or opening 42, 43 is determined, the reference shape area can be increased by the same amount (i.e., increased by the determined area), for example, by increasing the reference dimension $57_R$ the appropriate amount. For example, the cross-sectional area of the channel 42 in FIG. 11B can be determined and the reference circle radius $57_R$ in FIG. 11B can be larger than this dimension as shown in FIG. 11A, for example, by 0.1 mm to about 10.0 mm or more, including every 0.1 mm increment within this range, ultimately depending on the cross-cross-sectional area of the channel 42 and/or opening 43.

FIGS. $10A_1$-11B further illustrates that changing the textile first cross-sectional shape to the textile second cross-sectional shape can include changing one or more portions of the textile first cross-sectional shape perimeter from straight to curved, from curved to straight, from curved to more curved (e.g., from a first radius of curvature to a second radius of curvature, where the second radius of curvature is less than the first radius of curvature), from curved to less curved (e.g., from a first radius of curvature to a second radius of curvature, where the second radius of curvature is greater than the first radius of curvature), from angled to more angled (e.g., from a first angle between two straight portions to a second angle between the two straight portions, where the second angle can be less than the first angle, thereby making the angle more sharp or pointed), from angled to less angled (e.g., from a first angle between two straight portions to a second angle between the two straight portions, where the second angle can be greater than the first angle, thereby making the angle less sharp or pointed), from pointed to curved (e.g., from a point or tip, for example, where two sides of a perimeter come together at an angle, to a curve such that the point or tip of the perimeter is changed to a curved edge), from pointed to straight (e.g., from a point or tip, for example, where two sides of a perimeter come together at an angle, to straight such that the point or tip of the perimeter is changed to a straight edge), or any combination thereof.

FIGS. 12A and 12B illustrate that the shaper 10 can have one or multiple dies 18, for example, 1-10 dies 18, including every 1 die increment within this range (e.g., first through third dies 18a-18c).

FIG. 12B further illustrates that the shaper 10 can have one or multiple heaters 16, for example, 1-10 heaters 16, including every 1 heater 16 increment within this range (e.g., first and second heaters 16a, 16b).

FIG. 12B further illustrates that the heaters 16 (e.g., heaters 16a and 16b) and the dies 18 (e.g., dies 18a and 18b) can have the arrangement shown.

Method of Use

FIGS. 1A-12B illustrate that the textile 13 can be changed from the textile first cross-sectional shape 52 to the textile second cross-sectional shape 54. The textile first cross-sectional shape is also referred to as the suture first cross-sectional shape. The textile second cross-sectional shape is also referred to as the suture second cross-sectional shape.

FIG. 13 illustrates a variation of a process 60 that is implementable using and/or performable by the shaper 10. The method 60 can include heating the textile 13 (e.g., via the heater 16) in operation 62 and passing the heated portions of the textile 13 through the die 18 in operation 64. The die 18 can change the cross-sectional shape of the heated portions of the textile 13 from the textile first cross-sectional shape 52 to the textile second cross-sectional shape 54. The method 60 can include moving (e.g., pulling) a heated flat suture (e.g., textile 13) through the die 18. The method 60 can include moving (e.g., pulling) a heated non-flat suture (e.g., textile 13) through the die 18. The heated non-flat suture can be a round suture. The suture moved through the die 18 can be braided, non-braided, or both (e.g., having braided and non-braided sections).

The method can including passing heated and non-heated portions of the textile 13 through the die 18 to create sutures 37. The textile heated portions can be pulled through the die 18 at the same, lesser or greater textile speed as the textile non-heated portions, or vice versa. The textile heated portions can become the sections 40 and the textile non-heated portions can be become the sections 38. The textile heated portions can pass through the heater 16 and/or the die holes 19 at a textile speed of about 0.01 cm/s to about 1000 cm/s, or more narrowly, about 1 cm/s to about 25 cm/s, including every 1 and 0.01 centimeter/second increment. The textile non-heated portions can pass through the heater 16 and/or the die holes 19 at a textile speed of about 0.01 cm/s to about 1000 cm/s, or more narrowly, about 1 cm/s to about 25 cm/s, including every 1 and 0.01 centimeter/second increment.

The method 60 can include passing heated portions having a heated segment length of about 5 mm to about 5000 mm, or more narrowly, from about 5 mm to about 1000 mm, or more narrowly still, from about 5 mm to about 200 mm, including every 1 mm increment within these ranges. The method 60 can include passing non-heated portions having a non-heated segment length of about 5 mm to about 5000 mm, or more narrowly, from about 5 mm to about 1000 mm, or more narrowly still, from about 5 mm to about 200 mm, including every 1 mm increment within these ranges. The heated segment length can be the equal to, greater than, or less than the non-heated segment length.

The method 60 can include sizing the textile 13 to create one or multiple sutures (e.g., 1 to 5,000 or more sutures 37). After passing through the heater and the die 16, 18, the method 60 can include sizing the textile 13 in the heated portion, in the non-heated portion, or at the boundary or transition region between the heated and non-heated portions. For example, the textile 13 can be sized at the midpoint along the heated portions. As another example, the textile 13 can be sized as the midpoint along the non-heated portions.

The method 60 can include heating a flat section of textile (e.g., textile 13) and changing the shape of this section from flat to non-flat (e.g., round). The flat section of textile can be a flat braided section of the textile 13.

The method 60 can include heating a round section of textile (e.g., textile 13) and changing the shape of this section from round to another shape (e.g., a smaller round shape, a larger round shape, a non-round shape such as flat or oblong). The round section of textile can be a round braided section of the textile 13.

Braiding can occur upstream of the shaper 10. For example, everything disclosed (e.g., the braiding and braiding methods) in PCT Patent Application No. PCT/US2018/030746 filed May 2, 2018, which is herein incorporated by reference in its entirety for all purposes, can be used in combination with any of the apparatuses, systems, and methods disclosed herein. Further, elements of the apparatuses and methods disclosed in U.S. Pat. Nos. 7,908,956, 8,347,772, and 8,943,941, which are incorporated by reference herein in their entireties, can be used in combination with any of the apparatuses and methods disclosed herein.

The disclosure is related to a means for making textiles having more than one cross-sectional shape by using a combination of tension and/or compression and/or twisting and heat.

Currently certain textiles are formed using complicated machines that make textiles into their final shape. These machines tend to be very expensive and tend to have slow production rates. The orthopedic high strength suture market is evolving and flat sutures are becoming more preferable to conventional round sutures. The flat cross-sectional shape of newer suture designs is better at distributing stress over the anatomy without causing pull through. Pull through is when a suture has such a high load applied through it that it cuts through the tissue that it is holding. However, it is preferred that flat sutures have round or elliptical cross sections at the ends of the structure for ease of use of current suture passer technology and entry into the anatomy, among other purposes. The rounded ends of the suture allow the suture to be integrated into the suture passer instrumentation that is used to deliver the suture into the anatomy. For example, U.S. Patent Application Number 2005/0192631 describes a technique for making high strength suture tape by combining a round tape and a flat tape. The following disclosure proposes a novel method for forming a second cross-sectional shape into a portion of a suture or textile having a first cross-sectional shape, for example, forming round segments at the end of or in portions of the length of a flat polymer based textile.

A method is disclosed for making a textile having more than one cross-sectional shape. An embodiment is a method for forming a round cross-sectional shape on one or both ends of a flat tape high strength suture. That method includes providing a textile having a first cross-sectional shape, a longitudinal length and opposed side portions, the longitudinal length defining an longitudinal axis; selecting a portion of the textile to define a selected portion distinct from a non-selected portion; applying a first tensile force to the selected portion of the textile; moving the opposed side portions of the selected portion of the textile in a radial direction which is circumferential to the longitudinal axis to form a second cross-sectional shape which is different from the first cross-sectional shape; setting the second cross-sectional shape; and applying a second tensile force to the selected portion of the textile. The selected portion then has the second cross-sectional shape and the non-selected portion of the textile has the first cross-sectional shape.

The method may use heat applied to the textile, which causes the polymer used in the textile to slightly melt on the surface in an advantageous way. The textile may be a flat suture which may be twisted one or more times while placed under tension, for example, between a fixed gripper and a rotating gripper. Heat may then be applied to the twisted textile. Once the surface of textile has reached a specified temperature, the heating source may be removed and the textile may be stretched with an axial load. This produces a drawing effect and sets the permanent shape of the second cross-sectional shape, e.g., round or oval, of a portion of the textile, e.g., flat suture.

A process for forming a second cross-sectional shape within a textile disclosed herein may comprise the steps of: (a) isolating a portion of flat textile tape having a length; (b) applying limited tension (i.e., a first tensile force) to the portion; (c) applying a twist operation to the portion, thereby essentially changing the cross-sectional shape of structure change from flat to a second cross-sectional shape; (d) heating of the twisted portion with a heat source to a temperature at or slightly above the melt temperature of the material of the textile tape; (e) removing the heat source; and (f) increasing the tension (i.e., a second tensile force) of the heated twisted portion to produce a drawing effect.

A method for making a textile having more than one cross-sectional shape is disclosed. That method includes: (a) providing a textile having a first cross-sectional shape, a longitudinal length and opposed side portions, the longitudinal length defining a longitudinal axis; (b) selecting a portion of the textile to define a selected portion distinct from a non-selected portion; (c) applying a first tensile force to the selected portion of the textile; (d) moving the opposed side portions of the selected portion of the textile in a radial direction which is circumferential to the longitudinal axis to form a second cross-sectional shape which is different from the first cross-sectional shape; (e) setting the second cross-sectional shape in the selected portion; and (d) applying a second tensile force to the selected portion of the textile. The selected portion of the textile has the second cross-sectional shape and the non-selected portion of the textile has the first cross-sectional shape.

Any cross-sectional shape may be formed within any portion(s) and at any length(s) of the textile. This second cross-sectional shape may be, for example, circular (or round), oval, helical, C-shaped, star shaped, square, rectangular, etc. For example: round or oval portions may be formed at one or both ends of the textile, wherein the textile has a flat first cross-sectional shape; a helical portion may be formed in one or more middle portions of the textile, wherein the textile has a flat or round first cross-sectional shape; or a C shaped portion may be formed in one or more middle portions or ends of the textile, wherein the textile has a flat or round first cross-sectional shape. There are any number of possible combinations of cross-sectional shapes and placement within the length of the textile.

The textile may be of any first cross-sectional shape. This first cross-sectional shape may be, for example, circular (or round), oval, star shaped, square, rectangular, etc. The textile may be a flat or round braided structure or suture. It may be an elongate tape, or flat tape suture. The textile may be made from any known material found in the art, including but not limited to polyethylene (PE) (e.g., ultrahigh molecular weight polyethylene), polyester (PET), resorbable poly(L-lactic acid) (PLLA), resorbable polycaprolactone (PCL), resorbable polyglycolide or poly(glycolic acid) (PGA) and all molar ratios of the like, polydioxanone (PDO), aromatic polyesters (including but not limited to Liquid Crystal Polymer), high strength nylons (including but not limited to Kevlar), nylon, polytetrafluoroethylene (PTFE), and any combination thereof. Alternatively, the textile may comprise a polymeric material selected from the group consisting of ultra high molecular weight polyethylene (UHMWPE), polyethylene terephthalate (PET) polyesters, polypropylenes, polyethylenes, polyurethanes, polyolefins, polyvinyls, polymethylacetates, polyamides, naphthalane dicarboxylene derivatives, polyvinyl chloride, polytetrafluoroethylene, expanded polytetrafluoroethylene (ePTFE), fluorinated ethylene propylene copolymer, polyvinyl acetate, polystyrene, naphthalene dicarboxylate derivatives, polyurethane, polyurea, polyamides, polycarbonates, polyaldehydes, polyester copolymers, styrene-butadiene copolymers, polyethers, poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), polyphosphate ester) and any combination thereof.

The textile may be fabricated by any textile forming process including but not limited to: braiding, knitting, weaving, non-wovens with mechanical interlock feature, non-wovens with thermal interlock or electrospinning having a shape change operation done to them. The textile may be a braided textile, a knitted textile, a woven textile, an electro-spun textile, non-woven, or any combination thereof.

One or more portions of the textile is selected distinct from a non-selected portion for further processing in accordance with the disclosure. The selected portion(s) may be of any length and at any position within the textile. There may be one, two, three, four or more portions selected for further processing. The selected portions may be processed to be of the same cross-sectional shape or each may be processed to be of differing cross-sectional shapes.

Various shapes may be formed in any portion or multiple portions of the textile. The formation of different cross-sectional shapes may impart specific and useful properties to the textile often depending on the conditions used during processing. The amount of twist, the temperature, the tension applied, and the selection of other hot or cold molded compression dies may be varied to achieve different properties, shapes and sizes of the desired final textile.

In certain applications, it may be useful to have the second cross-sectional shape portion within the length of a textile rather than at the ends thereof. The processing machine or apparatus may be designed and programmed to create the varied cross-sectional shape at any point or points throughout the length of the textile. The second cross-sectional shape may even be formed in the full length of a textile to be stored on a spool or other storage technique, or at any position within a length of the textile.

Flat textiles that are processed in accordance with the disclosure to incorporate one or more round cross-sectional portions can be expected to have aspect ratios approximately equivalent to the mathematical value of $\pi$. If the heated round section is pulled with higher forces then the diameter of the round section or round sections will be lower than this mathematical relationship. In some circumstances, it may be beneficial to have a much smaller diameter round section relative to a specific starting width of a braided flat tape. This can be achieved by applying a higher tension value into the twisted and heated round section immediately after or during heating. The higher tension will cause a significantly higher drawing effect within the round section. Two non-limiting examples of this mathematical relationship: 1) a flat suture that is 3 mm wide would be expected to be 1 mm in diameter; and 2) with higher tension and higher draw ratios, a 3 mm wide suture would be expected to be smaller than 1 mm in diameter.

A first tensile force is applied to the selected portion of the textile. The first tensile force may be applied by closing both a fixed at one end of the selected portion and a traverse gripper at the other end of the selected portion. This tension is created by moving the traverse gripper away from the fixed gripper. The first tensile force may be about 0.5 pound-force to about 80 pounds-force, about 1 pound-force to about 70 pounds-force, about 2 pounds-force to about 70 pounds-force, about 1 pound-force to about 50 pounds-force, about 1 pound-force to about 20 pounds-force, about 1 pound-force to about 10 pounds-force, or about 1 pound-force to about 2 pounds-force. The amount of tension applied is determined by the desired end shape of the selected portion, e.g., rounded. A higher tension will produce a rounded section on the portion of textile that is between the grippers. When using tension and twisting to produce a solid cross section construct then the first tensile load may be applied so that the subsequently applied movement (e.g., twist) is evenly spread along the selected portion. In an embodiment, when a twisting motion is to be subsequently applied, the first tensile force may be about 0.5 pound-force to about 80 pounds-force, about 1 pound-force to about 20 pounds-force, about 1 pound-force to about 10 pounds-force, or about 1 pound-force to about 2 pounds-force. In an embodiment, when a curling motion is to be subsequently applied, the first tensile force may be about 0.5 pound-force to about 80 pounds-force, about 1 pound-force to about 70 pounds-force, about 2 pounds-force to about 70 pounds-force, or about 1 pound-force to about 50 pounds-force, The opposed side portions of the selected portion of the textile is moved in a radial direction which is circumferential to the longitudinal axis. This movement may be accomplished using a twisting motion by using any machinery that may accomplish said purpose. In an embodiment, to accomplish the twisting, the first longitudinal end may be secured (releasably) by a fixed gripper, and the second longitudinal end may be secured (releasably) by a rotating gripper. The rotating gripper is then rotated to twist the selected portion of the textile while applying the first tensile force. This process essentially forms a cross-sectional shape which is different from the first cross-sectional shape.

The amount of twist is proportional to the starting width of the textile. Twisting the selected portion of the textile may be done at a rate from about 2 turns per inch of longitudinal length of the selected portion to about 10 turns per inch of longitudinal length of the selected portion, at a rate from about 3 turns per inch of longitudinal length of the selected portion to about 5 turns per inch of longitudinal length of the selected portion, or at a rate of about 4 turns per inch of longitudinal length of the selected portion. It has been found that the hardness or compressive strength of the selected portion (e.g., rounded section) may be increased by using a higher twist rate. A higher twist rate may also produce a smoother selected portion. It has also been found that the larger starting width of a flat textile tape will require more twisting than a narrower one to produce the same results.

This movement may also be accomplished by curling the opposed side portions of the selected portion of the textile by using any machinery that may accomplish said purpose.

In the step of setting the second cross-sectional shape in the selected portion, the second cross-sectional shape of the selected portion of the textile is formed. Optionally, setting the shape comprises: providing a heat source and heating the selected portion with the heat source. The selected portion of the textile may be heated to a temperature at, above or near the melt temperature of the polymeric material. The heat source may be an infrared heat source or any heated die or molded compression die.

To sufficiently heat the surface of a textile, using an infrared heat source may require a longer period of time and may also require a higher temperature than using a heated die. The heat source may comprise both an infrared heat source and a heated die or molded compression die. The heated die may have a cross-sectional shape formed therein that is different from the cross-sectional shape of the textile. Any heated die of any shape machined therein may be used. The heated die may be used in combination with applied pressure to compress the select portion of the textile, thereby ultimately altering its cross-sectional shape. In an embodiment, the heated die may have any shape machined into it as long as the cross-sectional area of the shape is 1% to 50% smaller than the first cross-sectional area of the textile being processed.

The die may be a 3D die. This die is able to heat and cool quickly to be able to shape only the targeted selected portion of the textile. On one side it has a round opening through which the textile may pass. On the exit side, another shape such as rectangular, square, W, N or V, is formed in the die, see for example FIGS. 24 and 25. In this way, the textile enters the heated 3D die and then is folded and pleated as it passes through the shaped exit to permanently form another shape. Once the 3D die is cooled, the remainder of the textile can be pulled through the die without permanently changing its shape.

The compression die may be heated, ambient or chilled and may be used instead of an infrared heat source, such as a set block, or be used in addition to an infrared heat set block. The compression die may use hydraulic or pneumatic pressure to actuate and generate significant pressure within the textile. This is generally known as hot or cold forming.

Optionally, setting the shape may also comprise one or more of the following steps: compressing the selected portion of the textile; and/or removing the heat source after heating. Compressing may be accomplished by using a weighted hot or cold compression die.

A second tensile force is applied to the set selected portion of the textile. The second tensile strength may be applied by moving the traverse gripper at one end of the selected portion relative to the fixed gripper at the other end of the selected portion. The amount of tension that is applied defines the relationship between the starting width/shape of a textile and the width/shape of the selected portion. For example, a higher tension will reduce the diameter of the selected portion, e.g., rounded, relative to a constant width of the textile. The second tensile force may be about 0.5 pound-force to about 20 pounds-force, about 0.5 pound-force to about 10 pounds-force, about 1 pound-force to about 10 pounds-force, or about 1 pound-force to about 5 pounds-force.

Any method disclosed herein may further include providing a sacrificial wire and helically winding the selected portion of the textile about the sacrificial wire. Alternatively the method may further include inserting the sacrificial wire through the twisted portion of the textile. The sacrificial wire may be within the entire length of the twisted (or shaped) portion. The textile may then be processed as described above and then the sacrificial wire removed after setting the second cross-sectional shape and, optionally, after applying the second tensile force to generate a hollow cylindrical portion, for example within a round portion of the textile. The sacrificial wire may be made of any material and may be of any thickness and length. If the wire is made of a similar material to that of the textile, then the wire may be fused into the textile if a high enough temperature is used during processing.

An apparatus for forming a varied cross-sectional shape within a textile is disclosed. The apparatus may be used for performing any method disclosed above. The apparatus may include a fixed gripper for releasably securing a first portion of the textile; a rotatable gripper for releasably securing and twisting a second portion of the textile; and a heating and compression element positioned between the fixed gripper and the rotatable gripper. The terms and conditions used in this embodiment have the same meaning as defined above.

The heating and compression element may comprise a heated die or a hot or cold compression die. The heating and compression element may be a hot compression die, and may further comprise an infrared heat source.

A textile is also disclosed that is made up of polymeric fibers having a varied cross-sectional shape, wherein the polymeric fibers are integrally woven throughout the textile, made by: (a) providing the textile having a first cross-sectional shape, a longitudinal length and opposed side portions, the longitudinal length defining a longitudinal axis; (b) selecting a portion of the textile to define a selected portion distinct from a non-selected portion; (c) applying a first tensile force to the selected portion of the textile; (d) moving the opposed side portions of the selected portion of the textile in a radial direction which is circumferential to the longitudinal axis to form a second cross-sectional shape which is different from the first cross-sectional shape; (e) setting the second cross-sectional shape in the selected portion; and (d) applying a second tensile force to the selected portion of the textile. The terms and conditions used in this embodiment have the same meaning as defined above.

The textile may include an interface between the selected portion of the textile and the non-selected portion of the textile free of stitches and glue.

The selected portion of the textile has a circular or oval cross-sectional shape, and/or the non-selected portion of the textile has a flat rectangular cross-sectional shape.

The term "integrally woven" means that the parts or segments of the textile, e.g., suture, are woven together to make the whole of the textile. The integrally woven textile formed in accordance with the disclosure may be made to be any length and of any diameter.

Another embodiment is a textile suture made up of integrally woven polymeric fibers comprising at least one selected portion having a first cross-sectional shape, and at least one non-selected portion having a second cross-sectional shape. The terms and conditions used in this embodiment have the same meaning as defined above.

The textile suture may comprise one or two selected portions and each selected portion may have a round cross-sectional shape. When there are two selected portions, they may be located at the ends of the suture.

The following examples are meant to be exemplary and not limiting of the embodiments described herein.

EXAMPLES

Example 1

A high strength suture comprised of 17 ends of 125 denier PE was used. This braided textile has an initial rectangular cross-sectional shape before any further processing. The lot size or length of material would be defined by the capacity of the braiding machine and would be taken up on a master spool 7, positioned at one end of the apparatus, at lengths that could range from several meters all the way up to 10,000 plus meters. The master spool would then be removed from the braiding equipment and fitted to the round tipping machine shown in FIGS. 16, 17 and 18. The end of the suture tape would be inserted through the fixed gripper 72 and then through the rotating gripper 74 and then the machine would be started. For this particular combination, it has been found experimentally that to achieve the best tipping configuration for this example the suture is twisted at a rate of 4 turns per inch while the tip is placed under one to two pounds of tension. The length of twisted region is two inches long for a total of 8 turns. Then the machines infrared heat set block 16 is inserted around the twisted region of the suture. Ideal temperature for PE is approximately 250° C. with a dwell time of five seconds. The infrared heat set block 16 is then withdrawn and the machine creates tension by under-driving the master spool 7 while the traverse gripper 76 moves away from the master spool. This produces a drawing effect within the yarns and makes them have better heat treated characteristics and a stiffer rounded section. This combination produced a flat suture structure 2 with a round cross section end 1, 3, as shown in FIG. 14. The flat section of the suture had a width of 1.9 mm and a rounded tip diameter of 0.6 mm. It is understood that the machine incorporates a length indexing traverse gripper 76, a mechanical cutter 78 or laser cutter and a storage bin 11. These components would be used to allow the machine to continually run and continue to make discrete round/flat suture parts.

The machine and method described above to produce a round shaped end could alternatively incorporate a heated die, as shown in FIG. 19 with any shape machined into it. This would allow for forming almost any shape into a portion of the textile. The heated die could be heated, ambient or chilled and could replace the infrared heat set block 16 or be used in addition to the infrared heat set block. The heated die set could use hydraulic or pneumatic pressure to actuate and would generate significant pressure within the textile, i.e., hot or cold forming.

Example 2

In this example, 13 ends of 100 denier PE are processed to create a round cross-sectional shape portion in the center of the suture, as shown in FIG. 15, of the discrete one meter of final cut length. The ends of the suture length 4, 6 are flat and the center section 5 is processed to be round. The machine allows the length of the suture to be longer on the end. The fixed gripper 72 would have approximately one half of the intended length of the final product. This machine would require different programming commands that are well understood by people skilled in the art of PLC logic and other motion control software systems.

Example 3

A round braided textile that is comprised of 16 ends of 100 denier PET could be wrapped around a sacrificial mandrel 80 using the fixture found in FIG. 20. Once the textile is wrapped around the mandrel as shown in FIG. 20, then the heating block 16 is extended to heat the textile. The sacrificial mandrel 80 is removed after setting of the shape and the braid retains a helical shape 82 as compared to the straight portion 84.

Example 4

A flat braid comprised of 17 ends of 125 denier PE was processed to make a textile having varied cross-sectional shapes as found in FIG. 22. Using an apparatus similar to the one found in FIG. 16, the braid spool 7 was installed onto machine. The end of the flat braid was connected to the traverse gripper 76 and the machine was started. The traverse gripper was instructed to apply a significant amount of tension within the flat braid. Loads between 2 to 70 pounds will cause this effect but more preferably loads in the higher end of this spectrum produced the best results. The tension causes the flat braid 86 to curl 87 on the edges and if enough tension is applied the braid will roll completely into a round cross section 88 as generally shown in FIGS. 22 and 23. Then the heated block 16 was traversed outward to heat treat the newly formed round cross section 88 for 3 seconds at a temperature 250° C. Then the heated block 16 was removed and the traverse gripper 76 was moved slightly faster than the let off servo motor 8. This generated tension within the textile. For this example, it was found that 1 to 5 pounds of tension produced the best results.

Example 5

A round braid comprised of 8 ends of 200 denier PLGA was compressed and heat treated with a heated compression die as shown in FIG. 19. The heated compression die was added to apparatus of in FIG. 16 taking the place of the heated block 16, which was removed.

Example 6

A flat braid comprised of 17 ends of 100 denier PE was passed through a heated 3D die 90 in FIG. 24 to produce a round end on a flat tape construct. The entrance side of the die 90 is rectangular in shape and the exit side of the die has a round shape 92 as shown in FIG. 25. This 3D die was used in place of the heated die 16 in FIG. 16. The flat braid textile was passed through the 3D die and inserted in the fixed gripper 72. The fixed gripper then moved away from the spool 7 and pulled the flat textile through the 3D die. The 3D die is made with a very low thermal mass and is quickly heated and cooled back to ambient temperature when the machine is programmed to produce a round portion within the flat tape. Then the traverse gripper 76 then moved away further from the spool 7. This length was defined by the operator. Then the fixed gripper 72 was closed to hold the flat tape. The scissor 78 was actuated to cut the braided construct in correct position which is defined by the operator. The traverse gripper 76 then opened to drop the tape with rounded ends into the storage bin 11. This process may continue until the correct number of units are made. The cross sectional shape of the round shape exit 92 end of the 3D die can be but is not limited to W, N or V profiles. FIG. 31 shows a textile processed with a V profile die, wherein the selected portion 94 has a V shape and the non-selected portion 96 remains flat.

Example 7

To produce a highly drawn structure as show in FIG. 26, a high strength suture comprised of 17 ends of 125 denier PE was used. Highly drawn refers to a higher degree of molecular orientation within the textile section that has been altered. This allows for a smaller diameter of the round section relative to the original shape of the textile. A higher degree of draw also inherently increases the stiffness of the polymer. This braided structure had a rectangular cross-sectional shape 98 before application of any processing disclosed herein. The master spool 7 of braided material was attached to the apparatus of FIGS. 16, 17 and 18. The end of the suture tape was inserted through the fixed gripper 72 and then through the rotating gripper 74 and then the machine was started. For this particular combination, it was found that to achieve the best configuration, the suture would be twisted at a rate of 4 turns per inch while the selected portion at the end (or tip) is placed under one to two pounds of tension. The length of twisted region was measured at two inches long for a total of 8 turns. Then the infrared heat set block 16 was inserted around the twisted portion of the suture. Ideal temperature for PE would be approximately 250° C. with a dwell time of five seconds. The infrared heat set block 16 was then withdrawn and tension was created by under-driving the master spool 7 while the traverse gripper 76 moves away from the master spool. A significantly higher tension was used compared to Example 1, thereby producing a significantly more pronounced drawing effect as compared with Example 1. This combination produced a flat suture 98 with a round cross section end 100. The flat section 98 had a width of 1.9 mm and a rounded tip 100 had a diameter of 0.4 mm. It is understood that the machine would incorporate a length indexing traverse gripper 72, a mechanical cutter 78 or laser cutter, and a storage bin 11. These components would be used to allow the machine to continually run and continue to make round/flat suture portions.

Example 8

To produce a button hole type feature within the width of the braid, a PET braid comprised of 13 ends of 150 denier PET was used. The spool of braided material was installed onto a variant of the machine of FIG. 16. This variant machine had a needle type heated element 35 as shown in FIG. 32 in place of or in addition to the heated block 16. This needle type heated element would not be heated until it is ready to be inserted into the braid. The needle would be inserted between two picks within the braid 102 to minimize any detrimental effects caused within the braid by piercing individual yarns. Once the needle is inserted to full depth, the internal heating element within the needle, would be applied to bring the temperature of the adjacent yarn to its heat treatment temperature or all the way up to and including the materials melt temperature, which for this example is 205° C. Then a cooling mechanism using compressed air would be applied to cool the needle type heated element. The needle would be removed once it had been cooled adequately and the machine run similarly to the one in Example 1 to cut the textile into a discrete length if desired. The resulting braid would have pockets or holes 104 and 106 as shown in FIGS. 32 and 33. Depending on design, the diameter of the heated needle could cause a change in the width of the construct 108.

Example 9

A high strength suture comprised of 17 ends of 125 denier PE was used. This braided structure had a rectangular cross-sectional shape before processing. The master spool 7 would then be removed from the braiding equipment and fitted to the round tipping machine FIGS. 16, 17 and 18. The end of the suture tape would be inserted through the fixed gripper 72 and then through the rotating gripper 74 and then the machine would be started. For this particular combination, a radial forming block FIGS. 28 and 29 was fitted to the machine to the right position of the heated block 16 in FIG. 16. It has been found that it was possible to achieve a curved round section 110, as shown in FIG. 30. The best configuration for this example is achieved by twisting the braided suture at a rate of 4 turns per inch while the end (tip) is placed under one to two pounds of tension. The length of the twisted region would be two inches long for a total of 8 turns. Then the machines infrared heat set block 16 would be inserted around the twisted region of the suture. Ideal temperature for PE would be approximately 250° C. with a dwell time of five seconds. The infrared heat set block 16 is then withdrawn and the machine moves the indexing gripper 76. The radial forming block FIG. 28 would be raised so that the rounded suture section would run over the v block profile. The under drive condition can be creating by moving the traverse gripper 76 faster than the let off 8 or the tension can be created by raising the radial forming block FIG. 28 within the path of the rounded suture. It has been found that a curved bias 110 can be added to the rounded section 112 of braid having a rectangular non-selected portion 114. This produces a drawing effect within the yarns and makes them have better heat treated characteristics and a stiffer curved and rounded section. This combination produced a flat suture structure 114 with a round cross section end 112. The flat section 114 of the suture had a width of 1.9 mm and a rounded tip 112 diameter of 0.6 mm. While this example shows forming a single round cross-sectional portion at the end of the suture, one or more round cross-sectional portions may also be formed along any point or section of the suture length.

Example 10

A flat braid that was comprised of 17 ends of 125 denier PE was fixtured to produce a textile shape as found in FIG. 22. Using a fixture similar to the one found in FIG. 16, the braid spool 7 was installed onto machine. The end of the flat braid was connected to the traverse gripper 76 and the machine was started. The traverse gripper was programmed to apply almost no tension during the heating phase—loads below 1 pound and approaching no tension. The traverse gripper 76 was instructed to continue to apply low tension causing the shaped round section to axial shorten and grow in diameter. Then the heated block 16 was removed and the system remained static for 5 seconds to allow the heated section to cool. Then the traverse gripper 76 was moved over the storage bin 11 and released the braid. As in other examples, the machine may be programmed to continue to repeat the process, as desired.

As those skilled in the art will appreciate, numerous changes and modifications may be made to the embodiments described herein, without departing from the spirit of the disclosure. It is intended that all such variations fall within the scope of the invention.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the disclosure, and variations of aspects of the disclosure can be combined and modified with each other in any combination.

We claim:

1. A method for making a braided textile suture comprising:
   pulling a braided textile through a heater;
   heating alternating portions of the braided textile via the heater from a textile first temperature to a textile second temperature greater than the textile first temperature;
   pulling heated portions and non-heated portions of the braided textile through a die; and
   changing a cross-sectional shape of the heated portions from a textile first cross-sectional shape to a textile second cross-sectional shape when the heated portions are pulled through the die.

2. The method of claim 1, wherein the textile first cross-sectional shape is a flat shape.

3. The method of claim 2, wherein the textile second cross-sectional shape is a non-flat shape.

4. The method of claim 1, further comprising sizing the textile to create a braided suture having a suture first portion and a suture second portion, wherein the suture first portion has the textile first cross-sectional shape, and wherein the suture second portion has the textile second cross-sectional shape.

5. The method of claim 4, wherein the braided suture further comprises a suture third portion, wherein the suture third portion has a textile third cross-sectional shape.

6. The method of claim 5, wherein the textile third cross-sectional shape is a folded shape.

7. The method of claim 6, wherein the suture third portion is between the suture first and second portions.

* * * * *